United States Patent
Piron et al.

(10) Patent No.: US 11,786,310 B2
(45) Date of Patent: *Oct. 17, 2023

(54) INTERMODAL SYNCHRONIZATION OF SURGICAL DATA

(71) Applicant: SYNAPTIVE MEDICAL INC., Toronto (CA)

(72) Inventors: Cameron Piron, Toronto (CA); Gal Sela, Toronto (CA); Monroe M. Thomas, Toronto (CA); Simon Alexander, Toronto (CA); Murugathas Yuwaraj, Toronto (CA); Michael Wood, Toronto (CA); Alex Panther, Toronto (CA); Joshua Richmond, Toronto (CA); Wes Hodges, Toronto (CA); David Gallop, Toronto (CA)

(73) Assignee: Synaptive Medical Inc.

( * ) Notice: Subject to any disclaimer, the term of this patent is extended or adjusted under 35 U.S.C. 154(b) by 262 days.

This patent is subject to a terminal disclaimer.

(21) Appl. No.: 17/160,511

(22) Filed: Jan. 28, 2021

(65) Prior Publication Data
US 2021/0153943 A1    May 27, 2021

Related U.S. Application Data

(63) Continuation of application No. 15/597,830, filed on May 17, 2017, now Pat. No. 10,959,779, which is a
(Continued)

(51) Int. Cl.
*A61B 34/10* (2016.01)
*G06T 7/30* (2017.01)
(Continued)

(52) U.S. Cl.
CPC ............ *A61B 34/10* (2016.02); *A61B 5/0075* (2013.01); *A61B 5/7246* (2013.01);
(Continued)

(58) Field of Classification Search
CPC .................................................... A61B 34/10
See application file for complete search history.

(56) References Cited

U.S. PATENT DOCUMENTS

| | | | | |
|---|---|---|---|---|
| 2011/0125011 | A1* | 5/2011 | Wieczorek | A61B 34/10 600/427 |
| 2014/0114679 | A1* | 4/2014 | Anderson | G16H 30/40 705/2 |

FOREIGN PATENT DOCUMENTS

WO    2012154216    11/2012

OTHER PUBLICATIONS

Hoisak, J. D. P. (2012). A measure of voxel similarity for improving the image-based quantification of tissue structure and function (Order No. NR97344). Available from ProQuest Dissertations and Theses Professional. (1349334283) (Year: 2012).*

(Continued)

*Primary Examiner* — Sheetal R Paulson

(57) ABSTRACT

Systems and methods are provided in which local tissue diagnostic measurements are correlated with archival local tissue diagnostic data from prior tissue analyses to supplement diagnostic measurements with tissue analysis data from prior tissue analyses having similar local tissue diagnostic data. The tissue analysis data may include information such as pathology data, outcome data, and diagnosis data. The archived local tissue diagnostic data and the tissue analysis data may be stored in a database, and employed for a wide variety of methods, involving preoperative, intraoperative, and/or postoperative phases of a medical procedure. Methods and systems are also provided for displaying, on a medical image shown in a user interface, hyperlinked reference markers associated with tissue analyses, where the reference markers are shown at locations corresponding to local tissue analyses, and where associated diagnostic data
(Continued)

and/or tissue analysis may be viewed by selecting a given reference marker.

20 Claims, 27 Drawing Sheets

Related U.S. Application Data continuation of application No. 14/855,054, filed on Sep. 15, 2015, now Pat. No. 10,660,705, which is a continuation of application No. PCT/CA2014/050269, filed on Mar. 14, 2014.

(60) Provisional application No. 61/924,993, filed on Jan. 8, 2014, provisional application No. 61/818,255, filed on May 1, 2013, provisional application No. 61/801,746, filed on Mar. 15, 2013, provisional application No. 61/798,867, filed on Mar. 15, 2013, provisional application No. 61/800,155, filed on Mar. 15, 2013, provisional application No. 61/800,911, filed on Mar. 15, 2013, provisional application No. 61/801,282, filed on Mar. 15, 2013.

(51) Int. Cl.

| | | |
|---|---|---|
| *A61B 34/00* | (2016.01) | |
| *A61B 17/34* | (2006.01) | |
| *A61B 5/00* | (2006.01) | |
| *G06T 7/00* | (2017.01) | |
| *G16H 50/70* | (2018.01) | |
| *G16H 50/20* | (2018.01) | |
| *G16H 10/40* | (2018.01) | |
| *G16H 20/40* | (2018.01) | |
| *G16H 40/20* | (2018.01) | |
| *G16H 30/20* | (2018.01) | |
| *G16H 50/50* | (2018.01) | |
| *G16H 30/40* | (2018.01) | |
| *A61B 34/20* | (2016.01) | |
| *A61B 90/50* | (2016.01) | |
| *A61B 90/57* | (2016.01) | |
| *A61B 90/00* | (2016.01) | |
| *G16H 10/60* | (2018.01) | |
| *G16H 70/20* | (2018.01) | |
| *A61B 90/10* | (2016.01) | |

(52) U.S. Cl.
CPC .......... *A61B 17/3421* (2013.01); *A61B 34/20* (2016.02); *A61B 34/25* (2016.02); *G06T 7/0014* (2013.01); *G06T 7/30* (2017.01); *G16H 10/40* (2018.01); *G16H 20/40* (2018.01); *G16H 30/20* (2018.01); *G16H 30/40* (2018.01); *G16H 40/20* (2018.01); *G16H 50/20* (2018.01); *G16H 50/50* (2018.01); *G16H 50/70* (2018.01); *A61B 90/50* (2016.02); *A61B 2034/101* (2016.02); *A61B 2034/105* (2016.02); *A61B 2034/107* (2016.02); *A61B 2034/2051* (2016.02); *A61B 2034/2055* (2016.02); *A61B 2034/252* (2016.02); *A61B 2034/256* (2016.02); *A61B 2090/103* (2016.02); *A61B 2090/365* (2016.02); *A61B 2090/374* (2016.02); *A61B 2090/378* (2016.02); *A61B 2090/3762* (2016.02); *A61B 2090/571* (2016.02); *A61B 2576/026* (2013.01); *G06T 2207/30016* (2013.01); *G16H 10/60* (2018.01); *G16H 70/20* (2018.01)

(56) References Cited

OTHER PUBLICATIONS

Search report issued by the Intellectual Property Office of Singapore in relation to SG Application No. 10201707562P dated Aug. 23, 2021, 2 pgs.

\* cited by examiner

INTERROGATED REGION VIDEO SCAN

COMBINED IMAGING REFORMAT

INTERMODAL SYNCHRONIZATION OF SURGICAL DATA

CROSS-REFERENCE TO RELATED APPLICATIONS

This document is a continuation application claiming the benefit of, and priority to, the following documents: U.S. patent application Ser. No. 15/597,830; titled "INTERMODAL SYNCHRONIZATION OF SURGICAL DATA," and filed on May 17, 2017; U.S. patent application Ser. No. 14/855,054 filed Sep. 15, 2015; International PCT Patent Application No. PCT/CA2014/050269 filed on Mar. 14, 2014; U.S. Provisional Application No. 61/801,282, titled "SYSTEMS AND METHODS FOR PATHOLOGY TRACKING" and filed on Mar. 15, 2013; U.S. Provisional Application No. 61/800,911, titled "HYPERSPECTRAL IMAGING DEVICE" and filed on Mar. 15, 2013; U.S. Provisional Application No. 61/801,746, titled "INSERT IMAGING DEVICE" and filed on Mar. 15, 2013; U.S. Provisional Application No. 61/818,255, titled "INSERT IMAGING DEVICE" and filed on May 1, 2013, U.S. Provisional Application No. 61/800,155, titled "PLANNING, NAVIGATION AND SIMULATION SYSTEMS AND METHODS FOR MINIMALLY INVASIVE THERAPY" and filed on Mar. 15, 2013; U.S. Provisional Application No. 61/924,993, titled "PLANNING, NAVIGATION AND SIMULATION SYSTEMS AND METHODS FOR MINIMALLY INVASIVE THERAPY" and filed on Jan. 8, 2014; U.S. Provisional Application No. 61/798,867, titled "SYSTEM AND METHOD FOR RECORDING THE TIME COURSE OF TOOLS THROUGH A PROCEDURE" and filed on Mar. 15, 2013, all of which are hereby incorporated herein by reference in their entirety.

FIELD

The present disclosure relates to image guided medical procedures. The present disclosure also relates to medical procedures involving tissue excision, identification and/or pathology analysis.

BACKGROUND

Imaging and imaging guidance is becoming a more significant component of surgical care, from diagnosis of disease, monitoring of the disease, planning of the surgical approach, guidance during the procedure and follow-up after the procedure is complete, or as part of a multi-faceted treatment approach.

In many medical procedures, tissue samples are excised or examined, for example, during the surgical removal of a tumor. Currently, in the fields of medical imaging and surgical diagnostics, taking a tissue sample and performing histopathology examination of the tissue sample, using a microscope, often with staining of that tissue, remains the gold standard for tissue diagnosis. This histopathology examination involves resection in a surgical suite and transfer of the sample to a pathology laboratory.

However, this histopathology examination approach is fraught with problems and issues. For example, current methods of tissue analysis are unable to accurately and painlessly access tissue and can result in the possibility of seeding tumor cells through the biopsy process. This histopathology examination approach is also typically impractical to perform multiple biopsies to enable proper examination of heterogeneous tumors.

Tissue samples are also often mislabeling during the process, which can result due to sample mix-up or labelling errors resulting in faulty diagnosis. Furthermore, pathology results may be discordant with the imaging results. Current workflow also often has a poor feedback loop to radiologists, hindering them from improving their diagnostic accuracy for future cases. This also can result in an unnecessary delay between biopsy and pathology results, resulting in a reduction in positive patient outcomes.

SUMMARY

Systems and methods are provided in which local tissue diagnostic measurements are correlated with archival local tissue diagnostic data from prior tissue analyses to supplement diagnostic measurements with tissue analysis data from prior tissue analyses having similar local tissue diagnostic data. The tissue analysis data may include information such as pathology data, outcome data, and diagnostic data. The archived local tissue diagnostic data and the tissue analysis data may be stored in a database, and employed for a wide variety of methods, involving preoperative, intraoperative, and/or postoperative phases of a medical procedure. Methods and systems are also provided for displaying, on a medical image shown in a user interface, hyperlinked reference markers associated with tissue analyses, where the reference markers are shown at locations corresponding to local tissue analyses, and where associated diagnostic data and/or tissue analysis may be viewed by selecting a given reference marker.

Accordingly, in one aspect, a computer implemented method of correlating a local tissue diagnostic measurement with archival tissue analysis data is provided, the method comprising: obtaining local tissue diagnostic data associated with one or more local tissue diagnostic measurements performed on a subject; accessing archival local tissue diagnostic data and tissue analysis data associated with one or more prior local tissue analyses; comparing, according to pre-selected similarity criteria, the local tissue diagnostic data associated with the one or more local tissue diagnostic measurements and the archival local tissue diagnostic data associated with the one or more prior local tissue analyses; identifying one or more similar prior local tissue analyses having archival local tissue diagnostic data satisfying the pre-selected similarity criteria; and providing tissue analysis data associated with the one or more similar prior local tissue analyses.

In another aspect, a system for correlating a local tissue diagnostic measurement with archival tissue analysis data is provided, the system comprising: a control and processing system comprising one or more processors and memory coupled to said one or more processors, said memory storing instructions, which, when executed by said one or more processors, causes said one or more processors to perform operations comprising: obtaining local tissue diagnostic data associated with one or more local tissue diagnostic measurements performed on a subject; accessing archival local tissue diagnostic data and tissue analysis data associated with one or more prior local tissue analyses; comparing, according to pre-selected similarity criteria, the local tissue diagnostic data associated with the one or more local tissue diagnostic measurements and the archival local tissue diagnostic data associated with the one or more prior local tissue analyses; identifying one or more similar prior local tissue analyses having archival local tissue diagnostic data satisfying the pre-selected similarity criteria; and providing tissue analysis data associated with the one or more similar prior local tissue analyses.

In another aspect, a computer implemented method of displaying tissue analysis information on a user interface is provided, the method comprising: obtaining a medical image of at least a portion of a subject and displaying the medical image on the user interface; obtaining local tissue information corresponding to one or more local tissue analyses performed on the subject; obtaining location data identifying a location corresponding to each local tissue analysis, wherein the location data is spatially registered to the medical image; displaying one or more reference markers in the medical image, wherein: each reference marker is associated with one of the local tissue analyses; and each reference marker is displayed, in the medical image, at the location at which its associated local tissue analysis was performed; receiving input from an operator identifying a selected reference marker associated with a selected local tissue analysis, thereby identifying selected local tissue information; and presenting at least a portion of the selected local tissue information associated with the selected local tissue analysis.

In another aspect, a system for displaying tissue analysis information on a user interface is provided, the system comprising: a control and processing system interfaced with a display device, said control and processing system comprising one or more processors and memory coupled to said one or more processors, said memory storing instructions, which, when executed by said one or more processors, causes said one or more processors to perform operations comprising: obtaining a medical image of at least a portion of a subject and displaying the medical image on the user interface; obtaining local tissue information corresponding to one or more local tissue analyses performed on the subject; obtaining location data identifying a location corresponding to each local tissue analysis, wherein the location data is spatially registered to the medical image; displaying one or more reference markers in the medical image, wherein: each reference marker is associated with one of the local tissue analyses; and each reference marker is displayed, in the medical image, at the location at which its associated local tissue analysis was performed; receiving input from an operator identifying a selected reference marker associated with a selected local tissue analysis, thereby identifying selected local tissue information; and presenting at least a portion of the selected local tissue information associated with the selected local tissue analysis.

In another aspect, a computer implemented method of correlating preoperative tissue analysis data with archival tissue analysis data from one or more prior medical procedures is provided, the method comprising: obtaining preoperative tissue analysis data associated with a subject; accessing archival tissue analysis data associated with one or more prior medical procedures; accessing time-dependent medical procedure data recorded during the one or more prior medical procedures; comparing, according to pre-selected similarity criteria, the preoperative tissue analysis data and the archival tissue analysis data associated with the one or more prior medical procedures; identifying one or more similar prior medical procedures having archival tissue analysis data satisfying the pre-selected similarity criteria; and processing the time-dependent medical procedure data associated with the one or more similar prior medical procedures to replay at least a portion of the medical procedure.

In another aspect, a system for correlating preoperative tissue analysis data with archival tissue analysis data from one or more prior medical procedures is provided, the system comprising: a control and processing system comprising one or more processors and memory coupled to said one or more processors, said memory storing instructions, which, when executed by said one or more processors, causes said one or more processors to perform operations comprising: obtaining preoperative tissue analysis data associated with a subject; accessing archival tissue analysis data associated with one or more prior medical procedures; accessing time-dependent medical procedure data recorded during the one or more prior medical procedures; comparing, according to pre-selected similarity criteria, the preoperative tissue analysis data and the archival tissue analysis data associated with the one or more prior medical procedures; identifying one or more similar prior medical procedures having archival tissue analysis data satisfying the pre-selected similarity criteria; and processing the time-dependent medical procedure data associated with the one or more similar prior medical procedures to replay at least a portion of the medical procedure.

In another aspect, a computer implemented method of suggesting one or more steps of a surgical plan based on archival surgical plan data from one or more prior medical procedures is provided, the method comprising: obtaining tissue analysis data associated with a subject; accessing archival tissue analysis data associated with one or more prior medical procedures; accessing surgical plan data associated with the one or more prior medical procedures; comparing, according to pre-selected similarity criteria, the tissue identification data and the archival tissue analysis data associated with the one or more prior medical procedures; identifying one or more similar prior medical procedures having archival tissue analysis data satisfying the pre-selected similarity criteria; and processing the surgical plan data associated with the one or more similar prior medical procedures to generate one or more steps of a suggested surgical plan; and communicating the one or more steps of the suggested surgical plan.

In another aspect, a system for suggesting one or more steps of a surgical plan based on archival surgical plan data from one or more prior medical procedures is provided, the system comprising: a control and processing system comprising one or more processors and memory coupled to said one or more processors, said memory storing instructions, which, when executed by said one or more processors, causes said one or more processors to perform operations comprising: obtaining tissue analysis data associated with a subject; accessing archival tissue analysis data associated with one or more prior medical procedures; accessing surgical plan data associated with the one or more prior medical procedures; comparing, according to pre-selected similarity criteria, the tissue identification data and the archival tissue analysis data associated with the one or more prior medical procedures; identifying one or more similar prior medical procedures having archival tissue analysis data satisfying the pre-selected similarity criteria; and processing the surgical plan data associated with the one or more similar prior medical procedures to generate one or more steps of a suggested surgical plan; and communicating the one or more steps of the suggested surgical plan.

In another aspect, a computer implemented method of correlating a preoperative surgical plan with archival surgical plan data from one or more prior medical procedures is provided, the method comprising: obtaining preoperative surgical plan data associated with a medical procedure to be performed on a subject; accessing outcome data associated with one or more prior medical procedures; accessing archival surgical plan data employed during the one or more prior medical procedures; comparing, according to pre-selected similarity criteria, the preoperative surgical plan data and the archival surgical plan data associated with the one or more prior medical procedures; identifying one or more similar prior medical procedures having archival surgical plan data satisfying the pre-selected similarity criteria; and providing outcome data associated with the one or more similar prior medical procedures.

In another aspect, a system for correlating a preoperative surgical plan with archival surgical plan data from one or more prior medical procedures is provided, the system comprising: a control and processing system comprising one or more processors and memory coupled to said one or more processors, said memory storing instructions, which, when executed by said one or more processors, causes said one or more processors to perform operations comprising: obtaining preoperative surgical plan data associated with a medical procedure to be performed on a subject; accessing outcome data associated with one or more prior medical procedures; accessing archival surgical plan data employed during the one or more prior medical procedures; comparing, according to pre-selected similarity criteria, the preoperative surgical plan data and the archival surgical plan data associated with the one or more prior medical procedures; identifying one or more similar prior medical procedures having archival surgical plan data satisfying the pre-selected similarity criteria; and providing outcome data associated with the one or more similar prior medical procedures.

In another aspect, method of performing tissue analyses while performing a tissue resection procedure on a subject is provided, the method comprising: during a tissue resection procedure, performing, with a spatially tracked local tissue analysis device, a plurality of local tissue analyses, such that different local tissue analyses correspond to different tissue locations that are exposed during the resection procedure; employing tracking data associated with the spatially tracked local tissue analysis device to determine, in a reference frame spatially registered to a medical image of the subject, the location data corresponding to each local tissue analysis; recording local tissue diagnostic data from each local tissue analysis in association with its corresponding location data; constructing a spatial profile of the resected tissue by correlating the local tissue diagnostic data with the location data.

In another aspect, a method of performing intraoperative tissue analysis while performing a tissue resection procedure on a subject is provided, the method comprising: during a tissue resection procedure: performing a local ex-vivo diagnostic measurement on a biopsy sample of a tumor, thereby obtaining a reference measurement associated with tumor tissue; and during subsequent tissue resection: intermittently performing local in-vivo diagnostic measurements on exposed tissue; and comparing the reference measurement to each in-vivo measurement to identify the presence or absence of tumor tissue in the exposed tissue.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
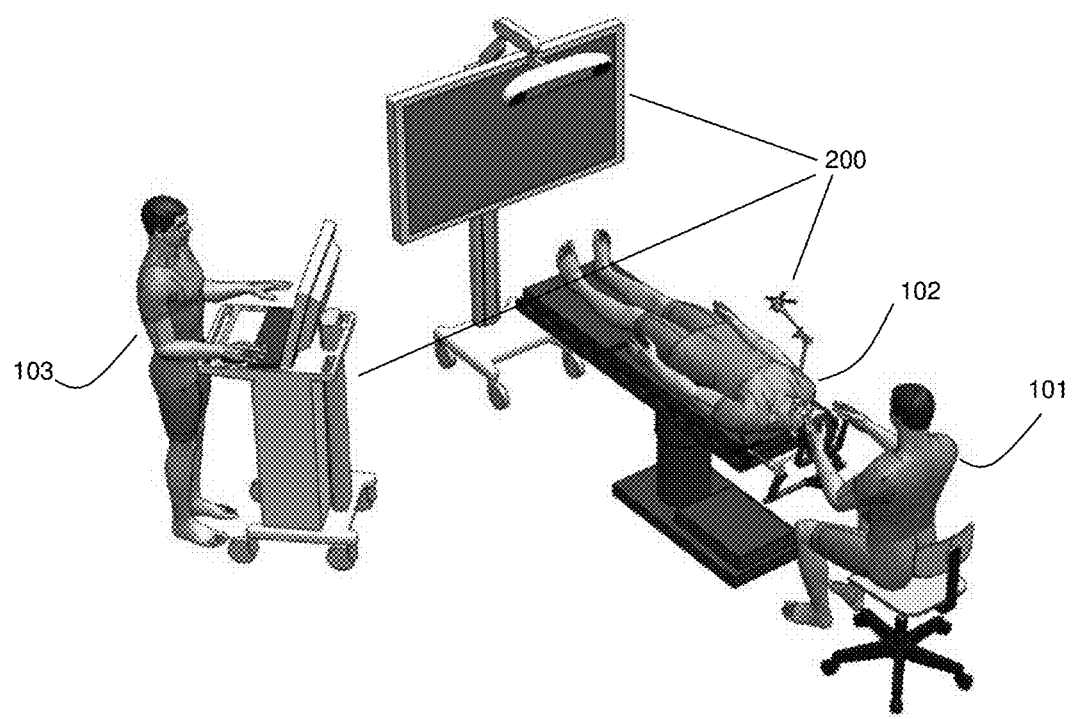
FIG. 1 is a diagram illustrating an exemplary navigation system to support minimally invasive access port-based surgery.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrase "medical instrument" refers to a tool, instrument, or other implement employed during a medical procedure. A medical instrument may be provided in various forms, such as, but not limited to, a handheld or robotically positioned tool, or a component that is attached to, or inserted into, a subject during a surgical or medical procedure. Non-limiting examples of medical instruments include, but are not limited to, scalpels, bi-polar devices, suction devices, cutting devices, clamping devices, access ports, and forceps.

As used herein, the phrase "operator" refers to a user, medical practitioner, surgeon, imaging technician, or other individual or group of individuals involved in operating medical instruments, devices and equipment during a medical procedure.

As used herein, the phrase "tracking system" refers to a system configured to track the position and/or orientation of one or more objects, such as locations of a subject and/or surgical instruments. In some embodiments, the tracking system may be configured to track the position and/or orientation of an imaging device (such as an optical camera). A tracking system may also be employed to track the position and/or orientation of an access port or other component that is attached to, or inserted into, a subject or subject. In one example, a tracking system may employ a pair of infrared cameras to track the position and orientation of active or passive infrared spheres (fiducials) attached to one or more objects, such as the Polaris® system from NDI.

As used herein, the phrase "navigation system" refers to a system that processes and spatially registers preoperative image data to an intraoperative reference frame, and displays the position and orientation of one or more tracked items relative to the preoperative image data. A navigation system may interface with, or include, a tracking system, in order to track the items. In some example implementations, hardware associated with the navigation system may include a computer system, a display, and a tracking system.

As used herein, the phrase "phase of the medical procedure" refers to a given step, or set of sequential steps, within a medical procedure. In another example, a phase of a medical procedure need not be a given step or set of sequential steps in a procedure, but may relate to the use of a specific tool or set of tools within a given step of a medical procedure.

As used herein, the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

As used herein, the phrase "access port" refers to a cannula, conduit, sheath, port, tube, or other structure that may be inserted into a subject in order to provide access to internal tissue, organs, or other biological substances. In some embodiments an access port may directly expose internal tissue, for example via an opening or aperture at a distal end thereof, and/or via an opening or aperture at an intermediate location along a length thereof. In other embodiments an access port may provide indirect access, via one or more surfaces that are transparent, or partially transparent, to one or more forms of energy or radiation, such as, but not limited to, electromagnetic waves and acoustic waves.

As used herein, the phrase "local tissue analysis" refers to an action taken to, or event associated with, the local analysis of tissue during, and optionally after, a medical procedure. In one example, a local tissue analysis may involve obtaining a biopsy sample during a medical procedure, and performing an analysis on the biopsy sample either intraoperatively or postoperatively. In another example, a local tissue analysis may involve obtaining a diagnostic measurement of a local region (e.g. a subset of a region associated with a medical image, or a subset of an anatomic region within a subject). Understood is that a local tissue analysis involving a diagnostic measurement may be performed to obtain one or more spot or point measurements (optionally combining a plurality of local spot or point measurements to construct an image) or an image of a local tissue region.

As used herein, the phrase "tissue analysis data" refers to data obtained after having performed a local tissue analysis. For example, in the case in which a local tissue analysis is performed as a biopsy with postoperative analysis, the tissue analysis data may be measurements (e.g. cell morphology, cell type, microscopy images, etc.) obtained when performing the analysis of the biopsy sample. In the case in which a local tissue analysis is performed to obtain a local diagnostic image, the tissue analysis data may include the local image data. Non-limiting examples of local diagnostic images include, for example, a white light image, a hyperspectral image, a polarization-sensitive image, an optical coherence tomography image, an ultrasound image, and a magnetic resonance imaging image. In another non-limiting example, in the case when a local tissue analysis if performed to obtain a spot or point measurement within a region of interest, the local tissue analysis data may be a spectrum, such as a Raman spectrum or an optical spectrum.

As used herein, the phrase "local", when used in association with a diagnostic measurement, refers to a diagnostic measurement obtained at or near a tissue of region of interest. For example, a local diagnostic measurement may be made with a local diagnostic non-imaging device, such as a Raman probe, or with a local diagnostic imaging device, such as an exoscope or magnetic resonance imaging probe. A local diagnostic measurement has a location associated therewith, where the location may be shown in a regional or global image of a subject. The phrase "regional", when used in association with a diagnostic image, refers to an image including both a tissue region of interest, and other surrounding tissue structure.

As used herein, the phrase "diagnosis data" refers to data or information associated with the diagnosis of a medical condition, such as a type of tumor or a stage of a tumor. Diagnosis data may be based on, or include, pathology data.

As used herein, the phrase "pathology data" refers to information associated with pathology testing of a tissue sample. Pathology data may include a pathology report. In another non-limiting example, pathology data may include information associated with one or more pathological tissue types identified from the local tissue analysis such as, but not limited to, tumor type, tumor stage, tumor size, and tumor cell information.

As used herein, the phrase "subject" refers to human or non-human subjects or patients.

Some example embodiments of the present disclosure provide methods and systems that involve the integration of imaging and tissue analysis. In some example embodiments a combination of regional, and local imaging, and tissue biopsy or local analysis, may be employed to inform decision making and treatment selection during or after a medical procedure. Some example embodiments described below provide systems and methods for integrating and updating preoperative and intraoperative plans based on prior medical procedures having, for example, similar local tissue analysis data, similar pathology data, and/or similar surgical plans.

In some example embodiments described below, systems and methods are provided in which three-dimensional positions (between or within subjects) associated with local tissue analyses (e.g. biopsy or in-vivo measurements) are associated with preoperative or intraoperative images, and/ or with information associated with prior tissue analyses, such as prior outcomes (e.g. subject outcomes and/or economic outcomes), archival tissue analysis, and/or pathology data (which may be stored in an electronic data base including subject information). Furthermore, in some embodiments information recorded during previous medical procedures may be employed to assist with the performing or planning of a medical procedure.

Figure 2:
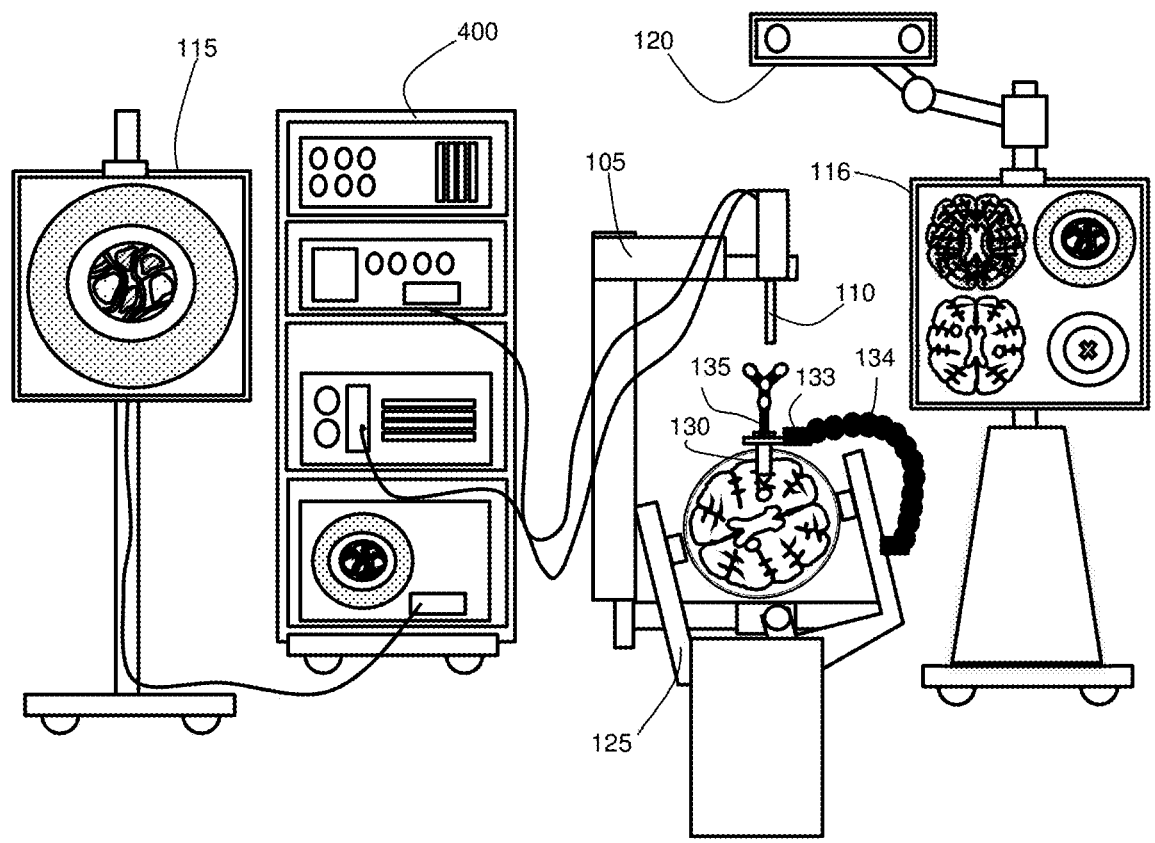
FIG. 2 is a diagram illustrating various components of system for performing image-guided port based medical procedures.

While many of the examples and illustrations provided in the present disclosure relate to minimally invasive neurological procedures, such as procedures involve resection of brain tumors, understood is that the scope of the present disclosure is intended to include and be applicable to, a wide range of medical procedures as further described below.
Example Minimally Invasive System for Performing Image-Guided Medical Procedure FIGS. 1 and 2 illustrate an example automated system for performing various embodiments of the present disclosure, providing a non-limiting example pertaining to a computer-assisted minimally-invasive neurological surgical procedure employing an access port. FIG. 1 illustrates a perspective view of a minimally invasive port based surgical procedure. Surgeon 101 conducts a minimally invasive access port-based surgery on a subject 102 in an operating room (OR) environment. An automated system including an equipment tower, cameras, displays, and tracked instruments assists surgeon 101 during the medical procedure. One or more operators 103 may also present to operate, control and provide assistance for the one or more aspects of the system.

FIG. 2 illustrates various example components of an automated system for assisting a medical procedure involving an access port. The system includes one or more imaging devices (for example, volumetric, whole organ, regional, point, or tool based), surgical guidance devices, software systems, databases, tissue specimen handling devices, and tracked medical instruments (e.g. surgical tools) as an integrated system. As described in various example embodiments below, the system may be configured to correlate three-dimensional positions on or within subjects with pathology samples, preoperative or intraoperative images (volumetric, regional, point or tool based), and patient and economic outcomes, and an electronic data base of patient information.

The example automated system includes an automated robotic arm 105, which supports an optical video scope 110 (and associated illumination), video display 115 for displaying a video image from optical video scope 110, navigation display 116 for providing a navigation user interface, a tracking device 120 for tracking various medical instruments within the surgical field, and a control and processing unit 400 for controlling various devices (such as the robotic arm 105) and providing surgical navigation. A secondary display may provide output of the tracking device 120. The output may be shown in axial, sagittal and coronal views as part of a multi-view display.

The example embodiment shown illustrates control and processing system 400 as residing in an equipment tower in a single tower configuration, connected to dual displays 115 and 116. However, understood is that other configurations may alternatively be employed (for example, a dual tower configuration and/or a single display configuration). Furthermore, an equipment tower may also be configured with a UPS (universal power supply) to provide for emergency power, in addition to a regular AC adapter power supply.

As described in detail below, in some embodiments, control and processing system 400 may include, or may be interfaced with, one or more recording devices or software modules that provide real-time recording of one or more aspects of the medical procedure. For example, the system may be configured to capture one or more of audio, video, sensory and multi-modal (e.g. CT, MR, US, etc.) inputs from different sources. All relevant data may be received via one or more recording devices (for example, stored in the equipment tower) and stored in memory by a recording module. The one or more aspects of the medical procedure may be automatically recorded from the outset of the procedure, or may be controlled by an operator and/or administrator. In other embodiments, the procedure may be automatically recorded (by default), but there may be an option to override or delete the recording during the medical procedure or after the medical procedure has been completed.

Referring again to FIG. 2, a subject's head is held in place by a head holder 125, and inserted into the head is an access port 130 and introducer 135 (having fiducial markers attached thereto). Introducer 135 is shown received within access port 130 in the figure, and is tracked using tracking system 120. A guide clamp 133 for holding access port 130 may be provided. Guide clamp 133 can optionally engage and disengage with access port 130 without needing to remove the access port from the subject. In some embodiments, access port 130 can slide up and down within clamp 133 while in the closed position. A locking mechanism may be attached to or integrated with guide clamp 133, and can optionally be actuated with one hand, as described further below.

Articulated arm 134 may be provided with an attachment point to hold guide clamp 133. Articulated arm 134 may have up to six degrees of freedom to position guide clamp 133. Articulated arm 134 may be attached or attachable to a point based on subject head holder 125, or another suitable subject support, to ensure when locked in place, guide clamp 133 cannot move relative to the subject's head. The interface between guide clamp 133 and articulated arm 134 may be flexible, or optionally locked into place. Flexibility is desired so the access port can be moved into various positions within the brain, but still rotate about a fixed point.

An example of such a linkage that can achieve this function is a slender bar or rod. When access port 130 is moved to various positions, the bar or rod will oppose such a bend, and move the access port 130 back to the centered position. Furthermore, an optional collar may be attached to the linkage between the articulated arm, and the access port guide, such that when engaged, the linkage becomes rigid. Currently, no such mechanisms exist to enable positioning access port 130 in such a manner.

The position of the subject may be initially determined and/or continuously tracked intraoperatively by tracking system 120. A set of preoperative images associated with the anatomy of interest of the subject may be obtained prior to surgery. These images may be intraoperatively registered to the subject, for example, by way of surface matching, sets of known touch points (e.g., tip of nose, temple, and ears) and/or fiduciary markings that can be identified on the subject and in the associated images. These points or surfaces are registered to the tracking coordinate frame through a defined registration process. Once registered, medical instruments, and the associated subject images can be tracked in real-time, and shown in various manners on a computer monitor.

The example automated system illustrated in FIG. 2 is configured for the application of minimally invasive brain surgery, using an access port to provide a conduit within the head, allowing access to internal brain tissue for surgical, therapeutic, or diagnostic applications. The figure shows an intracranial access port which may be employed in neurological procedures in order to provide access to internal tissue pathologies, such as tumors. One example of an intracranial access port is the BrainPath™ surgical access port provided by NICO, which may be inserted into the brain via an obturator (introducer) with an atraumatic tip. Such an access port may be employed during a surgical procedure, by inserting the access port via the obturator that is received within the access port to access an internal surgical site.

Figure 3:
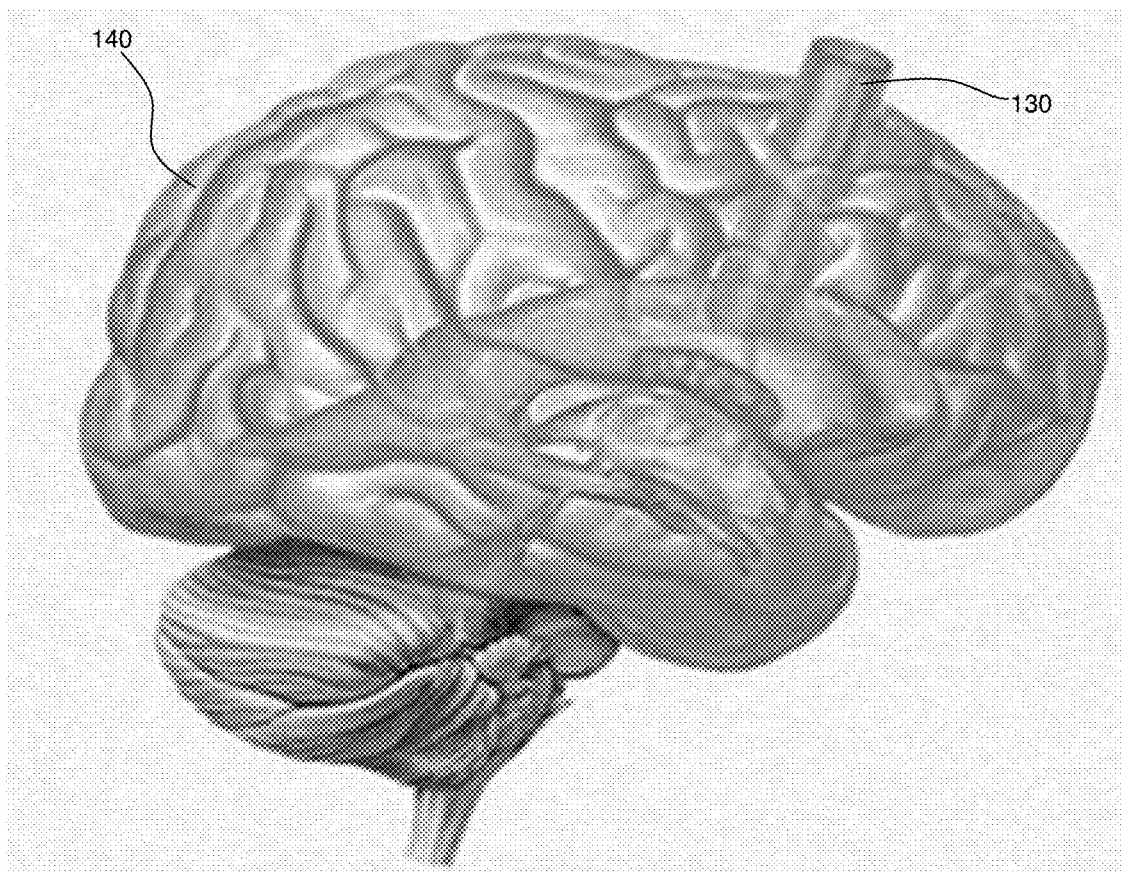
FIG. 3 is a diagram illustrating a human brain into which an access port has been inserted, establishing an open conduit for providing access to tissue within the brain.

FIG. 3 illustrates the use of an access port, showing a human brain 140 into which an access port 130 has been inserted, thereby establishing an open conduit providing access to tissue deep within the brain. Surgical instruments may then be inserted within the lumen of the access port in order to perform surgical, diagnostic or therapeutic procedures, such as resecting tumors as necessary. This approach allows a surgeon, or robotic surgical system, to perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue. For example, access port based procedures may be employed for other surgical interventions for other anatomical regions such as, but not limited to, spine, knee, and any other region of the body that will benefit from the use of an access port or small orifice to access the interior of the human body.

Referring again to FIG. 2, in order to introduce the access port 130 into the brain, introducer 135 with an atraumatic tip may be positioned within the access port and employed to position the access portion within the head. As noted above, introducer 135 (or access port 130) may include fiducials for tracking. These fiducials may be passive or active fiducials, such as reflective spheres for passive infrared detection via an optical camera, or, for example, pick-up coils in the case of an electromagnetic tracking system. The fiducials are detected by tracking system 120 and their respective positions are inferred by tracking software (which may reside within tracking system 120, or may reside, for example, within control and processing unit 400).

Once access port 130 is inserted into the brain, introducer 135 may be removed to allow for access to the tissue through the central opening of access port 130. However, once introducer 135 is removed, access port 130 can no longer be directly tracked in real time (according to the example embodiment shown in FIG. 2 in which no fiducials are attached to access port 130). In order to track the position and orientation of access port 130, it may be indirectly and intermittently tracked by a pointer tool having fiducials that are detectable by tracking system 120.

Although the example system described in FIGS. 1 and 2 relates to a neurosurgical procedure, understood is that the systems and methods described herein are not intended to be limited to neurosurgical procedures or port-based procedures, and may be employed for a wide range of medical procedures. Examples of other types of medical procedures including orthopedic, trauma, gastrological, cardiac, gynecological, abdominal, otolaryngology (or ENT—ear, nose, throat conditions), spinal, thoracic, oral and maxillofacial, urological, dental, and other surgical, diagnostic or therapeutic medical procedures. It is further noted that while many of the example embodiments described herein employ external imaging, such as imaging with an external video scope, understood is that various internal imaging devices, such as endoscopic or catheter imaging devices, may additionally or alternatively be employed. Noted is that embodiments of the present disclosure may be employed within or adapted to procedures employing telesurgical or shared-control systems.

In many of the example embodiments described below, each medical instrument that is to be tracked may have a fiducial attached thereto (e.g. passive or active fiducial markers, such as reflective spheres or active LED lighting emitted from at least 3 points on a device) so that the position and orientation of the instrument can be determined. In one example implementation, the fiducial markers may be employed to determine a reference position on medical instrument (such as a central point), and an axis of the medical instrument (such as a longitudinal axis of a tool).

Example Methods of Performing Access Port Based Medical Procedure

Figure 4A:
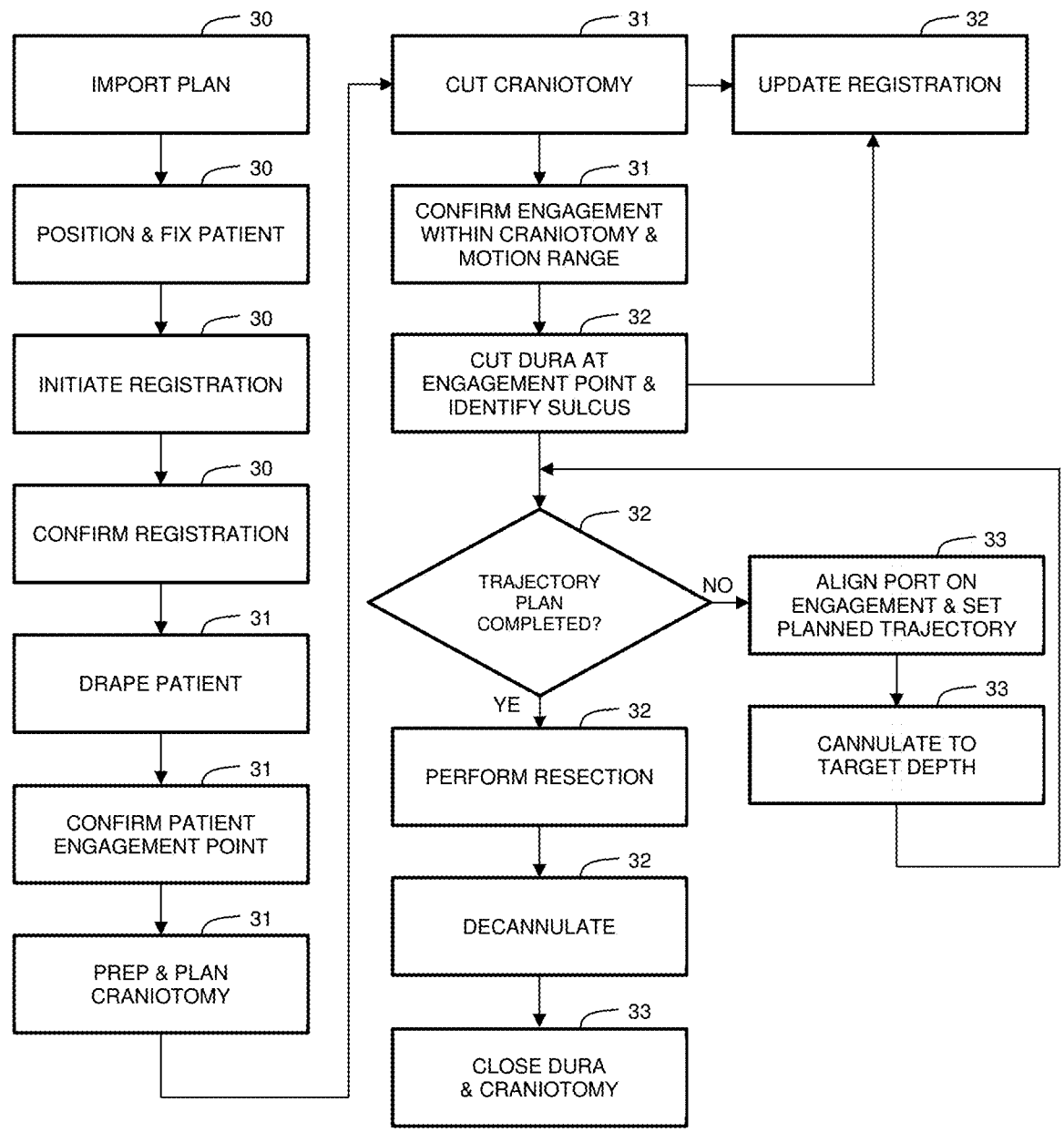
FIG. 4A is a flow chart illustrating the processing steps involved in a port-based surgical procedure using a navigation system.

FIG. 4A is a flow chart illustrating the processing steps involved in an example port-based surgical procedure using a navigation system. The first step involves importing the port-based surgical plan (step 302). A detailed description of the process to create and select a surgical plan is outlined in the disclosure "PLANNING, NAVIGATION AND SIMULATION SYSTEMS AND METHODS FOR MINIMALLY INVASIVE THERAPY," a United States Patent Publication based on a United States Patent Application, which claims priority to U.S. Provisional Patent Application Ser. Nos. 61/800,155 and 61/924,993, which are both hereby incorporated by reference in their entirety.

As outlined above, an example surgical plan may include preoperative 3D imaging data (e.g., MRI, ultrasound, etc.) overlaid with inputs (e.g., sulcal entry points, target locations, surgical outcome criteria, and additional 3D image data information) and displaying one or more trajectory paths based on the calculated score for a projected surgical path. Understood is that the present example embodiment is provided merely as an illustrative example plan, and that other surgical plans and/or methods may also be employed without departing from the scope of the present disclosure.

Once the plan has been imported into the navigation system in step 302, the subject is affixed into position using a head or body holding mechanism. The head position is also confirmed with the subject plan using the navigation software, as shown in step 304.

Registration of the subject is then initiated in step 306. The phrase "registration" or "image registration" refers to the process of transforming sets of data into a common coordinate system. Registered data may be provided in the form of multiple images, data from different sensors, times, depths, or viewpoints. The process of registration is employed in the present application for medical imaging in which images from different imaging modalities are co-registered.

Appreciated is that there are numerous registration techniques available and one or more of them may be employed according to the embodiments of the present disclosure. Non-limiting examples of registration methods include intensity-based methods which compare intensity patterns in images via correlation metrics, while feature-based methods find correspondence between image features such as points, lines, and contours. Image registration algorithms may also be classified according to the transformation models they use to relate the target image space to the reference image space. Another classification can be made between single-modality and multi-modality methods. Single-modality methods typically register images in the same modality acquired by the same scanner/sensor type, for example, a series of CT images can be co-registered, while multi-modality registration methods are used to register images acquired by different scanner/sensor types or pulse sequences, for example in MRI and PET. Multi-modality registration methods are often used in medical imaging of the head/brain, as images of a subject are frequently obtained from different scanners. Examples include registration of brain CT/MRI images or PET/CT images for tumor localization, registration of contrast-enhanced CT images against non-contrast-enhanced CT images, and registration of ultrasound and CT.

Figure 4B:
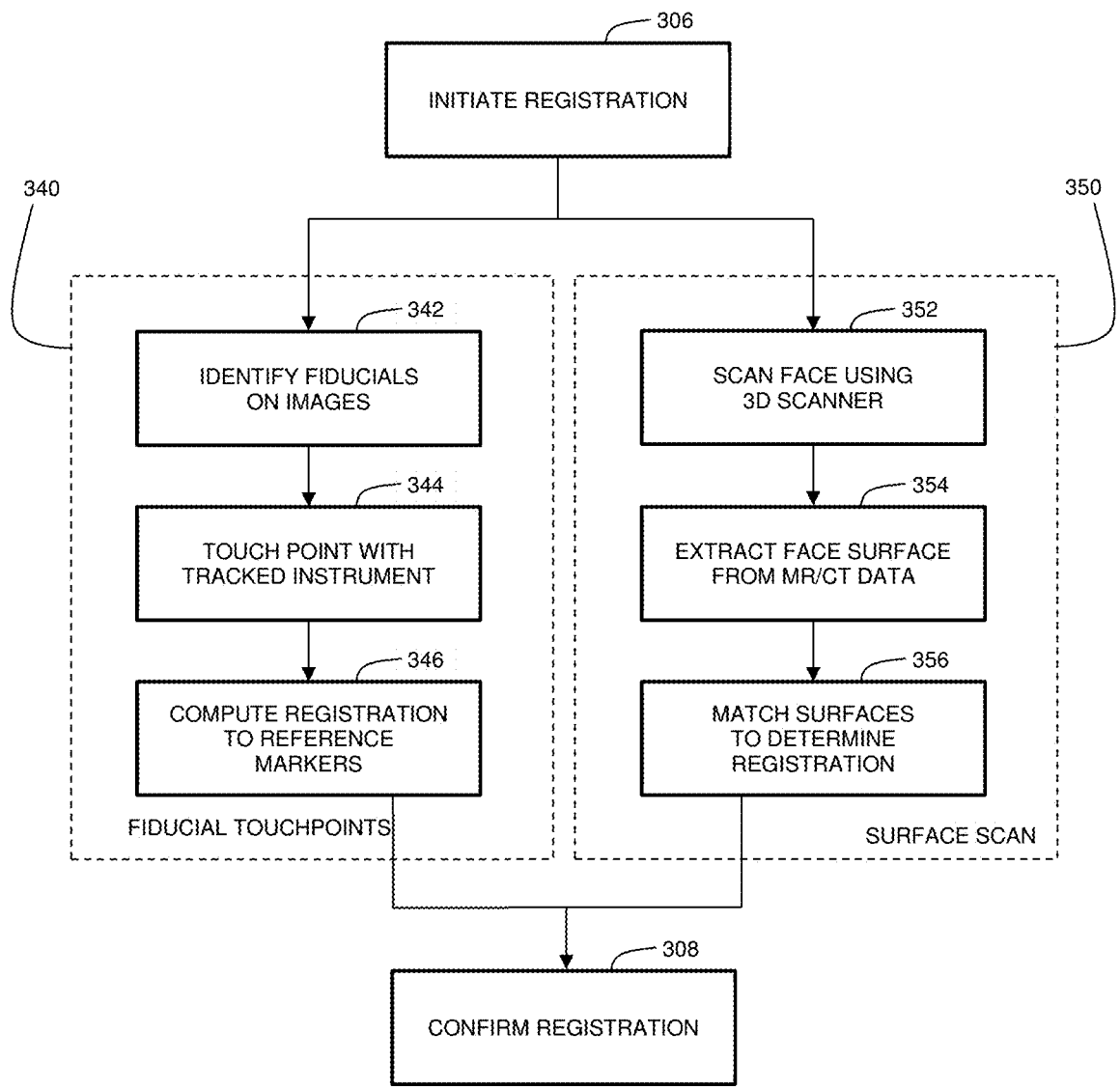
FIG. 4B is a flow chart illustrating the processing steps involved registering a patient to an intraoperative reference frame.

FIG. 4B is a flow chart illustrating the further processing steps involved in registration as outlined in FIG. 4A. In one example implementation, the method may employ fiducial touchpoints as shown at 340. In such a case, the process involves first identifying fiducials on images at step 342, then touching the touchpoints with a tracked instrument (step 344). Next, the navigation system computes the registration to reference markers (step 346).

In another example implementation, registration can be performed by conducting a surface scan procedure, as shown at 350. The first step involves scanning a portion of the body (e.g., the face) using a 3D scanner (step 352). The face surface is then extracted from the MR/CT data (step 354). Finally, surfaces are matched to determine registration datapoints. Upon completion of either the fiducial touchpoint 340 or surface scan 350 procedures, the data extracted is computed and used to confirm registration, as shown in step 308.

In another example implementation, recovery of loss of registration may be provided. For example, during a medical procedure, a handheld medical instrument may be tracked using a tracking system, and a representation of the instrument's position and orientation may be provided and displayed as an overlay on a previously acquired or current image (such as a three-dimensional scan) of a subject's anatomy obtained with an imaging device or system (such as ultrasound, CT or MRI).

To achieve such an image overlay, a registration is needed between the coordinate frame of a tracking system, the physical location of the subject in space, and the coordinate frame of the corresponding image of the subject. This registration is typically obtained relative to a tracked reference marker, which is placed in a fixed position relative to the patient anatomy of interest and thus can be used as a fixed reference for the anatomy. Generally this can be accomplished by attaching the reference to a patient immobilization frame (such as a clamp for skull fixation in neurosurgery), which itself is rigidly attached to the subject (for example, as shown in FIG. 2).

However, the reference may be held to the frame, for example, through an arm, which can be bumped and accidentally moved, which creates a loss of registration. Additionally, since the reference marker must be positioned so that it is visible by the navigation hardware (typically requiring line-of-sight for optical tracking, or otherwise within the observation or communication field of the tracking system), this tends to position the reference such that it is in the open thus more susceptible to accidental interaction and loss of registration. In situations of lost registration, a surgical procedure tends to be stopped while a new registration is computed, although this may not always be possible if, for example, the registration fiducial points or patient skin surface are no longer accessible due to the progression of the surgical procedure, and thus creating a need for a full re-registration or, in some cases even disabling navigation for the remainder of the procedure.

Referring again to FIG. 4A, once registration is confirmed in step 308, the subject is draped (step 310). Typically, draping involves covering the subject and surrounding areas with a sterile barrier to create and maintain a sterile field during the surgical procedure. The purpose of draping is to eliminate the passage of microorganisms between non-sterile and sterile areas. Upon completion of draping (step 310), the patient engagement points are confirmed at step 312, and craniotomy is then prepared and planned (step 314).

Upon completion of the prep and planning of the craniotomy (step 312), the craniotomy is then cut, where a bone flap is temporarily removed from the skull to access the brain (step 316). Registration data is updated with the navigation system at this point (step 322). The engagement within craniotomy and the motion range is then confirmed in step 318. Once this data is confirmed, the procedure advances to the next step of cutting the dura at the engagement points and identifying the sulcus (step 320). Registration data is also updated with the navigation system at this point (step 322).

In one example embodiment, by focusing the camera's gaze on the surgical area of interest, this registration update can be manipulated to ensure the best match for that region, while ignoring any non-uniform tissue deformation affecting areas outside of the surgical field (of interest). Additionally, by matching overlay representations of tissue with an actual view of the tissue of interest, the particular tissue representation can be matched to the video image, and thus tending to ensure registration of the tissue of interest.

For example, in one example implementation, a video image may be provided in which a post-craniotomy real-time intraoperative optical image of the brain surface (i.e. exposed brain) is provided with an overlay of the preoperative (and registered) sulcal map, and the registration may be corrected by providing input manipulating aligning the preoperative sulcal map with the sulcal profile that is observable in the real-time intraoperative image.

In another example implementation, a video image may be provided in which a post-craniotomy real-time intraoperative optical image of the exposed vessels on the brain surface (i.e. exposed brain) is provided with an overlay of preoperative image of vessels (obtained via image segmentation of preoperative image data, co-registered with intraoperative position), and the registration may be corrected by providing input manipulating aligning the preoperative vessels with the exposed vessels that are observable in the real-time intraoperative image.

In another example implementation, a video image may be provided in which a post-craniotomy real-time intraoperative optical image of an exposed tumor (i.e. exposed brain) is provided with an overlay of a preoperative (and registered) image of the tumor (obtained via image segmentation of preoperative image data), and the registration may be corrected by providing input manipulating aligning the preoperative tumor image with the exposed tumor that are observable in the real-time intraoperative image.

In another example implementation, a video image may be provided in which a real-time intraoperative optical image of a nasal cavity is provided with an overlay of a preoperative (and registered) image of bone rendering of the bone surface (obtained via image segmentation of preoperative image data), and the registration may be corrected by providing input manipulating aligning the preoperative bone image with the bone surface that is observable in the real-time intraoperative image.

In other embodiments, multiple cameras can be used and overlaid with tracked instrument(s) views, and thus allowing multiple views of the data and overlays to be presented at the same time, which can provide even greater confidence in a registration, or correction in more than dimensions/views.

Thereafter, the cannulation process is initiated, as shown at step 324. Cannulation involves inserting a port into the brain, typically along a sulcal path as identified in step 320, along a trajectory plan. Cannulation is an iterative process that involves repeating the steps of aligning the port on engagement and setting the planned trajectory (step 332) and then cannulating to the target depth (step 334) until the complete trajectory plan is executed (step 324).

The surgeon then performs resection (step 326) to remove part of the brain and/or tumor of interest. The surgeon then decannulates (step 328) by removing the port and any tracking instruments from the brain. Finally, the surgeon closes the dura and completes the craniotomy (step 330).

Example Implementation of Control and Processing Unit

Figure 5:
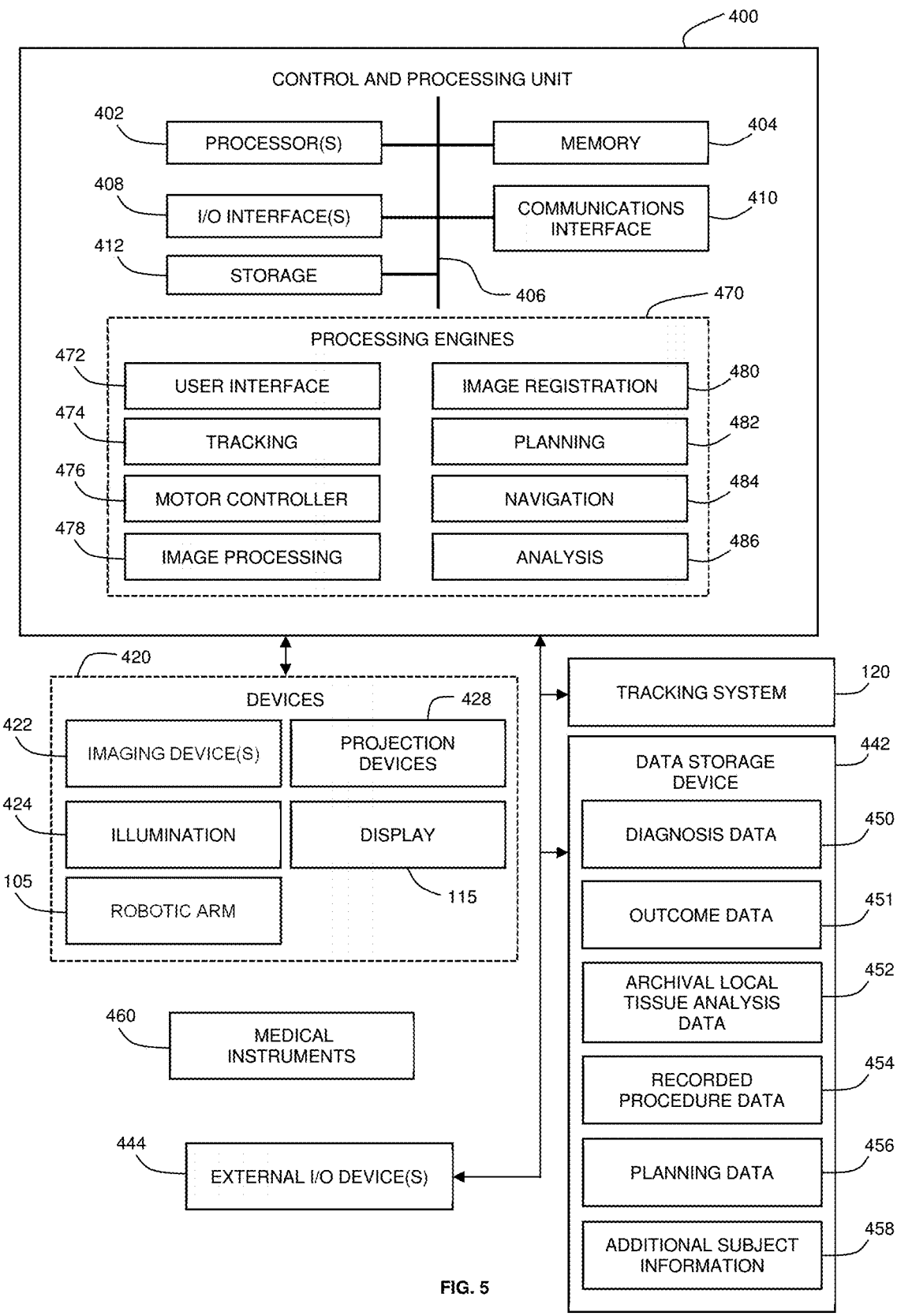
FIG. 5 is a diagram illustrating an example implementation of computer control system for implementing the various methods disclosed herein.

Referring now to FIG. 5, a block diagram of an example system configuration is shown. The example system includes control and processing unit 400 and a number of external components, shown below.

As shown in the FIG. 5, in one embodiment, control and processing unit 400 may include one or more processors 402, a memory 404, a system bus 406, one or more input/output interfaces 408, and a communications interface 410, and storage device 412. Storage device 412 may be employed to store information associated with a medical procedure, such as, but not limited to, local tissue analysis data, surgical plan data, pathology data, and recorded time-dependent medical procedure data.

Control and processing unit 400 is interfaced with other external devices, such as tracking system 120, data storage 442, and external user input and output devices 444, which may include, for example, one or more of a display, keyboard, mouse, foot pedal, microphone and speaker. Data storage 442 may be any suitable data storage device, such as a local or remote computing device (e.g. a computer, hard drive, digital media device, or server) having a database stored thereon.

In the example shown in FIG. 5, data storage device 442 may include archival information associated with prior tissue analyses, and control and processing unit 400 may be programmed to process such information to perform one or more of the methods described below. As shown in the example implementation illustrated in FIG. 8, data storage device 442 may include the following examples of information associated with a prior tissue analyses: diagnosis data 450, outcome data 451, archival local tissue analysis data 452, recorded time-dependent medical procedure data 454, planning data 456 (e.g. a surgical plan having been followed during a medical procedure including a local tissue analysis), and additional information associated with subjects associated with the prior tissue analyses, such as, but not limited to, demographic, prognostic, prior history, and/or genetic information. Although data storage device 442 is shown as a single device in FIG. 5, understood is that in other embodiments, data storage device 442 may be provided as multiple storage devices.

Medical instruments 460, such as a tissue resection device (for example, the Myriad tissue resection device manufactured by NICO), a biopsy device, or a local diagnostic measurement device (e.g. point-based or imaging based), are identifiable by control and processing unit 400. Medical instruments 460 may be connected to, and controlled by, control and processing unit 400, or may be operated or otherwise employed independent of control and processing unit 400. Tracking system 120 may be employed to track one or more of medical instruments 460 and spatially register the one or more tracked medical instruments to an intraoperative reference frame.

Control and processing unit 400 is also interfaced with a number of configurable devices that may be tracked by tracking system. Examples of devices 420, as shown in the figure, include one or more imaging devices 422, one or more illumination devices 424, robotic arm 105, one or more projection devices 428, and one or more displays 115. The one or more imaging devices 422 may include one or more local diagnostic measurement devices (e.g. point-based or imaging based). Tracking system 120 may be employed to track one or more of devices 422 and spatially register them to an intraoperative reference frame.

Embodiments of the disclosure can be implemented via processor(s) 402 and/or memory 404. For example, the functionalities described herein can be partially implemented via hardware logic in processor 402 and partially using the instructions stored in memory 404, as one or more processing engines 470. Example processing engines include, but are not limited to, user interface engine 472, tracking engine 474, motor controller 476, image processing engine 478, image registration engine 480, procedure planning engine 482, navigation engine 484.

As described in detail below, one or more processing engines may be provided for process information associated with prior tissue analyses, and such engines are represented by analysis engine 486. For example, in some embodiments, an analysis engine is provided to evaluate similarity criteria between of one or more local tissue analyses performed on a subject, and prior local tissue analyses stored in data storage device 442, or otherwise accessible, such as through an external network. Examples of such methods are described in the forthcoming description and accompanying flow charts. As described in detail below, similarity criteria may involve the evaluation of one or more metrics associated with one or more local tissue analyses performed on a subject, and one or more prior local tissue analyses, where the prior local tissue analyses may be associated with the medical history of the subject and/or a collection of other subjects.

In some example embodiments, the processing engines may be employed to perform methods including, but not limited to, tracking 3D position and orientation data for the purpose of spatially registering diagnostic devices capable of performing local diagnostic measurements (e.g. point based or imaging measurements); tracking locations of biopsy specimens to maintain 3D position and imaging information; recording biopsy sampling locations relative to the timing of the biopsy; recording surgical tool, and imaging device positions and actuation throughout a medical procedure; determining and recording margin boundaries in a tissue of interest in a virtual manner; locating regions on a 3D image and correlating pathology information to such regions; and characterizing tissue based on one or more tissue metrics, and employing such metrics to search a database including prior tissue analysis data, and ranking results based on a variable weighted metric based algorithm.

Understood is that the system is not intended to be limited to the components shown in the FIG. 5. One or more components control and processing 400 may be provided as an external component or device. In one alternative embodiment, navigation module 484 may be provided as an external navigation system that is integrated with control and processing unit 400.

Some embodiments may be implemented using processor 402 without additional instructions stored in memory 404. Some embodiments may be implemented using the instructions stored in memory 404 for execution by one or more general purpose microprocessors. Thus, the disclosure is not limited to a specific configuration of hardware and/or software.

While some embodiments can be implemented in fully functioning computers and computer systems, various embodiments are capable of being distributed as a computing product in a variety of forms and are capable of being applied regardless of the particular type of machine or computer readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices.

Recording Time-Dependent Information Associated with a Medical Procedure

In some embodiments, the one or more events during a medical procedure may be temporally and spatially tracked, and this information can be logged. For example, if a tissue specimen is captured, the time at which is it captured can be recorded. This time can be correlated with location through the use of tracked tools in a navigation system (tracked using an optical approach, or an EM-based tracking system). The location information will correspond to intraoperative MRI or CT (or PET or SPECT). The pathology information (microscope images, local imaging) can be associated with the time-stamp to allow that information to be stored in an appropriate database. This database can be searchable by patient (to see how the same tissue looked under different modalities) or by disease type (to see how the same disease (validated by pathology) looks under different modalities), or by modality (to see what diseases are possible given a certain result (i.e. what possible tissues could have a given Raman spectra).

By tracking the movements and locations of all tools throughout the procedure, it is also possible to determine efficiencies in the operation—for example that the surgeon uses a particular tool for a very short or very long time, or that certain steps are less efficient than they could be. This information can be used by the surgeons and hospital administrators to properly estimate surgical times for optimum scheduling.

As noted in FIG. 5, one or more medical instruments 460 and devices 420 may be tracked using tracking system 120. Such instruments and/or devices may be tracked, for example, using fiducials markers. Fiducial markers may be passive or active fiducials, such as reflective spheres for passive infrared detection via an optical camera, or, for example, pick-up coils in the case of an electromagnetic tracking system. The fiducials are detected by tracking system 120 and their respective positions are inferred by tracking software (which may reside within tracking system 120, or may reside, for example, within control and processing unit 400. Such tracking allows the position and orientation of the instruments and/or devices to be determined and recorded. In one example implementation, the fiducial markers may be employed to determine a reference position on medical instrument or device, (such as a central point), and an axis of the medical instrument or device (such as a longitudinal axis of a tool).

In some embodiments, tracked position and orientation data associated with one or more instruments and/or devices is recorded during a medical procedure. For example, in one example embodiment, the time-dependent position and orientation, and optionally other state information or configuration parameters associated one or more instruments or devices is recorded. For example, information that may be recorded may include, but is not limited to, tip offset, tip deflection, the state of control buttons and status, accuracy of measurement, visibility to a tracking system, the identity of a tool that is being used as a registration reference, and/or a registration reference transform may be recorded and/or processed.

In one example implementation, any or all of the recorded information may be recorded, along with time data (e.g. transmitted to a recording device), at sequential time points, at particular time points, or only at time points for which the information to be recorded has changed relative to its previously recorded value.

In some example embodiments, a timestamp is associated with one or more, or all, of recorded information. Each timestamp may be matched to a global timestamp associated with other events recorded during the medical procedure, such as a global timestamp associated with video captures (such as during a surgery, or sub-procedures such as when a cauterizer was on, when cutting, when tissue pathology samples were obtained, or other procedures). Further data can be integrated from any source from which a timestamp can be matched, including audio streams, video streams, state information of any imaging displays (e.g. data set, hanging protocol, window level, position, orientation, etc.) or other events of interest (e.g. registration of biopsy samples, containers, results, etc.).

In one example embodiment, the time-dependent position and orientation of a medical instrument or device may be recorded as a vector relative to a fixed reference position (such as a patient fixed reference tool or a tracking camera centered on a coordinated frame). An orientation can be recorded, for example, as a quaternion or axes vectors, and deflection can be recorded as an offset, or another parameterized geometric representation (such as spline parameters).

In various embodiments, several parameters may be tracked and recorded at each time for an instrument, depending on the data of relevance and any assumptions made (or variables held constant).

In one example implementation, seven parameters may be recorded to represent the time-dependent position and orientation of a device or instrument. The six parameters are x, y, z, roll, pitch and yaw. The $7^{th}$ parameter being the time instance at which specific orientation information is recorded. In other example implementations, fewer parameters may be used, if one or more assumptions are made (if, for example, there is no desire to track or record a direction of rotation, such as an elongated instrument rotating around a longitudinal axis). More parameters can be used if the data is represented in other convenient ways, such as a 4×4 (16 parameter) transformation matrix in homogeneous coordinates, or a quaternion representation of rotations as an example. In other embodiments, fewer or more parameters may be tracked, as required or desired by the configuration for use.

The representation, transmission, receiving, recording, storing, and processing of information pertaining to a medical procedure as described herein may allow for efficient storage, communication, and processing of the state of tools and instruments involved in a procedure. For example, by storing such data as discrete data points pertaining to specific points in time, less storage space may be required than, for example, a video capture of a screen display of a navigation system and the storage of this information may enable other features and functions, as described below.

As noted above, in some example embodiments, one or more other time-stamped data streams, in addition or in alternative to a data stream recorded for a tracked instrument, may be recorded for subsequent playback and/or analysis.

In an example embodiment, once at least a portion of the time course of a procedure has been recorded as described herein, the spatial (position and orientation) data points and associated timestamps may be processed for subsequent analysis. For example, an analysis may be performed to determine, based on the retrospective data, one or more metrics associated with a procedure (such as surgical metrics). Examples of such metric include, but are not limited to, an amount of time that a tool or instrument was used, an amount of time that a tool or instrument spent at each depth of insertion, an amount of time that a tool or instrument spent near a certain feature (such as a vessel, nerve or lesion), and/or an extent of coverage of the various tools and instruments available during the procedure.

As noted above various aspects of a medical procedure may be recorded (e.g. in a database) in a seamless manner so that the surgeon or an operator can utilize the volume of data for future care of the same subject, other subjects, or training purposes. Data streams may include, but are not limited to, any or more of the following (or additional data streams): video streams; audio streams; location and position of all tracked instruments and items; the state of any imaging displays (data set, hanging protocol, window level, position, orientation, etc.; other events of interest (registration of biopsy samples, containers, results). This would enable the local or distributed playback, at some point in the future, the entire operative procedure in part or in whole. As noted above, one example implementation would be to allow the surgeon to "pause" the playback and then take control of the "paused" imaging displays and execute what-if scenarios for post-mortem analysis, audit, education, or training One would be able to assess how the surgical procedure would have proceeded if the approach was slightly different approach than was actually used during the recorded session. The playback could even proceed using a different display angle, different data sets, or other differences from the originally recorded procedure.

Alternatively, a paused playback point could be used as the starting point for a new simulation, where the current position and orientations of tracked items and states of displays become the starting point for virtual manipulation of both the instruments and the imaging displays. One could even record the progress of the simulation in the same way as a live procedure so that it can also be used for time shifted audit, analysis, and training Finally, several recorded simulations of different parts of one procedure could be made in different physical locations by different people, can be reviewed and analyzed at another location by a different team, and then the "best" parts of each simulation could be stitched together to provide a final "best" solution.

In some embodiments, a common source of time stamps for samples is provided at high enough resolution and low enough latency so that recording of samples of various stream can be effectively distributed during real time, and then later amalgamated.

In some example embodiments the data points and timestamps may be further processed to simulate intraoperative instrument/device motion. This simulation may be provided as a controllable replay. Unlike a video feed that is only viewable from the angle of recording, the present example embodiment permits the recreation and playback, of instrument/device motion through other angles by way of the recorded data points and timestamps. In other words, the viewpoint from which a simulation is rendered may be controllable by an operator.

Additionally, such an embodiment may be implemented to provide controls during playback, as if the instruments/devices were being manipulated live, which, when the system is associated with other imaging devices and systems, and/or spatially registered data from imaging devices and systems, permits slices and/or views of the image data to be visualized and manipulated in ways that are different than the ones used during the procedure. This embodiment may be employed to provide a more flexible, dynamic and/or controllable review of a procedure, rather than a straight static playback of a video recording of the procedure, which is limited to displaying only the image data that was recorded, from pre-set views, at the time of the procedure.

In one example implementation positions may be played back in real-time and also, for example, sped up, slowed down, paused, and searched. Additionally, an operator may recall some or all activities performed near a particular location in a spatially-constrained search function. Such an embodiment provides a "location aware" search function. For example, a 3D brain structure may be reconstructed using preoperative medical images such as MRI or CT. A user can then position a pointing device or a cursor at a specific anatomical position (e.g. the paracentral sulcus) and initiate a search. The search routine may query a database with previously recorded position and time information of each surgical tool and identify all instances where tip of a surgical tool was present in a predefined (and configurable) vicinity of the identified location. The location may be also identified using 3 orthogonal planar projections of the preoperative medical image, such as the multiplanar reconstruction image layout typically used by a radiologist. The position and associated time stamp information of the surgical tools may be alternatively stored as a sequential data structure. The query information (position information in this case) may be then used to search the list after sorting the data by position using any searching algorithm for sequential data.

In some embodiments, the positions and orientations of tracked intraoperative imaging devices and systems (such as, but not limited to, ultrasound probes, optical coherence tomography (OCT) probes, spectroscopy probes, intraoperative MRI coils, intraoperative CT, or fluoroscopy devices, and the like) can be correlated with the acquired images and analyzed in relation to other imaging data positioned and oriented to match the tools and instruments data points. If timestamps are available on the imaging devices/systems data, such timestamps can also be matched to the timestamps associated with the data points pertaining to the recorded position and orientation data for the instrument(s), so as to provide time-synchronized images and/or videos.

For example a hand-held ultrasound probe may be used shortly after craniotomy during brain tumor resection to identify presence of vasculature immediately below the dura. The position relative to the brain where the ultrasound image (typically, a B-mode scan) is obtained and time instance when the image is recorded may be captured. This recording, when synchronized with the time component of the 7 parameter time-dependent position and orientation information recording described previously, allows for exact association of intraoperative images with specific time points in the surgical procedure.

Such synchronized recording requires synchronization of a reference clock the time that is utilized by all recording systems in the room (OR). This can be achieved, for example, by configuring the recording devices to record the present time (e.g. a time referenced to UTC). Alternatively, if the recording devices are not recording standard time, they may be synchronized using a common server that provides time information to multiple clients, where one client may be a computer-based data acquisition systems used to record the position of surgical tools and another client may be a computer-based image acquisition system used to acquire ultrasonic images. Another client may be a computer-based system used to acquire intraoperative MRI. Similarly, other separate computer-based image and patient's physiological system monitoring systems may act as clients to a common time server. The server may be contacted by the clients at regular intervals to update the internal clock of each client. Hence, any drift in individual clocks of the clients can be adjusted. The end result is time synchronized recording of surgical tools, intraoperative physiological state of the patient (e.g. dissolved oxygen level) and intraoperative images.

This synchronized data may be valuable as a training tool, as well as to assess efficient use of surgical workflows and associated instrumentation. Such information associated with utilization of various tools and techniques in a particular surgical procedure may be analysed by health institutions to identify cost associated with surgical procedures and substantiate the charges communicated to insurance companies and other payers.

The preceding example embodiments may be employed for a variety of purposes. For example, the recorded information may be employed for review of a medical procedure, for a variety of purposes, including, not limited to, clinical, educational, legal, self-assessment, performance assessment, audit, retrospective determination of exact location of points of interest for subsequent imaging and follow-up assessment, and/or in-situ review of previous step(s) of a procedure during the conduct of the procedure, among others.

Furthermore, the preceding embodiments may be modified to allow an operator to "pause" the playback of a recorded procedure, and then take control of the "paused" imaging displays, and perform what-if scenarios for post-mortem analysis, audit, education, or training A paused playback point could thus be used as the starting point for a new simulation, where the current position and orientations of tracked items and states of displays become the starting point for virtual manipulation of both instruments and imaging displays. The progress of such a simulation can also be recorded in the same way as a live procedure so that it can also be used, for example, for time shifted audit, analysis, and training After having paused the playback of a recorded medical procedure, an operator may provide input specifying another angle, or may provide input such that the playback proceeds with different information displayed than was actually used during the recorded session. The playback may proceeds using a different display angle, different data sets, or other differences from the original recorded session.

In one example embodiment, both recordings and/or simulated video or visualization data from different parts of a medical procedure could be obtained or created in different physical locations by different people and in different sessions. These parts can be reviewed and analyzed at another location by a different team and the "best" parts of each simulation, as identified by a human, stitched together to provide a final "best solution" for future training purposes.

For example, in the case of brain tumor resection one surgeon may perform a real craniotomy and then acquire images using an ultrasound probe to identify the presence of sulcal folds or vasculature beneath the dura. The position of surgical tools and ultrasound scans will be recorded as the first data set, first comprised of the position of surgical tools at regular time instances along with the ultrasonic data acquired at specific time instances. The time instances act as a common parameter that help synchronize the position information of the surgical tools with the ultrasonic data acquired during the same procedure.

While the first surgeon would have proceeded with the complete surgical procedure, a second surgeon may use the recorded first data set as a simulated surgical scenario. The second surgeon may pause the playback of the same surgical procedure at a time point. For illustration purpose, this time point may be shortly after completion of craniotomy. The second surgeon may then choose another simulated dural opening or a different simulated sulcal opening based on the presence of high-risk vasculature immediately below the dura—as observed from previously described ultrasound image. This action will generate a second data set. The second data set will have a pointer at the start of the data series to indicate the exact time point in the first data set where second data set begins. New data sets can be created so that that one can view a combination real surgical recordings and simulated surgical recordings and chose to observe different approaches to the same initial disease condition. All such alternative data set corresponding to the same initial disease condition may be simultaneously stored and retrieved on demand and alternative intervention methods compared by a human If metrics are associated with alternative clinical approaches described above, surgical steps with highest metrics or scores may be combined sequentially to arrive at an overall optimal procedure.

The information recorded according to the preceding embodiments may be stored in an information store or database of procedures, optionally along with other data such as data obtained from a local tissue analysis, or from an imaging system, and can be used as an intraoperative surgical data source, pathology correlation, and/or for future surgery/procedure planning and training Several examples of such methods are described below.

Methods involving Correlation of Diagnostic Data for Tissue Analysis

The following example embodiments provide methods involving the use of tissue analysis to supplement preoperative, intraoperative, or postoperative analysis and guidance. Such methods are provided to address a fundamental problem of surgery, namely the problem of needing, but not obtaining, sufficient information pertaining to tissue identification.

For example, during a neurosurgical resection procedure, a surgeon typically needs to decide, at various stages during the procedure, whether or not an exposed tissue region should be excised. There are several diagnostic modalities that the surgeon can use to attempt to make such a determination. However, no single intraoperative modality can generally give a definitive conclusion. Indeed, there are several types of brain tumors that appear similar to each other on MRI, however, are different in pathology. Hence, MRI alone is not sufficient to identify the tumor. Examining the cells under a microscope is the gold standard in tumor identification, but it is not feasible to perform on every excised piece of tissue and often cannot be performed intraoperatively. An approach to arrive at a definitive conclusion may involve the interrogation of a tissue region with one modality, in order to initially narrow down the possible tissue types. Then a second modality could then be used that would supply more information and further narrow the tree of possibilities. Eventually, it may be possible to definitively identify the tissue. Such a method is therefore complex and uncertain in its effectiveness.

Traditionally, there has been little integration between diagnostic imaging, surgery, and pathology in existing solutions. Imaging offers an opportunity to seamlessly present information between the disciplines of radiology (diagnosis), surgery (treatment), neurology (outcomes) and pathology (tissue analysis). Imaging, and pathology analysis targeting a specific region of interest can be correlated on the scale of the tissue sample size that is resected. Procedure outcomes are often dependent on the percentage of total diseased tissue that is removed, compared to the amount of healthy tissue that is accidentally resected.

For achieving a more accurate pathology sample to imaging correlation, a more accurate method of registering a volume of interest of a tissue-sampling device, and delivering the tissue-sampling device to a region of interest within a subject, may be employed, as described below. Furthermore, in order to locate a smaller volume of interest in a larger surgically excised volume of tissue of interest, a system that can perform diagnostic measurements on the tissue in an ex-vivo manner, using the appropriate contrast mechanism, may be employed.

In some example embodiments, the ability to perform local tissue analysis on the scale of the volume of tissue to be resected, and to track the resulting local tissue analysis data relative to excised tissue, and to register to a more regional image of the tissue, may be employed to obtain a correlation between local, regional, full volume, and pathology results. This information can be tracked relative to the outcome of the medical procedure, or progression of the disease locally, as tracked by imaging on subsequent imaging procedures.

Accordingly, in some embodiments, an integrated system is provided that enables imaging on a full volume, regional, or local basis, in the context of a medical procedure, and provides the appropriate imaging with the appropriate tissue contrast to provide for diagnostic, surgical extent and outcome prediction. Such a system may be employed, for example, when larger regions are resected for the purpose of more certainly resecting a small target of interest inside a larger volume (for instance 10 cubic centimeter volume), where the system provides the capability of performing imaging of the resected surgical specimen in such a manner that the smaller region of interest can be analyzed at a higher resolution for pathological analysis. These and other systems, and associated methods, are described in detail below.

The following example embodiments illustrate various aspects of the present disclosure, in the context of an access port based neurosurgical tumor resection procedure. As noted above, understood is that such example embodiments are not intended to limit the scope of the present disclosure to neurological procedures, and understood is that the systems and methods disclosed herein may be readily adapted to, and employed for, various other types of medical procedures.

In some embodiments, a system is provided to enable tracking of individual locations within a patient's anatomy, provide local imaging data at the location, provide external imaging data when tissue is removed (hand-shake image). External imaging may be performed as a volumetric or a surface scan.

In one embodiment, a sample is transferred to pathology in a labeled container. The labeled container is uniquely identified in the system, and the system can locate the sample to a specific location in the imaging volume, through tool tracking, and to a set of in-vivo and ex-vivo imaging sets. Any larger scans of the tissue of interest can be used to target specific regions of interest.

The system may comprise i) a navigation system that registers a set of volumetric imaging scans, to a patient frame of reference, ii) intraoperative imaging in a targeted region of interest, iii) software system to register preoperative imaging, intraoperative imaging, and imaging of pathology samples, iv) a database to store relevant information, including, but not limited to, patient data, or Electronic Medical Records (EMR), Picture Archiving and Communication System(PACS), Treatment Plans, Lab Testing Reports, Pathology Reports and Imaging, Patient Outcomes (reports and lab tests), v) software system to search, weight metrics, calculate similarity or metrics, and rank based on said metrics. vi) a software system to present said results in the context of the decision making process (diagnostic scan, surgery, pathology diagnosis, outcome evaluation), vii) means of sorting and imaging biopsy samples.

The system may be employed to track and measure comparable tissue sample metrics throughout the process of diagnostic imaging, biopsy, treatment planning, surgery, and follow-up imaging. Thus, the system may provide comparable case information for patient(s) with similar metrics. These comparisons can better inform the clinical specialist of similar imaging, pathology, or outcomes for a given imaging, pathology or outcome condition for a specific patient.

In some embodiments, the system may utilize patient data already available, by way of current diagnostic imaging scans, lab results, patient information (EMR), to better inform surgery, pathology and outcomes for the case in progress. The information associated with the case in progress would likewise be recorded, tracked, and submitted to same informatics systems (EMR, image databases, lab results,), in a manner that they will contribute additional information for the next case In this way, the system may acts as an adaptive decision making system such that more patients treated, and the more often information is entered into a system for a patient, the more powerful the ability of the system to present more data to the physician for more effective decision making.

Figure 6A:
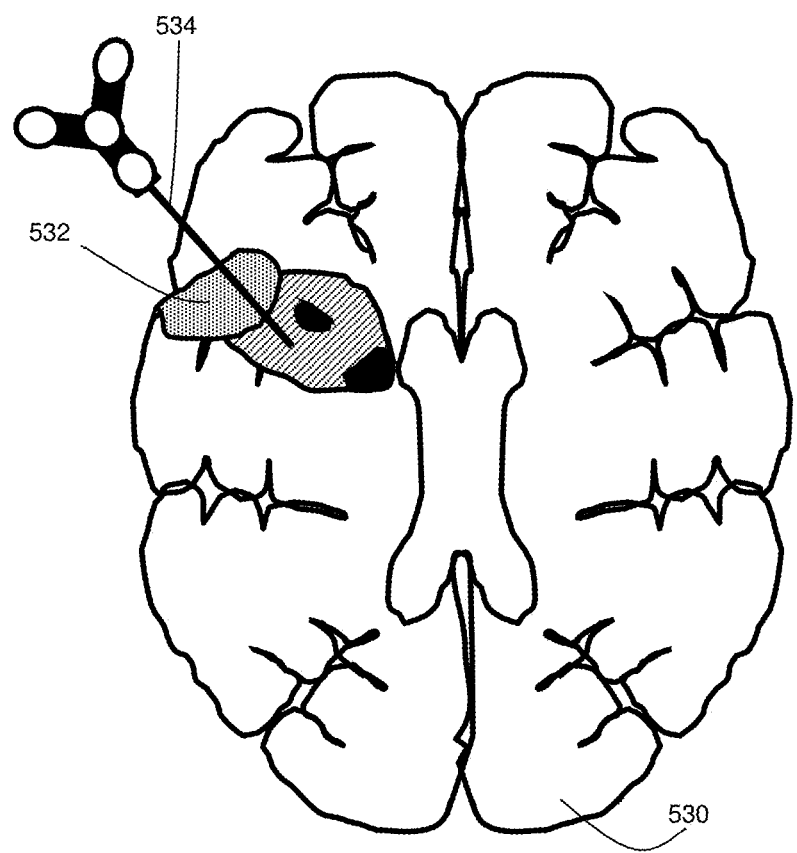
FIG. 6A is a diagram illustrating an axial view of the brain in which a tumor is present.

Referring now to FIG. 6A, an axial view of a brain 530 is illustrated, with a tumor 532 originating in the ventricle of the brain, and growing to the surface of the brain. The tumor is shown as three different textures, representing three different types of tumor cells. This is representative of tumors, which can be heterogeneous in their biology, and thus their appearance on imaging, pathology, and their response to treatments.

A tracked medical instrument 534 is shown relative to the tumor and pointing to a location in the tumor. When used in conjunction with a tracking system for tracking the instrument tip (a tip tracking strategy may be employed for flexible instruments, e.g. greater than 1 mm flex at the tip inside the tissue of interest, or the resolution of interest for that procedure), the position of the tracked medical instrument 534 is known relative to the local tissue region of interest.

In one example embodiment, if medical instrument 534 is a biopsy sampling device, or includes a biopsy device, and the biopsy instrument actuation is measured in coordination with the sample removal, and the sample is may be stored or tracked in a manner that it can be uniquely identified relative to this local tissue region. Tissue analysis, such as pathology results, can then be recorded and displayed relative to the location for which the sample was retrieved.

In another example embodiment, if medical instrument 534 is (or includes) a local diagnostic measurement device the local tissue diagnostic data obtained from a local diagnostic measurement may be stored or tracked in a manner that such that the data can be uniquely identified relative to this local tissue region. The local tissue diagnostic data, such as a local image or a Raman spectrum, can then be recorded and displayed relative to the local tissue region at which the diagnostic measurement was made.

In one embodiment, the location associated with one or more tissue analyses (e.g. a biopsy or a local diagnostic measurement) may be shown on a regional medical image that includes the local tissue region. In order to show the location of a given tissue analysis, the location data associated with the tissue analysis is spatially registered to the medical image data. This may be performed using registration methods, such as obtaining a preoperative medical image and spatially registering the preoperative image data to an intraoperative reference frame to which the location data associated with the tissue analysis is registered.

Figure 6B:
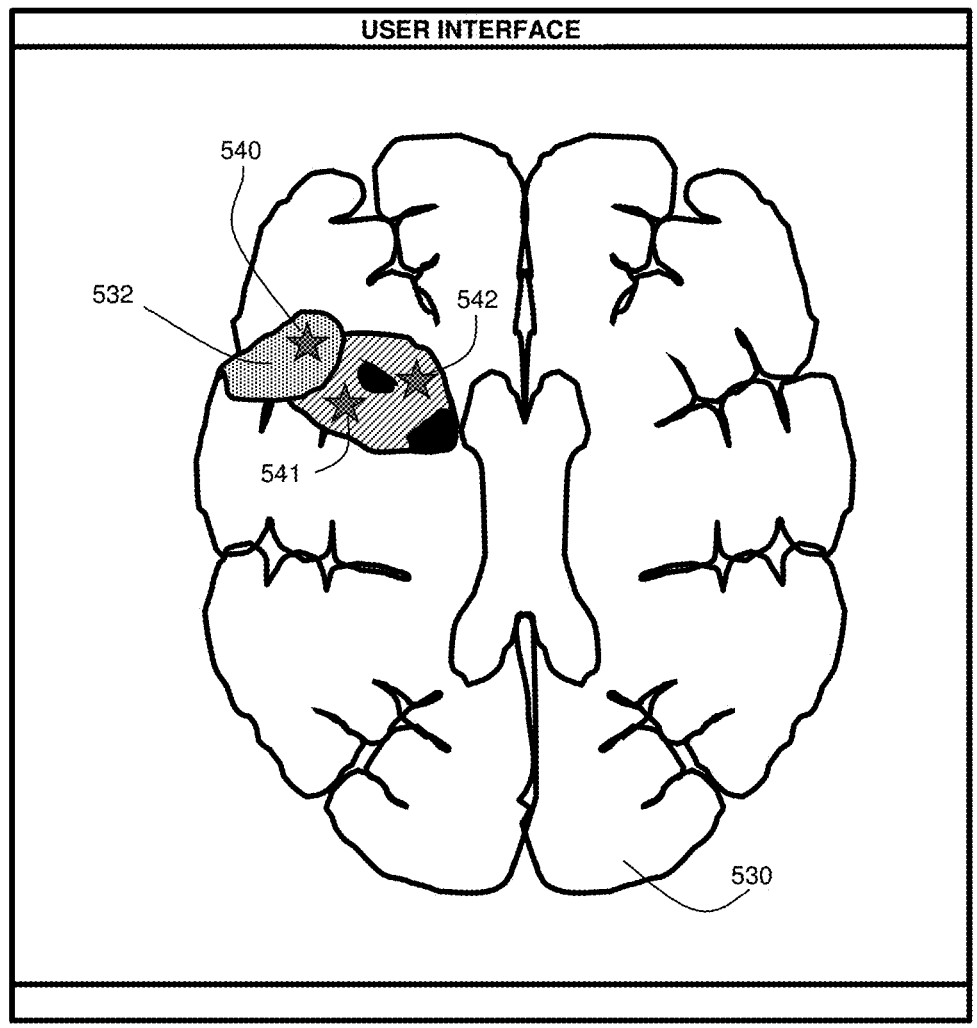
FIGS. 6B-6E are diagrams, together, illustrating an example user interface, in which a regional image has reference markers shown at the locations corresponding to tissue analyses.

Referring now to FIG. 6B, an example implementation of such an embodiment is illustrated, in which the location of three tissue analyses are shown by reference markers 540, 541 and 542 are shown, in a user interface, overlaid on medical image data.

Figure 6C:
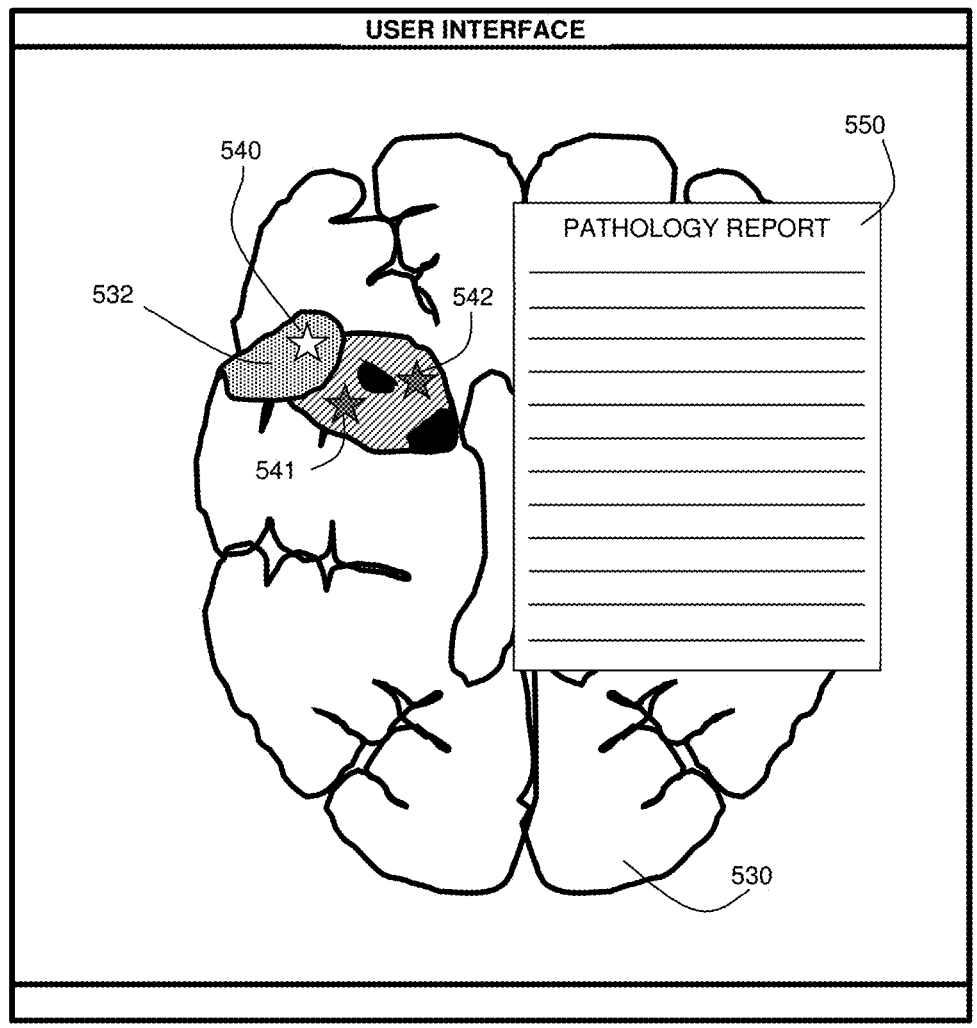
Figure 6D:
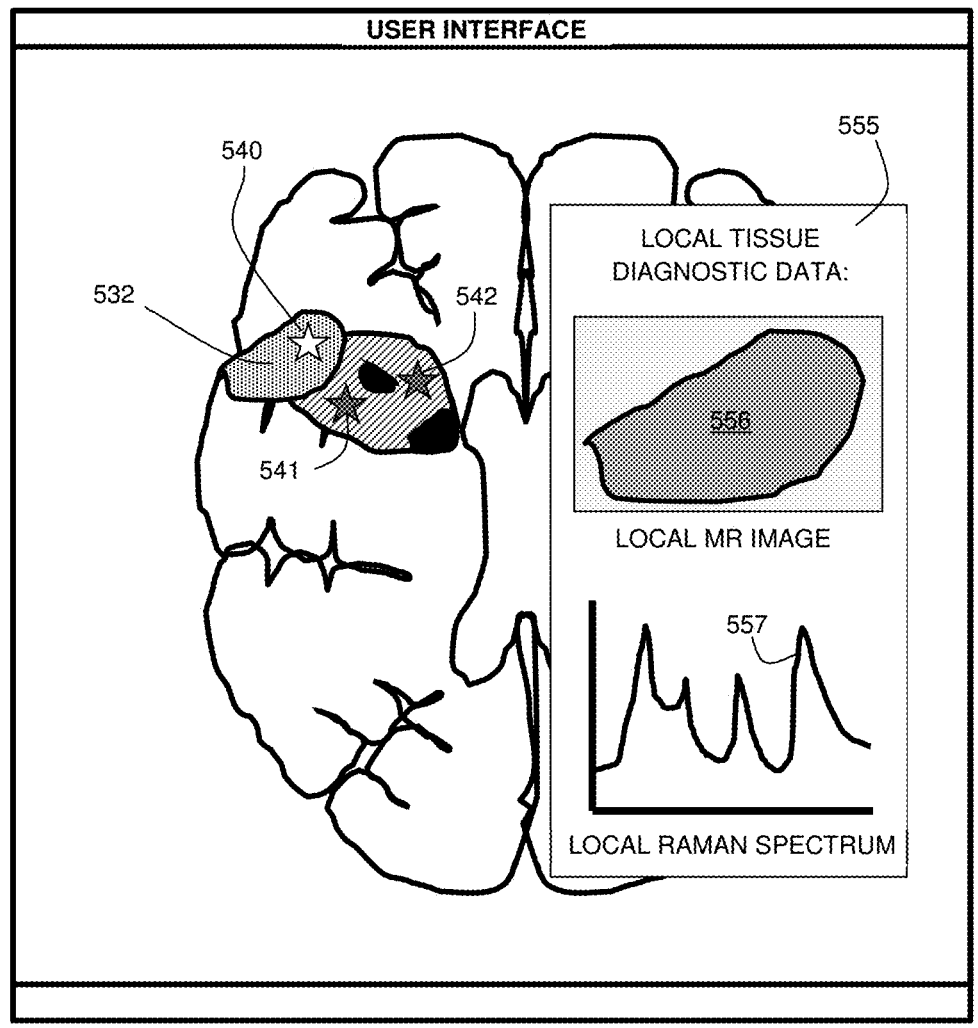

As shown in FIGS. 6C and 6D, reference markers 540, 541 and 542 may additionally serve as selectable graphical hyperlinks to information associated with the tissue analyses. For example, in FIG. 6C, the selection, via input from an operator (e.g. a mouse click or the touch of a finger or stylus on a touch screen display) results in the display of a pathology report 550 associated with a tissue sample obtained from location 540. In another example implementation, shown in FIG. 6D, the selection, via input from an operator, of reference marker 540, results in the display of local tissue diagnostic data 555, including an MR image 556 and a Raman spectrum 557 that were locally measured.

For example, if in-vivo image data is acquired concurrently with biopsy samples then the in-vivo imaging can be presented in the same context, and location, as the reference marker for the pathology results. If there are no corresponding pathology results, the in-vivo data may be provided in place of pathology results, as shown in FIG. 6D. Examples of local imaging modalities include OCT, high frequency ultrasound, Spectroscopy, MRI, MR Spectroscopy, tissue conductivity, electromagnetic imaging, etc.

It is noted that the present example provides method of reviewing local tissue diagnostic data and tissue analysis results in a manner that is very different from conventional methods. For example, some existing pathology software systems associate diagnostic image data based on hyperlinked text in a pathology report. In other words, the access to local diagnostic image data, or other diagnostic data, is provided through the pathology report. In contrast, the present embodiment allows for the graphical navigation to relevant location-specific diagnostic or tissue analysis data through a user interface, via the selection of a hyperlinked reference marker (e.g. a label, icon, text, or tag), on a regional medical image, where the position of the reference marker corresponds to the location at which a biopsy sample was acquired or a local tissue diagnostic measurement was performed.

In some embodiments, illustrating in FIGS. 6B-6D, there may be multiple locations for which hyperlinked data is available. In such a case, the user may select one or more of the reference markers in order to view, or otherwise obtain (e.g. print, download, or email) the relevant data.

Figure 6E:
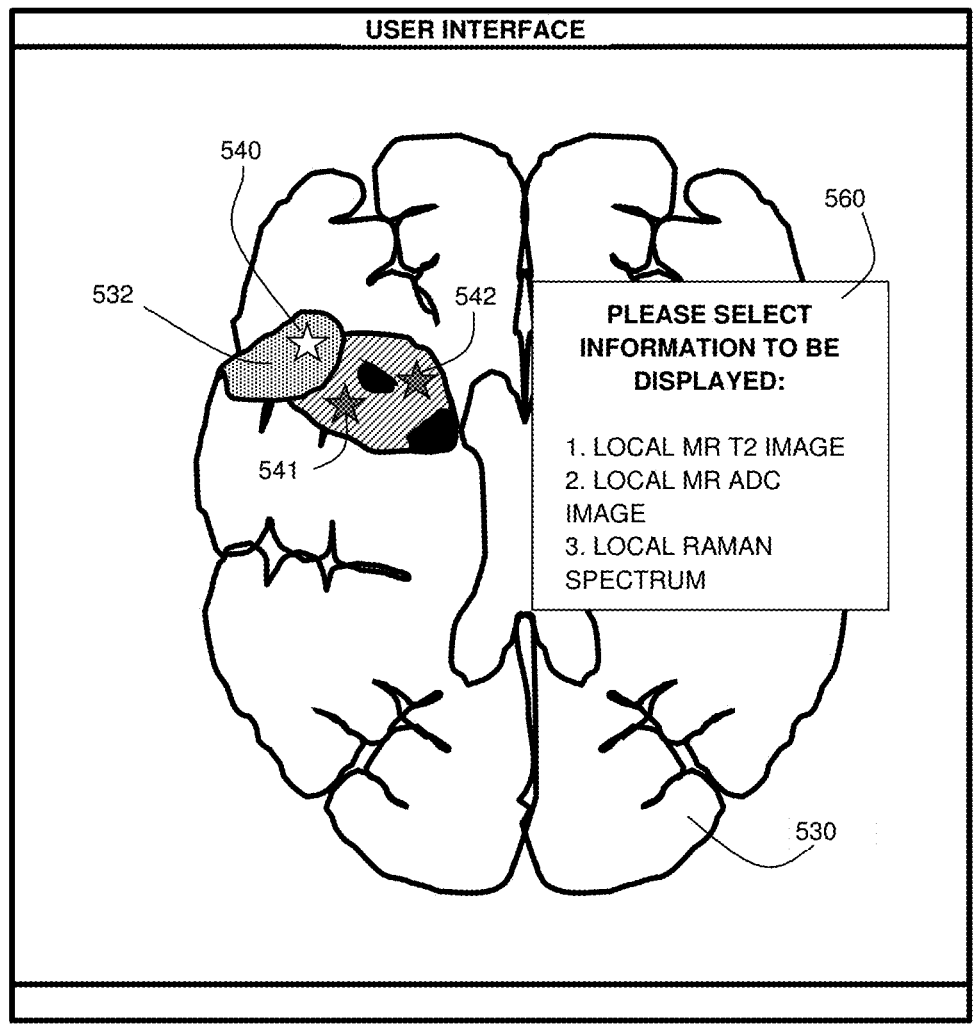

In some example embodiments, a single location may have multiple forms of associated local data. For example, as shown in FIGS. 6C and 6D, reference marker 540 has three different forms of associated data, including a pathology report (a form of tissue analysis data) and two forms of diagnostic data (a local MR image and a Raman spectrum). FIG. 6E illustrates one example in which a menu 560 may be provided to display a list of selectable items to display.

Figure 7:
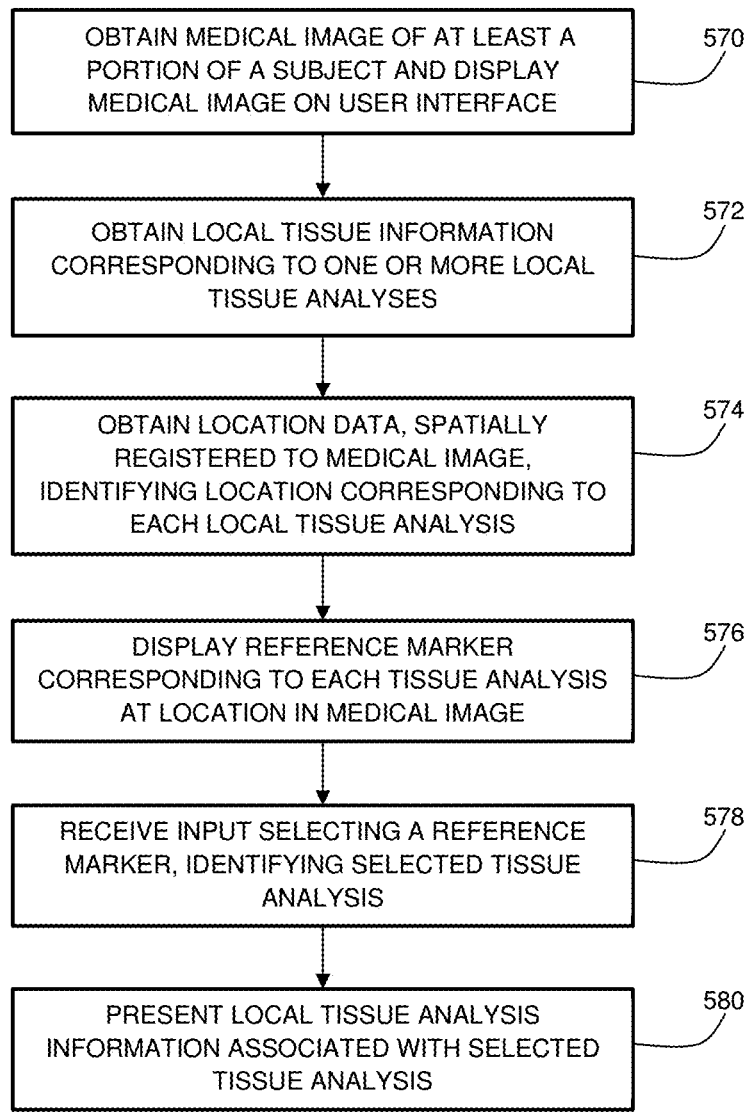
FIG. 7 is a flow chart illustrating an example method of displaying location-specific and hyperlinked tissue analysis information in a user interface.

FIG. 7 provides a flow chart illustrating the present example embodiment. At 570, a medical image is obtained of at least a portion of a subject and displayed on user interface. The medical image may be obtained, for example, preoperatively, using fiducial markers that enable subsequent registration to an intraoperative reference frame associated with a medical procedure during which the tissue analysis is performed. In another example, the medical image, and the local tissue information associated with at least one local tissue analyses, may be intraoperatively obtained during a common medical procedure.

Local tissue information, corresponding to one or more local tissue analyses, is then obtained at 572. Location data identifying the location corresponding to each local tissue analysis is obtained at 574, where the location data is spatially registered to the medical image. At 574, reference markers corresponding to each tissue analysis are displayed in the medical image, at the locations corresponding to their spatially registered location data. Input is then received from an operator at 576, the input identifying a selected marker, and therefore, a selected tissue analysis. At least a portion of the local tissue analysis information associated with selected tissue analysis is then presented, or is otherwise provided, to the operator.

Understood is that the variations of the embodiments shown in FIGS. 6B-6E may be performed without departing from the scope of the present disclosure. For example, the selected local tissue information may be displayed in a separate window of the user interface. In one example implementation, at least a portion of the selected local tissue information associated with the selected reference marker is displayed intraoperatively during a medical procedure, and wherein at least one said one or more local tissue analyses are performed during the medical procedure.

In one example implementation, at least one local tissue analysis may pertain to a previously medical procedure performed on the subject. The local tissue diagnostic data associated with at least one local tissue analysis may include additional tissue analysis information associated with a previous local tissue analysis that was performed at approximately the same location.

Understood is that a tracking system typically has a positional error associated therewith. For example, the will generally be an error associated with tip position, at the particular time when a biopsy sample or a local diagnostic measurement is obtained, for instance, due to registration error and imaging related distortions. The estimated spatial error associated with the location corresponding to a given tissue analysis can be estimated, and displayed as a visual representation associated with the corresponding reference marker. For example, the visual representation can be provided as a circle, sphere, error bars, or other suitable representation.

In additional embodiments, the method may be adapted to track specific locations that are registered across various modalities and resolutions enables the user to "drop points" virtually throughout the surgical cavity as tissue is resected. This allows a virtual margin to be created. These points that are defined in a local area, are linked to a local imaging frame. The region of interest is located in larger volume by tracking of the imaging device, and imaging is recorded in synchrony with that tracking. If imaging at a larger scale is performed without significant tissue deformation, an image with a larger field of view can be defined. In such a way, the larger fields of view can link to the entire imaging field. If the larger field of view can be imaged using contrast common to the preoperative, or intraoperative imaging, these points can be registered between the various clinical utilizations of the system.

Figure 8A:
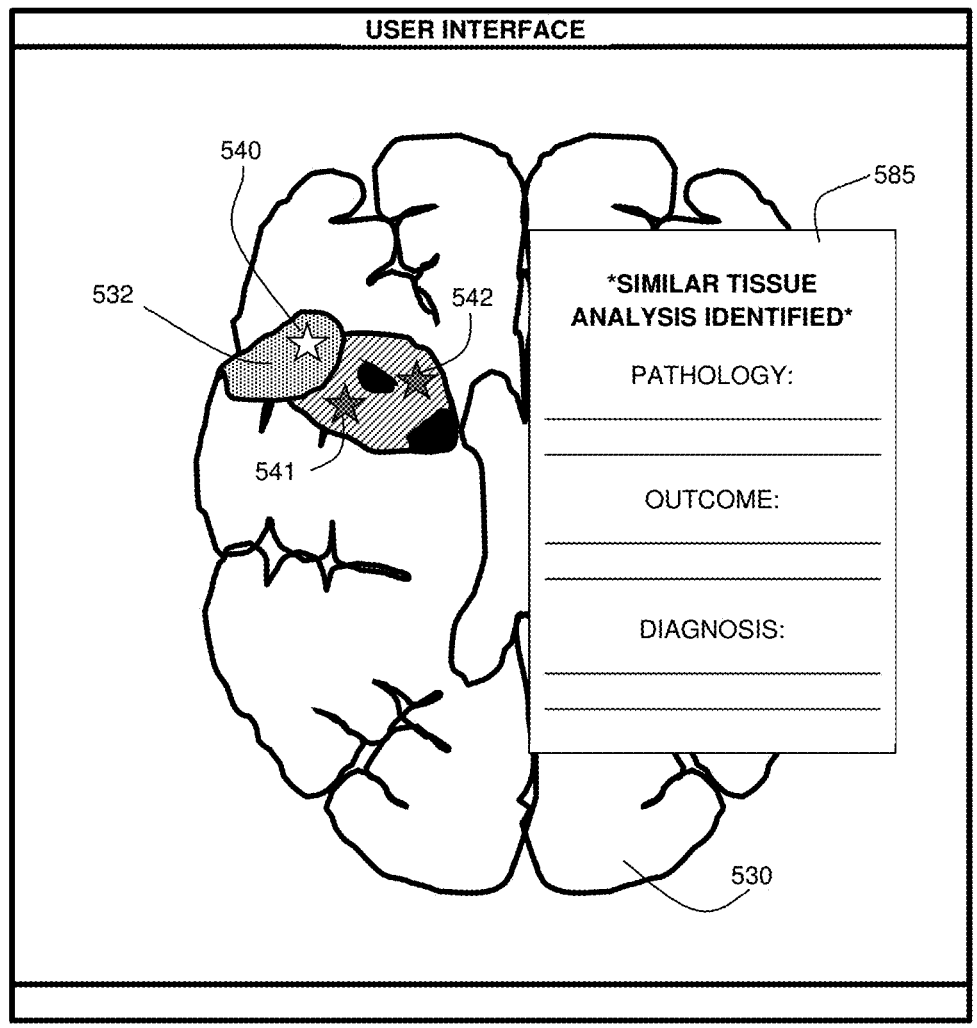
FIGS. 8A and 8B are diagrams, together, illustrating the selectable display, in a user interface, of tissue analysis information identified by searching a tissue analysis database.
Figure 8B:
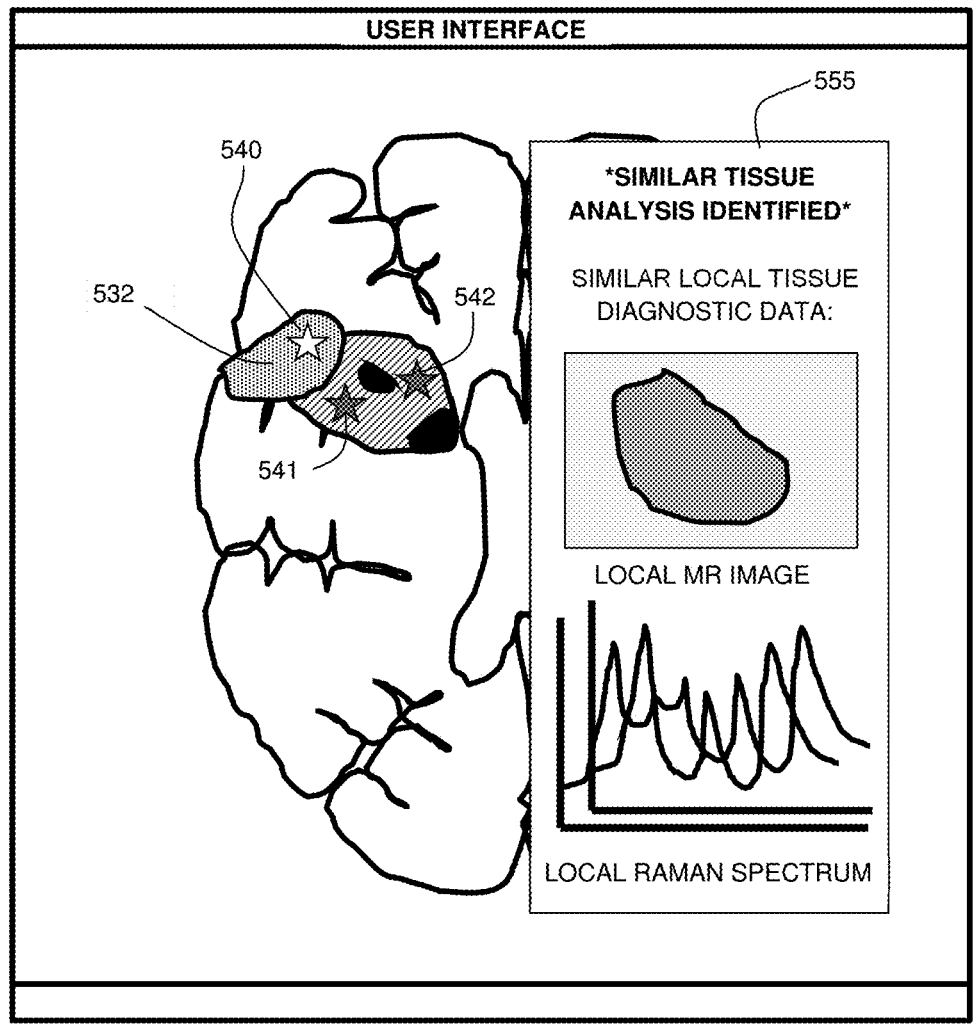

FIG. 8A illustrates another embodiment in which information pertaining to one or more similar tissue analyses may additionally or alternatively displayed in response to the selection of a given reference marker. Methods for identifying similar tissue analyses are described in detail below. As shown in the figure at 585, various form of tissue information pertaining to one or more similar tissue analyses may be presented via a user interface, such as, but not limited to pathology data associated with similar prior tissue analyses, outcome data associated with similar prior tissue analyses, and/or diagnosis data associated with similar prior tissue analyses. Furthermore, as shown in FIG. 8B, local tissue diagnostic data 590 associated with similar prior tissue analyses may be presented to the operator. These example embodiments, and related methods, are described in detail below.

As noted above, in some embodiments, tissue information pertaining to prior tissue analyses may be provided, based on a determination of similarity. In some embodiments, the determination of similarity may be made based on a comparison between local tissue diagnostic data associated with the subject, and archival local tissue diagnostic data obtained from a tissue analysis database. Such embodiments, involving the use of a tissue analysis database, may be employed according to a wide variety of methods, and in a wide variety of medical procedures, and stages of a given medical procedure. The information stored in the database may be tracked, updated and utilized as an adaptive evaluation tool, to search for similar results (pathology, imaging and outcomes) in the history of the patient, patients with similar imaging/clinical presentations, and/or database with all patients' information and their medical history.

Figure 9:
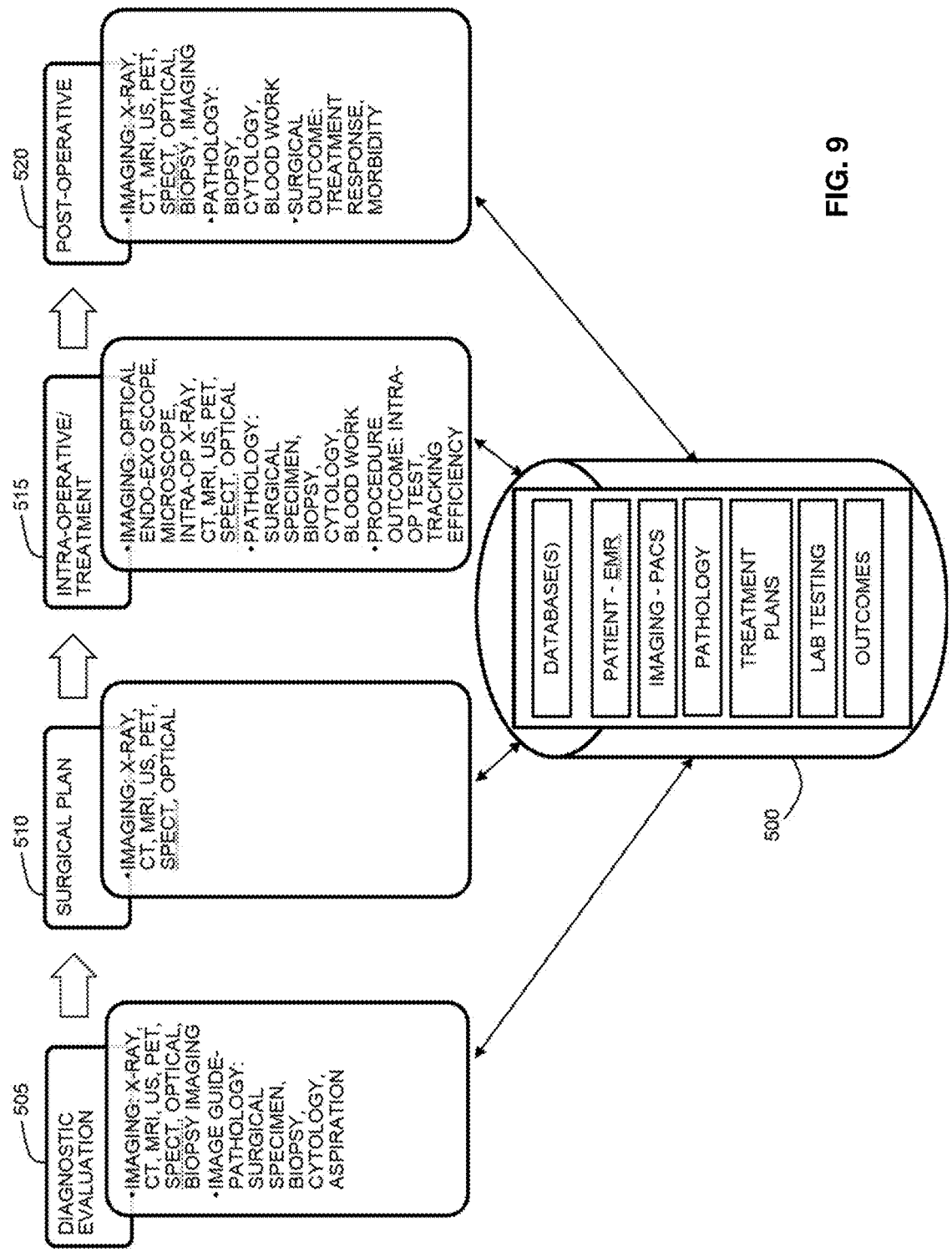
FIG. 9 is a diagram illustrating an example embodiment involving four aspects of patient care.

An example illustration of different stages of a surgical procedure, and their association to one or more tissue analysis databases, is shown in FIG. 9. The figure shows an example embodiment involving four stages of decision-making, namely diagnostic evaluation 505, surgical planning 510, intraoperative surgery, diagnosis or treatment 515, and postoperative analysis 520. These stages are shown in their relation to each other, and with regard to one or more tissue identification databases 500, which can be searched during one or more stages of a medical procedure. In this example, four aspects of patient care, where the use of a database linking registered imaging, pathology and outcomes can be utilized to improve diagnosis, surgical planning, surgical tissue differentiation and treatment and postoperative decision-making In the example workflow shown in FIG. 9, the diagnostic modalities listed, include, but are not limited to, a set of whole organ, regional, or local diagnostic modalities, which may include imaging modalities such as, magnetic resonance Imaging (MRI), computerized tomography (CT), positron emission tomography (PET), SPECT, ultrasound (US), x-ray, optical (visible light or sections of full EM spectrum), optical coherence tomography (OCT), photoacoustic (PA) or regional imaging modalities. These modalities can be acquired and shown as 1D, 2D, 3D, or 4D (3D+time), data sets, any may be registered to the patient in a dimensional and positional accurate manner Biopsy methods include core or endoscopic biopsy, surgical biopsy (large section), aspiration, or other methods of removing tissue of interest for further pathology analysis.

It is noted that the phrase "outcome", as used herein, refers to quantifiable methods to measure mortality and morbidity of the subject. This includes, but is not limited to, measurement of actual patient function, including direct measures of tissue viability, or higher-level function, as well as in-direct measurements, tests and observations. An outcome may also refer to the economic outcome of a procedure (in a specific or broad sense), and may include the time for the procedure, the equipment and personal utilization, drug and disposable utilization, length of stay, and indications of complications and/or comorbidities.

In some example embodiments that are described in detail below, tissue analysis may be performed by comparing local tissue diagnostic measurements (obtained with one or more diagnostic modalities) with archived local tissue diagnostic data. The archived local tissue diagnostic data is associated with prior tissue analyses for which tissue analysis data, such as outcomes, pathology data, and diagnoses, are available. The tissue analysis data is stored in a tissue analysis database (or two or more databases) with the associated archived local tissue diagnostic data. The local tissue analysis data (pertaining to a subject) may be employed to search the tissue analysis database to identify one or more similar prior tissue analyses, and the tissue analysis data associated with the similar prior tissue analyses may be provided to the surgeon, practitioner, or operator, or processed and employed for various uses and applications, examples of which are described further below.

Figure 10:
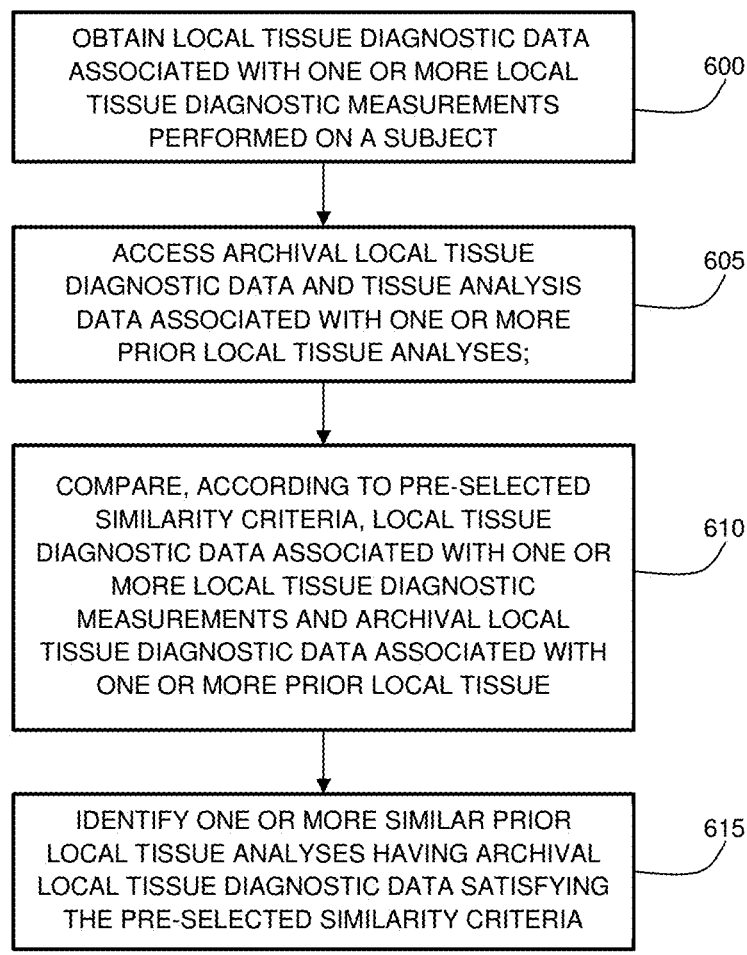
FIG. 10 is a flow chart illustrating an example method of identifying similar prior tissue analyses by performing a similarity analysis between local diagnostic data and archival local tissue diagnostic data stored in a tissue analysis database.

For example, referring now to FIG. 10, a flow chart is provided that illustrates and example method for correlating a local tissue diagnostic measurement with archival tissue analysis data. At step 600, local tissue diagnostic data is obtained, where the local tissue diagnostic data is associated with one or more local tissue diagnostic measurements performed on a subject.

For example, as described below, the local tissue diagnostic data may be local imaging data, such as a MR image obtained via an insertable MR probe, or local non-imaging data, such as locally measured Raman spectrum. Although this local tissue diagnostic data may not be sufficient to perform tissue analysis, it may be correlated with archival local tissue diagnostic data from prior tissue analyses from the same or other subjects, as described below. In cases in which the local tissue diagnostic data pertains to more local tissue diagnostic measurements made with more than one diagnostic modality, the location at which each local tissue analysis is made may be recorded, optionally along with a time stamp, as above described. The location may be employed to correlate local tissue diagnostic data obtained for a common tissue location, but with different diagnostic modalities.

At step 605, archival local tissue diagnostic data and tissue analysis data associated with one or more prior local tissue analyses is accessed or otherwise obtained. As noted above, tissue analysis data may include information including, but not limited to, one or more of pathology data, outcome data, tissue identification data, and/or diagnosis data. The archival local tissue diagnostic data, and the associated tissue analysis data, pertain to previous local tissue analyses, and may be provided in a tissue analysis database, as explained further below. At step 610, the local tissue diagnostic data associated with the one or more local tissue diagnostic measurements, and the archival local tissue diagnostic data associated with the one or more prior local tissue analyses, are then compared, according to pre-selected similarity criteria.

The local tissue diagnostic data pertaining to the subject may be employed to search the tissue analysis database for similar prior tissue analyses. Non-limited example of diagnostic modalities include MRI (T1, T2, DWI, ADC, FA, SWI, MRS), CT, Ultrasound, SPECT, PET, Raman spectroscopy, OCT, histological staining and high resolution optical imaging (microscopy and otherwise). For example, if the local tissue diagnostic data obtained for the subject includes a Raman spectrum, a tissue analysis database may the searched to find archival local tissue diagnostic data that was also measured via Raman spectroscopy (where the archived Raman spectra are stored correlated with tissue analysis data), and the measured Raman spectrum for the subject may be compared with the archival Raman spectrum to find a prior tissue analysis having a similar Raman spectrum.

At step 615, one or more similar prior local tissue analyses having archival local tissue diagnostic data satisfying the pre-selected similarity criteria are identified, thereby identifying a prior tissue analysis that may be representative of the local tissue region of the subject. The tissue analysis data associated with the one or more similar prior local tissue analyses may then be provided, displayed, or otherwise processed for further uses, as described below.

As described above, the tissue analysis database may be generated by performing multiple tissue analyses (e.g. for the same subject, or for different subjects), and storing, in a database, or suitable data structure, the local tissue diagnostic data obtained from local tissue diagnostic measurements, and tissue analysis data.

For example, one entry in a tissue analysis database may be constructed as follows, in which multiple diagnostic modalities are employed to interrogate a local tissue region of a subject (although understood is that an entry or data element may include diagnostic data from a single diagnostic modality). In the present example, three different diagnostic modalities are employed. A tracked Raman spectroscopy probe is employed to correlate the location the local tissue region with its Raman spectrum. Intraoperative MRI is also be employed to obtain MRI diagnostic data, where the use of a tracking and/or navigation system will allow the obtained MRI data to be correlated with the Raman spectrum. Finally, a tracked optical imaging device is be employed to optically interrogate the local tissue region, allowing the visual appearance of the tissue to be correlated with the Raman and MR data.

The local tissue diagnostic data associated with these measurements is stored, in the database (or other suitable data structure), along with, or correlated with, tissue analysis data pertaining to the local region. The tissue analysis data may include pathology data. For example, if a tissue sample from the local tissue region is excised and sent to a pathology laboratory, the pathology results (which may include cell type, microscope image, tissue imaging (for example, X-ray, MRI)) may be correlated, as tissue analysis data, with the local tissue diagnostic data that was intraoperatively obtained, and stored as an entry in the tissue database.

As described below, other types of tissue analysis data may additionally or alternatively be correlated with the local tissue diagnostic data to form the entry (e.g. database element) of the tissue analysis database. Examples of other tissue analysis data include, but are not limited to, outcome data (e.g. pertaining to the outcome of a medical procedure during which the local tissue diagnostic data was obtained), diagnosis data (e.g. pertaining to the diagnosis of a given pathology), and additional data pertaining to the subject (such as, but not limited to, demographic data, genetic data, and/or medical history data). In some example embodiments, the diagnostic data from two or more different diagnostic modalities may be employed allow for improved tissue analysis, as the same tissue region can be measured using multiple tissue analyses.

The tissue analysis database, which, as noted above, includes tissue analysis data from prior tissue analyses, may be used to guide, or suggest, which diagnostic modalities should or could be employed when performing medical procedures (e.g. surgical tissue resection procedures) involving known types of tissue. For example, if tissue resection of a known tissue type (e.g. a known tumor type) is to be performed, then the tissue analysis database can be searched to identify prior tissue analyses corresponding to the particular tissue type of interest, in order to identify diagnostic modalities that have been shown to have local tissue diagnostic data that is correlated with a given tissue type. The identified diagnostic modalities may then be employed during the tissue resection procedure, and the local tissue diagnostic data that is intraoperatively obtained may be compared with the archival local tissue diagnostic data to intraoperatively identify exposed tissue. In such an embodiment, it may be beneficial to filter the tissue identification database such that any local tissue diagnostic data that is included in the tissue identification database exhibits diagnostic data that is correlated with the tissue analysis data (e.g. such that local tissue diagnostic data that did not show features or a signature associated with the tissue type is excluded).

Figure 11:
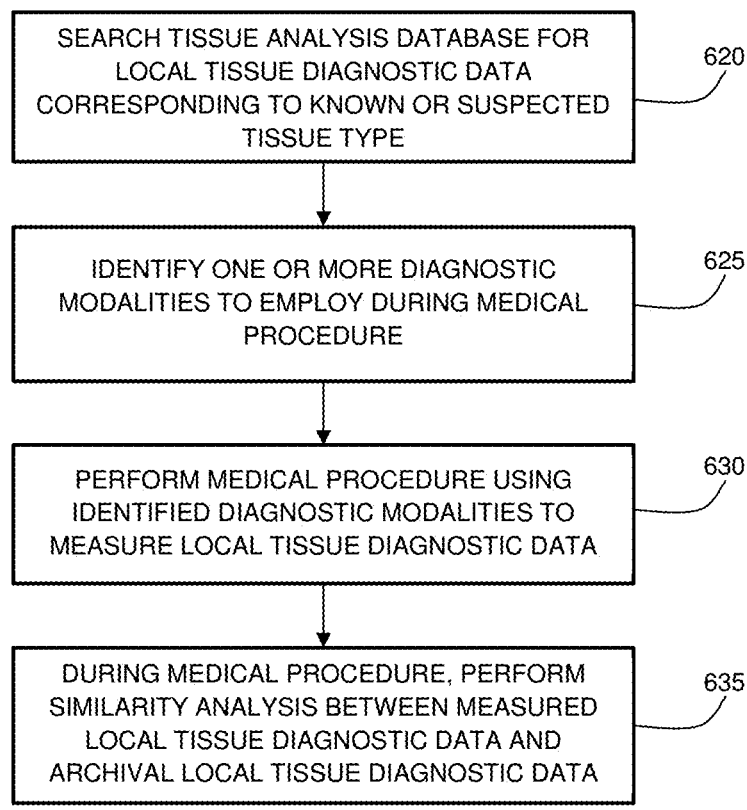
FIG. 11 is a flow chart illustrating a method of selecting suitable diagnostic modalities for use during a medical procedure.

In one example embodiment, a tissue resection procedure may be planned for a known, or suspected tissue type. FIG. 11 is a flow chart illustrating a method of selecting suitable diagnostic modalities for use during a medical procedure, and using the suitable diagnostic modalities to perform a similarity analysis between local diagnostic data and archival local tissue diagnostic data stored in a tissue analysis database. For example, a tissue resection procedure may be planned for a clinical case in which the tissue type is known to be, or suspected to be, a glioblastoma tumor. As shown at step 620, the tissue analysis database then be searched for diagnostic data pertaining to the known or suspected tissue type, in order to identify one or more suitable diagnostic modalities at step 625.

In the present example of FIG. 11, the tissue identification database would be searched for database entries pertaining to glioblastoma tumors, in order to identify diagnostic modalities associated with such database entries. For example, the search of the tissue analysis database may identify suitable diagnostic modalities as Raman spectroscopy, T2 MRI imaging, and ADC MRI imaging. The tissue analysis database may include entries whereby glioblastoma tumors have been associated with: Raman spectra having a specific spectral signature, T2 MRI image data in which the tissue appears dark, and bright ADC MRI data.

Accordingly, based on the knowledge of these diagnostic modalities as being suitable for intraoperative diagnostic measurements of this tissue type, a subsequent medical procedure involving tumor resection of a glioblastoma tumor (e.g. based on a suspected pathology, or based on a previously performed biopsy) may be performed diagnostic devices employing these diagnostic modalities, as shown at step 630.

During the medical procedure, tumor tissue may be intraoperatively detected by associating local tissue regions of dark T2 MRI, bright ADC, and also having the specific Raman spectra, with the glioblastoma tumor. Such an embodiment may enable greater and more precise margin delineation and simultaneously more complete tumor excision with more healthy brain sparing.

Figure 12:
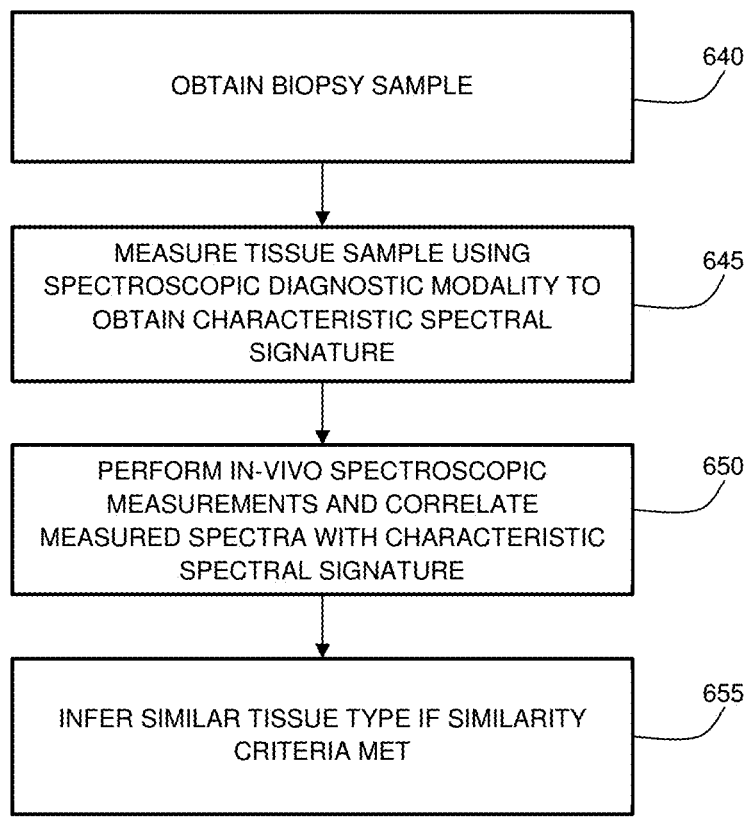
FIG. 12 is a flow chart illustrating an example method of determining similarity among different tissue regions based on spectroscopic measurements.

Another example embodiment is shown in FIG. 12. FIG. 12 is a flow chart illustrating an example method of determining similarity among different tissue regions based on spectroscopic measurements. During a medical procedure, a biopsy sample may be obtained, as shown at step 640. This sample may be measured using a spectroscopic diagnostic modality, such as a Raman spectroscopy, or hyperspectral imaging, in order to obtain a characteristic spectral signature associated with the tissue. For example, it may be known that the tissue type is tumor tissue. This knowledge of the tissue being tumor tissue may result from obtaining a tissue sample within the central region of a tumor. The spectroscopic measurement that is obtained from the tissue sample may be performed ex-vivo, using a suitable ex-vivo imaging device.

The local tissue diagnostic data obtained from the diagnostic measurement of the biopsy sample, having a characteristic spectral signature, may be subsequently compared with intraoperative measurements from an intraoperative, in-vivo, spectroscopic diagnostic device (such as a Raman probe, or a hyperspectral probe) in order to determine whether or not a local tissue region (e.g. a layer of exposed tissue remaining after tumor resection) is of the same type as the tissue sample, as shown at step 650. This determination may be made by performing an assessment of the similarity between the measured spectral signature from the tissue sample, and the in-vivo spectrum (or spectra) intraoperatively obtained by measuring the tissue, as shown at step 655. Such an embodiment may be employed to obtain an indication of when a tumor margin has been reached, and/or to confirm an alternative basis for determining that a tumor margin has been reached (such as an estimate based on a surgical plan).

As noted above and described in the flow chart shown in FIG. 10, the tissue analysis database may be intraoperatively accessed and searched during a medical procedure in order to obtain tissue analysis information pertaining to unidentified tissue. During such a medical procedure, a local region may be measured in-vivo by performing one or more local tissue diagnostic measurements. For example, when performing a medical procedure in which one or more local tissue diagnostic measurements are made on an unidentified tissue region, the local tissue diagnostic data obtained from such diagnostic measurements may be compared with the archival local tissue analysis data in the database, in order to search for a prior tissue analysis having similar local tissue diagnostic data.

In the event that a prior local tissue analysis is identified, the tissue analysis data associated with the similar prior local tissue analysis may be provided and optionally processed such that it may be employed for various purposes and applications. For example, in embodiments, in which the pathology of tissue is unknown, pathology results from one or more similar prior tissue analyses can be presented when identified based on a search of the tissue database (e.g. as shown in FIG. 8A).

In order to avoid the system to be considered a fully automated computer based diagnosis system, the system can present one or more similar confirmed pathology cases that can be examined by the operator. This data can be reviewed, and the associated imaging examined in visual comparison.

Referring again to FIG. 8B, in some example embodiments, archived local tissue diagnostic data that is deemed to satisfy similarity criteria may be presented to an operator using a graphical user interface. In one example implementation, in which the similar archived local tissue diagnostic data is imaging data, the region in the imaging set with the confirmed pathology may be scaled and presented in a similar size, orientation, and/or configuration as the active case (the case which the physician is comparing against), in a compare mode. Noted is that this may not provide a definitive determination of tumor pathology based on imaging—and instead may provide an informative and suggestive search and retrieve functionality that presents the appropriate data based on search results.

In one example embodiment, the local tissue analysis database may also include time-dependent medical procedure data recorded during a medical procedure in which one or more prior local tissue analysis were performed. This may allow a surgeon or operator to replay one or more portions of a similar prior tissue analysis identified according to the aforementioned methods. The time-dependent medical procedure data may include time-dependent positional information associated with the position and the orientation of one or more medical instruments employed during the medical procedure, which may be processed to render and display a time-dependent simulation of one or more of the medical instruments during at least a portion of the medical procedure.

In one example embodiment, the method may be adapted to provide a computer recommended surgical plan, or an evaluation of a user selected surgical plan. For example, the tissue analysis database may include surgical plan data for at least one similar prior local tissue analysis. This may enable an operator, having identified a similar tissue analysis according to one of the methods described above, to review, or simulate, one or more steps of the surgical plan that was employed for the previous tissue analysis.

In another example implementation, a proposed surgical plan, outlining a planned medical procedure for a subject, may be compared with surgical plan data stored in the tissue analysis database. This may allow a clinician to observe or review outcomes of similar surgical plans stored in the database.

In some example embodiments, the method may be adapted to provide a computer recommended surgical plan, or an evaluation of a user selected surgical plan. For example, the database may be searched for similar approaches that were taken for similar tumors, tissues and critical tissue structures. The search can be done in a similar manner as described as above, but instead of searching for the optimal outcome, the search is performed to best match the user selected approach.

Figure 13:
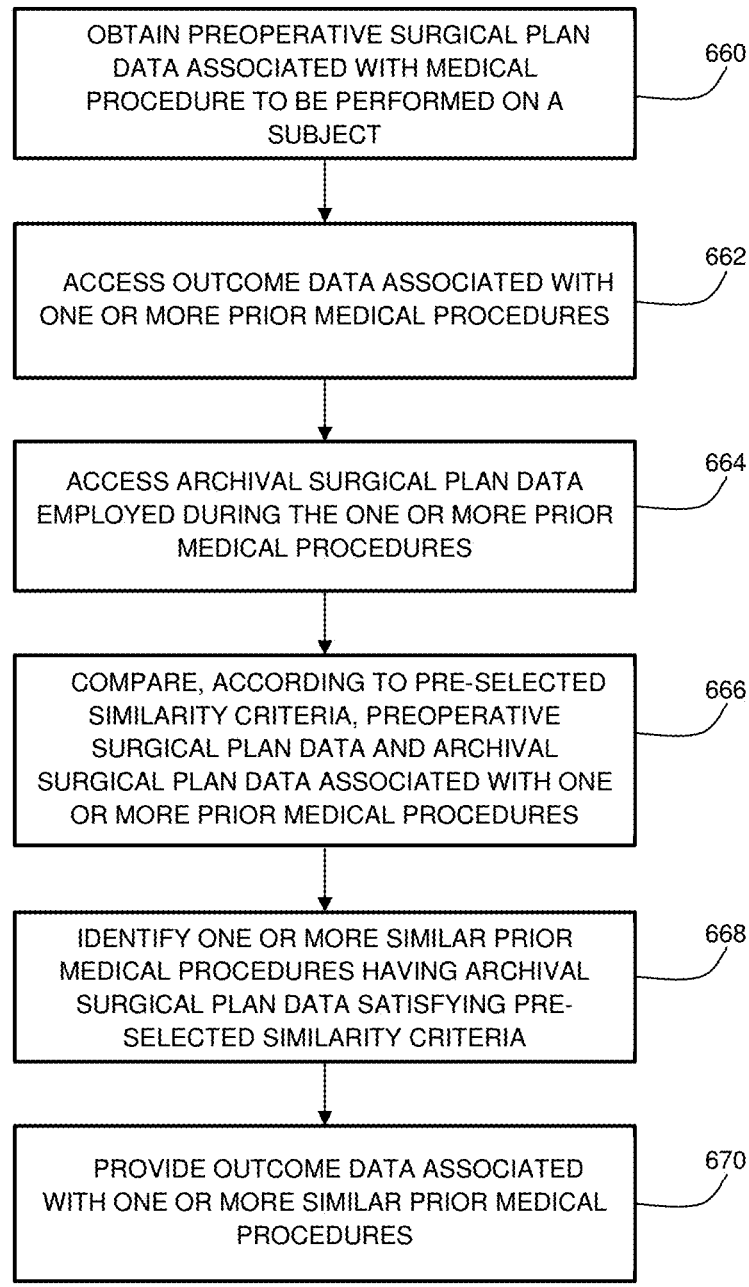
FIG. 13 is flow chart illustrating an example method of obtaining outcome data associated with a prior medical procedures having a similar surgical plan to a proposed medical procedure.

FIG. 13 provides a flow chart illustrating an example method employing a tissue analysis database, where in the present example embodiment, the tissue analysis database includes to identify prior tissue analysis having a similar surgical plan that was performed. At step 660, preoperative surgical plan data associated with medical procedure to be performed on a subject is obtained. The tissue analysis database is then accessed at steps 662 and 664 to obtain outcome data and archival surgical plan data associated with one or more prior medical procedures. The Preoperative surgical plan data and archival surgical plan data are the compared according to pre-selected similarity criteria at step 666, and one or more similar prior medical procedures having archival surgical plan data satisfying pre-selected similarity criteria are identified at step 668. If one or more prior medical procedures are identified having similar surgical plan data, outcome data associated with the similar medical procedures may be provided. The outcome data may be used, for example, to infer to potential effectiveness of a given choice of surgical plan.

Methods of Performing Similarity Analysis with Prior Tissue Analyses

Many of the embodiments described in the present disclosure involve the assessment of similarity between local tissue diagnostic data pertaining to tissue analysis performed on a subject, and archival local tissue diagnostic data stored in a database, in order to identify one or more similar prior local tissue analyses. Performing such similarity assessment first requires the selection of appropriate metrics or criteria that differentiate the data set in the clinical context. In the specific case where local diagnostic measurement is composed of images, an approach in computer vision is to detect and describe local features in images. Such features are referred to as "keypoints." A method such as Scale-Invariant Feature Transform (SIFT, U.S. Pat. No. 6,711,293) is an example of algorithm that is used for the purpose of detecting and describing local features that aid in searching image data sets. Second step of the search involves judicial reduction of the size of the data set based on additional context associated with the data set. First, selection and measurement of appropriate criteria is explained.

In some non-limiting examples, the clinical data set may include imaging contrast dynamics (contrast in-flow, contrast out-flow), diffusion information (e.g. FA or ADC mapping), quantitative T1 and T2, CT contrast flow, PET tracer dynamics. In all of these cases, the resulting data is a set of images, the images can be decomposed into essential criteria using feature extraction algorithms such as SIFT, SURF (Herbert Bay, Andreas Ess, Tinne Tuytelaars, Luc Van Gool, "SURF: Speeded Up Robust Features", Computer Vision and Image Understanding (CVIU), Vol. 110, No. 3, pp. 346-359, 2008) and Principal Component Analysis. Once the data is reduced to essential criteria, searching can be done in a lower dimensional space that comprises the essential criteria instead of the entire image data points.

Figure 14A:
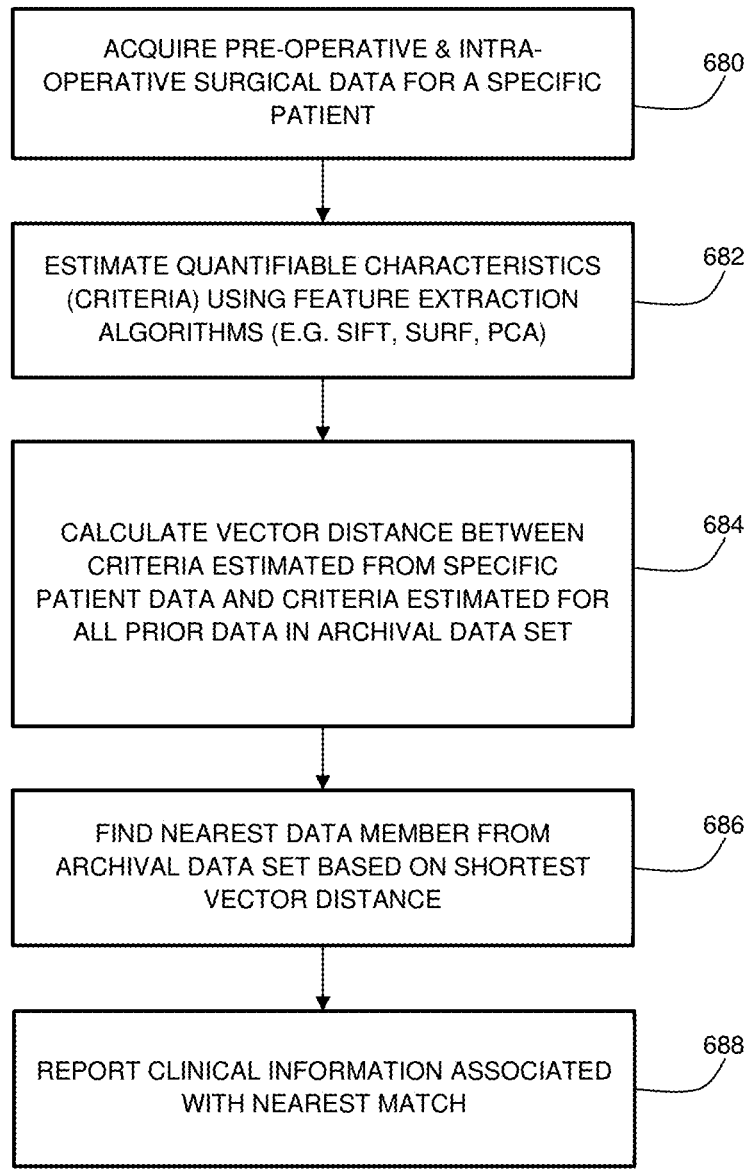
FIGS. 14A and 14B are diagrams, together, illustrating example search algorithms that may be employed to search archival data sets.
Figure 14B:
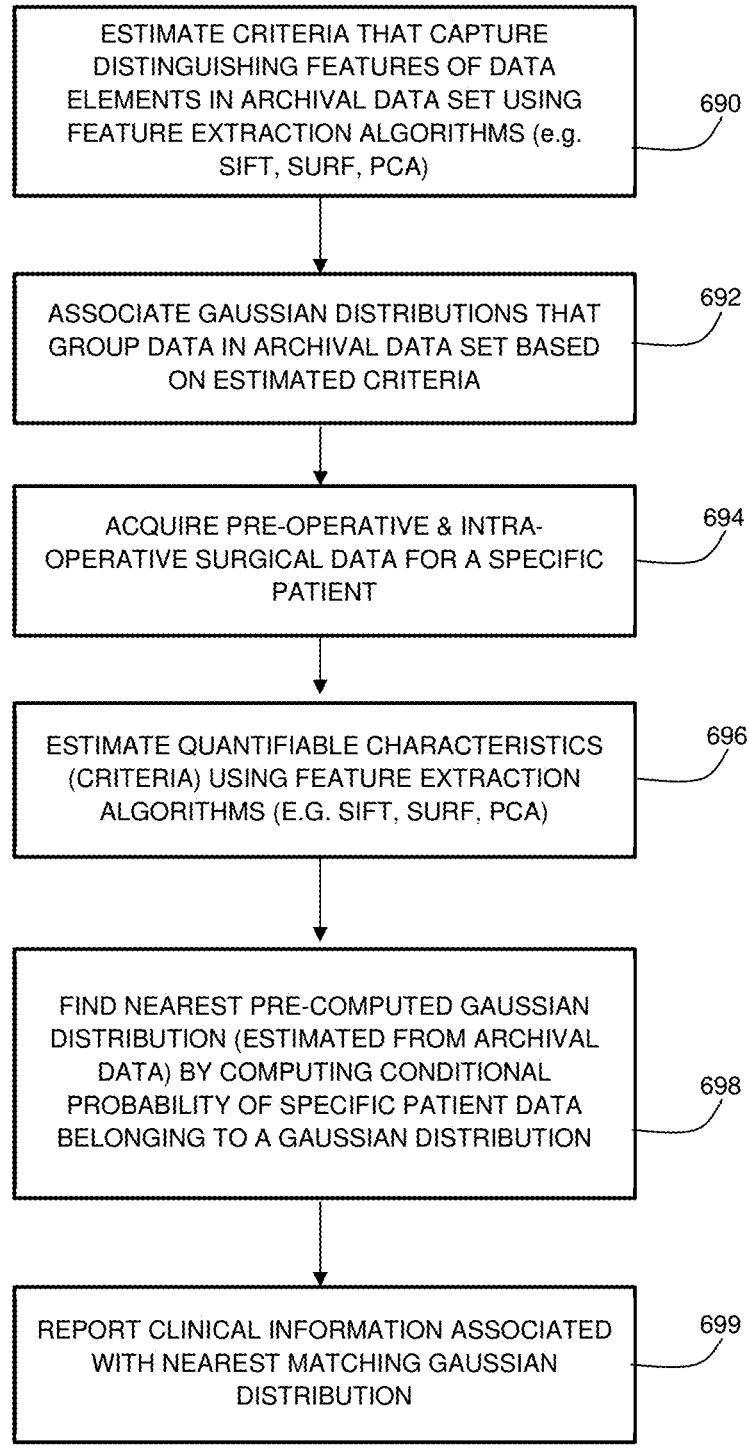

The process of matching a new clinical image data with an archival data set is illustrated in FIG. 14A and FIG. 14B. In one non-limiting example (shown in FIG. 14A), the process starts with decomposition of the newly acquired image data (step 680) into essential criteria (step 682) and comparison of the newly estimated essential criteria values against essential criteria values already stored in a database (step 684).) (e.g. calculating a vector distance). Examples of searching algorithms include nearest neighbor classifier (step 686), Bayesian classifier and the general class of clustering algorithms.

FIG. 14B illustrates another method for comparing patient-specific data with those in the archival data set. Here, the criteria are estimated from the data in the archival data set (step 690) and these criteria are grouped into clusters (step 692) described by multi-dimensional Gaussian distributions (reference: "Findings Groups in Data: An Introduction to Cluster Analysis," L. Kaufman and P. J. Rousseeuw, Wiley Series in Probability and Statistics). Preoperative and intraoperative data from a specific patient are then obtained (step 694) and criteria are estimated for this data (step 696). Conditional probabilities are finally estimated (step 698) to identify the most likely Gaussian distribution where the newly acquired data belongs. Clinical information (step 699), such as surgical outcomes, survival rate, postoperative complications, quality of life (QOL) measures, from archival data set can then be used to anticipate and appropriately prepare for the care of the patient. Even though these tools are readily available, above described approach does not utilize clinically relevant criteria; instead, abstract criteria are extracted and compared. This approach can be biased by spurious noise in the data and rationale for identifying a match cannot often be easily discerned.

Additional criteria such as tumor size, tumor location in brain anatomy tumor histology and pathology results may be used in combination with the imaging results to add clinically relevant criteria to the dataset. Thus, the range of data set that is searched (also referred to as "search space") is comprised of two sets: (i) essential criteria obtained by decomposing images and (ii) above described additional clinically relevant criteria. In one non-limiting example, tumor size is estimated by segmenting clinical image data (such as MR and CT) to isolate the tumor and then computing its surface area or volume. Segmentation of the image data to isolate the tumor may be done in 2D space in each of the original image slices that are used to construct the 3D volume data (e.g. MRI 2D image slices). Segmentation of 2D image may be accomplished using region-based segmentation methods (e.g. region growing, region splitting and merging, unsupervised segmentation), data clustering methods (e.g. hierarchical clustering, partitional clustering) or edge-based segmentation methods (e.g. watershed segmentation, markers based approach). These methods are in the computer vision industry and are explained in the context of generic image data and clinical images in "Tutorial: Image Segmentation," Yu-Hsiang Wang, Graduate Institute of Communication Engineering, National Taiwan University, Taipei, Taiwan, ROC. Natively 3D segmentation approaches may also be used.

Tumor location relative to the brain anatomy may be deduced first based on the identified location of the tumor relative to the brain. This may be achieved by identifying the centroid of a tumor region described previously. Then, this centroid location may be expressed relative to the patient's brain. Finally, translating this location to a general brain atlas such as that described in The Cerefy Brain Atlases ("Continuous Enhancement of the Electronic Talairach-Tournoux Brain Atlast," Neuroinformatics, Vol. 3, 2005) will enable the association of anatomical location of the specific tumor. This identification of location can be achieved by applying standard image co-registration techniques between the patient imaging and atlas exemplars.

Tumor histology may be quantified using imaging techniques such as Apparent Diffusion Coefficient (ADC) measured from diffusion weighted resonance (MR) imaging methodologies. Past publications have illustrated correlation between ADC and cellularity (reference: "Diffusion-weighted MR imaging of the brain: value of differentiating between extraaxial cysts and epidermoid tumors," J S Tsuruda, W M Chew, M E Moseley and D Norman, American Journal of Roentgenology, November 1990, Vol. 155, No. 5). Hence, the correlation can be used to build a mathematical model that transforms measured ADC values to cellularity measures. In summary, all of the above clinically relevant criteria may be quantified and associated with clinical images to arrive at a data set that is searchable based on clinically relevant criteria.

Finally, pathology information may be also added as a clinically relevant search criteria as follows. Biopsy is often performed prior to surgical resection of the tumor. The removed tissue sample may be analyzed using biochemical processing or monoclonal anti-bodies at a pathology laboratory to identify the type of tumor (reference: "Identification of proliferating cells in human gliomas using the monoclonal antibody Ki-67," Zuber et. al., NeuroSurgery, 1988, Vol. 22, Issue 2). Similarly, some of the tissue samples resected during surgical procedures are set aside for such pathology analysis. The information from such pathology analyses may be added to the data set collected during the surgical procedure by associating the results of pathology analysis with the exact location and time point where the analyzed tissue sample was removed. Thus, the pathology analysis results can be considered as metadata associated with the original position and time information captured during the recording of surgical procedure.

The metadata may be searched independent of position and time information to identify past surgical procedures (in the archival data) that are similar to a particular surgical procedure. In this case, the search algorithm may be a text-based searching algorithm that is used in searching text strings in large volumes of text data (reference: "A fast string searching algorithm," Comm Association for Computing Machinery, 20(10): 762-772). Identification of the pathology of the particular patient with those in the archival data set may aid in the evaluation of clinical outcome that may be anticipated for the particular patient based on what was observed for patients with similar pathology in the past.

A similar means of searching through established databases is possible using specific metrics from the local non-imaging diagnostic modalities. For example, metrics such as, but non-limited to, metabolite concentrations or ratios, local scattering or absorption, tissue stiffness (elasticity), anisotropy, etc., can be used.

In other cases, local imaging modalities may be employed which may provide enhanced imaging quality, resolution, and/or the ability to measure contrast mechanisms that cannot otherwise be imaged with external imaging probes. Imaging in this manner provides a unique opportunity to correlate quantitative metrics to the tissue sample of interest, and can facilitate diagnosis, registration between regional and local imaging, and provide a means to track the biopsy sample through detection to diagnosis through pathologic examination.

Additional information that may be analyzed to assess similarity may include specific patient information such as age, weight, the presence of certain genetic mutations, exposure or presence of viruses, or disease prevalence information. For example, in each of these more qualitative metrics an appropriate quantitative ranking may be provided and associated with the features to enable a similarity calculation.

A non-limiting example of associating scores with patient information is the association of cancer recurrence score with tumor size and tumor grade (reference: "A population-based study of tumor gene expression and risk of breast cancer death among lymph node-negative patients," Habel et. al., Breast Cancer Research 2006, Vol. 8, No. 3). Hence, previously described tumor size estimates may be associated with disease prevalence information. The latter information is another metadata that can be used as search criteria to identify other patients in the archival data set. Such identified information can be used to infer possible outcome of the current surgical procedure, such as survival period and quality of life after surgery. This information, in turn, can aid in choosing suitable post-surgical care for the particular patient. For example, if the tumor size indicates a high possibility (high score) for cancer recurrence then the patient can be watched more carefully with frequent imaging to monitor possible recurrence.

In some embodiments, the search of the tissue analysis database, and the associated similarity analysis, can be modified to include weighting factors, such that one or more criteria are assessed as having a greater weighting in the similarity analysis. In one example implementation, one or more weighting factors can be pre-selected. In another example implementation, one or more weighting factors can be associated with a decision tree. In yet another example implementation, one or more weighting factors may be selected by an operator (e.g. dynamically selected during a medical procedure). For instance, for a medical procedure involving a tumor that has been identified, or is suspected to be, a Stage 4 Glioblastoma multiforme (GBM), the weighting of the MRI contrast may be weighted as a higher number, for instance 2, verses all other factors weighted as one. As a contrasting example, in the case of a Stage 2 GBM, the weighting of the DWI ADC value may be weighted higher, for instance 3, verses all other factors weighted as one. In another embodiment, the features weighting can be determined based on a global calculation across multiple data points for a patient, or across a large patient population.

In one embodiment, a weighting can be applied based on the operator's interpretation of the results. For instance, if the surgeon determines the local Raman signal to be of high-quality, and clearly delineating a difference in tissue within that subject, they may choose to weight that factor higher than other factors such as CT perfusion of the area. They may also choose to exclude regions, or down-weight specific parameters—such as ADC values from a region of interest, if it appears the registration accuracy between the image sets is poor, or the imaging quality is not sufficient. In addition, local intraoperative imaging can be registered back to the radiology presentation of the data. In the future this can better inform diagnosis as discussed in the context of diagnostic (radiologic) utilization of the system. In this way, higher quality imaging can be used as an internal surrogate to tissue sampling and pathology analysis, and may in-fact be more accurate than the current accepted gold standard of tissue characterization.

EXAMPLES

The following examples illustrate non-limiting example implementations of various aspects of the present disclosure, within the context of preoperative, intraoperative, and post-operative neurosurgical procedures involving the resection of brain tumors. The examples presented herein are provided to enable those skilled in the art to understand and to practice embodiments of the present disclosure. They should not be considered as a limitation on the scope of the disclosure, but merely as being illustrative and representative thereof.

Example 1

Preoperative Analysis and Search of Tissue Analysis Database

Figure 15:
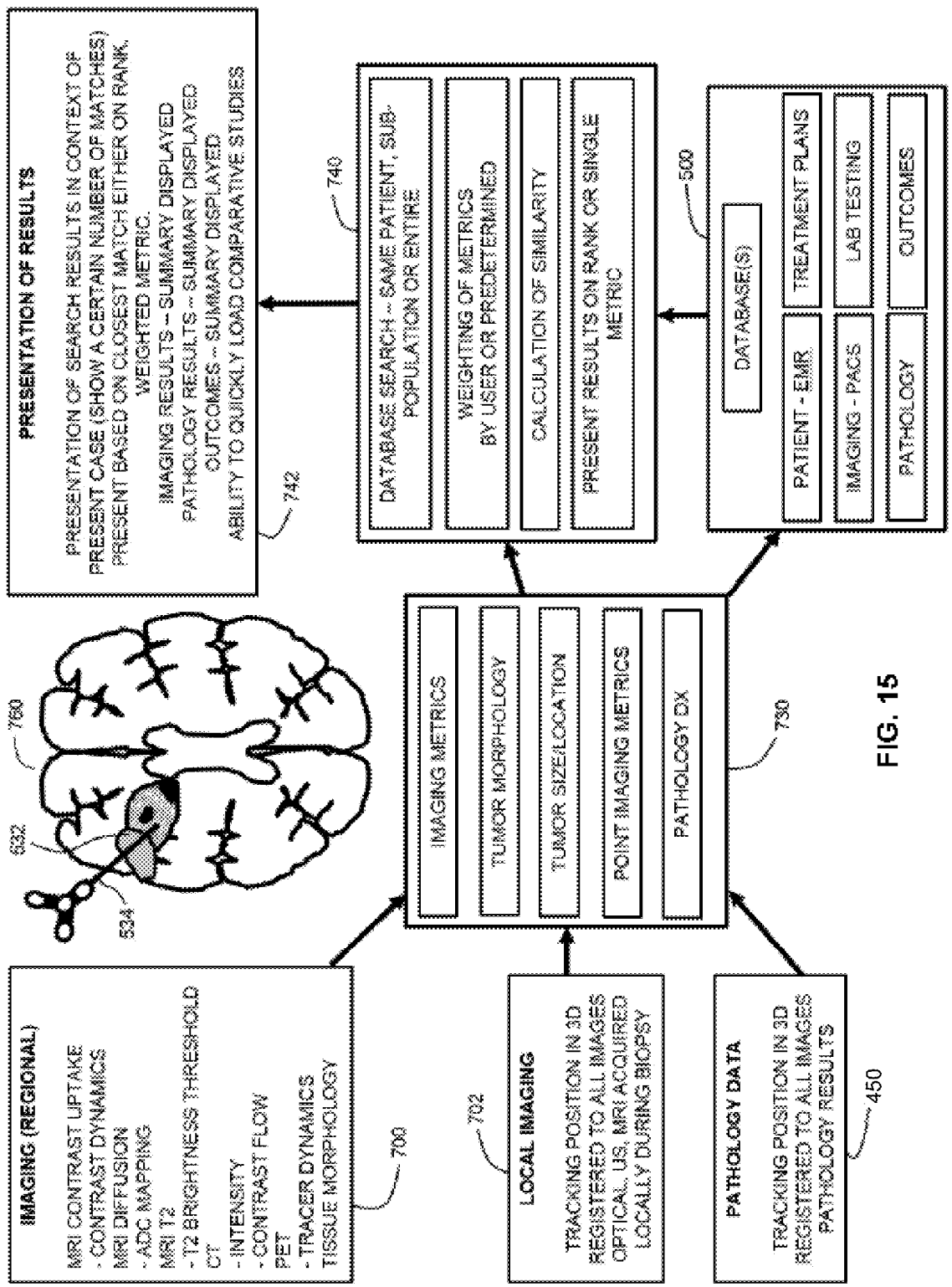
FIG. 15 is a diagram illustrating an example embodiment involving specific utilization of regional imaging, point imaging, and pathology data to link imaging and pathology results in a single patient, and linking results across subjects.

In a first example, shown in FIG. 15, various aspects of the present disclosure may be employed in the context of preoperative procedures involving preoperative imaging and a tissue biopsy. FIG. 15 is a diagram illustrating the inter-relationship between various aspects of an example implementation of the methods described above, showing how various diagnostic measurements and inputs are employed in order present search results based on a search of a tissue identification database 500. The present example implementation involves specific utilization of regional image data 700, local diagnostic measurements 702, and pathology data 704 to link imaging and pathology results in a single patient, and linking results across subjects.

Shown in the middle of the figure, is an axial view of a brain 530, with a tumor 532 originating in the ventricle of the brain, and growing to the surface of the brain. The tumor is shown as three different textures, representing three different types of tumor cells. This is representative of tumors, which can be heterogeneous in their biology, and thus their appearance on imaging, pathology, and their response to treatments.

A tracked instrument 534 is shown relative to the tumor and pointing to a location in the tumor. When used in conjunction with a tracking system, and a tip tracking strategy (as is needed for flexible instruments, i.e. greater than 1 mm flex at the tip inside the tissue of interest, or the resolution of interest for that procedure), the exact position of the surgical device is known relative to the tissue of interest with great certainty.

If this instrument 534 is used in conjunction with a biopsy sampling device, and the biopsy instrument actuation is measured in coordination with the sample removal, and the sample is stored or tracked in a manner that it can be uniquely identified relative to this location at pathologic analysis, then this pathology results can be recorded and displayed relative to the location for which the sample was retrieved.

As noted above, the location can represent on an image viewing system, identifying a reference marker (e.g. a label, or tag) on a regional image 700, that corresponds to the location at which the sample was acquired. Upon selection of that label, the system may present the corresponding pathology report on the screen for viewing. If there were multiple locations from which multiple samples are selected, each would have an associated report. This was explained previously in relation to FIG. 8A.

The navigation system would have associated tip position accuracy at the particular time when the sample was taken, for instance due to registration error and imaging related distortions, total accuracy for the tip could be estimated, and displayed as a visual representation around the center of that estimated tracked needle tip location (as a circle, or a sphere or like representation).

In one embodiment, if the user selected the point for which the pathology results were linked, a search of database 500 could be performed to look for other studies, which had similar metrics. In some non-limiting examples, the metrics 730 could include quantitative imaging metrics such as imaging contrast dynamics (contrast in-flow, contrast out-flow), Diffusion information (ADC mapping), quantitative T1 and T2, CT contrast flow, PET tracer dynamics. Additional metrics such as tumor size, tumor morphology or histology, and pathology results may be used in combination with the imaging results to characterize the location and enable a search. Even further metrics includes specific patient information such as age, weight, or the presence of certain genetic mutations. In each of these more qualitative features, an appropriate quantitative ranking must associate with the features.

As shown at 740, the database search can be weighted towards some metrics 730 having a greater weighting in the search. The weightings can be pre-set, or associated with a decision tree, or user selected. For instance, for a tumor that demonstrates a Stage 4 Glioblastoma multiforme (GBM), the weighting of the MRI contrast may be weighted as a higher number, for instance 2, verses all other factors weighted as one. As a contrasting example, a Stage 2 GBM, the weighting of the DWI ADC value may be weighted higher, for instance 3, verses all other factors weighted as one. In another embodiment, the features weighting can be determined based on a global calculation across multiple data points for a patient, or across a large patient population.

In the case of diagnostic imaging, where the pathology is unknown, a set of comparable pathology results can be presented based on a similar search method previously presented. In order to avoid the system to be considered a fully automated computer based diagnosis system, the system can present to the user a set of similar confirmed pathology cases that can be examined by the user, as shown at 742. These sets can be reviewed, and the associated imaging examined in visual comparison.

In order to make the viewing efficient, the region in the imaging set with the confirmed pathology would be scaled and presented in a similar configuration as the active case (the case which the physician is comparing against), in a compare mode. This is not a definitive determination of tumor pathology based on imaging—but a search and retrieve function that presents the appropriate data based on search results.

If local in-vivo imaging 702 is acquired at the same time that the biopsy sample is acquired, then the in-vivo imaging can be presented in the same context, and location as the tag for the pathology results, or if there are no corresponding pathology results, in place of those results. Examples of local imaging modalities 702 include OCT, high-frequency ultrasound, Spectroscopy, MRI, MR Spectroscopy, tissue conductivity, electromagnetic imaging, etc.

A similar means of searching through established databases 740 is possible using specific metrics from the local imaging. Metrics such as metabolite concentrations or ratios, local scattering or absorption, tissue stiffness (elasticity), anisotropy, etc., can be used. In most cases the local imaging will provide significantly enhanced imaging quality, resolution, or the ability to measure contrast mechanisms that cannot otherwise be imaged with external imaging probes. Imaging in this manner provides a unique opportunity to correlate quantitative metrics to the tissue sample of interest, and can facilitate diagnosis, registration between regional and local imaging, and provide a means to track the biopsy sample through detection to diagnosis through pathologic examination.

Shown on FIG. 15 are the various inputs (regional imaging 706, local imaging or other diagnostic measurements 702, and pathology data 704) to a software engine 740 that determines various metrics 730 (imaging metrics, tumor morphology, tumor size/location, point imaging metrics, and pathology results). These metrics 730 can contribute to associated database for that subject, as well as be used in a search of the specific subject database, or other databases to locate similar imaging, pathology, or anticipated outcomes for that subject, as shown at 500.

In one example implementation, the search may be performed using a search algorithms as previously described, with a weighting of the features used determined by, for example: pre-set weightings, contextually selected weightings, user selected, or modified weightings, weightings selected or modified based on data quality measures (e.g. if it appears that the fidelity of that measure is poor, it is rejected), and weightings selected in an adaptive, or trained manner The results may be presented, as shown at 742, in a manner that is pre-selected, contextually, or user selected, for instance always presented as a top ten ranking of subjects from the local institution database. It may be desired that these large datasets be accessible in a fast manner, therefore pre-loading of the typically viewed number of sets could be accomplished during processing of the search results.

Example 2

Preoperative Analysis and Search of Tissue Analysis Database

Figure 16:
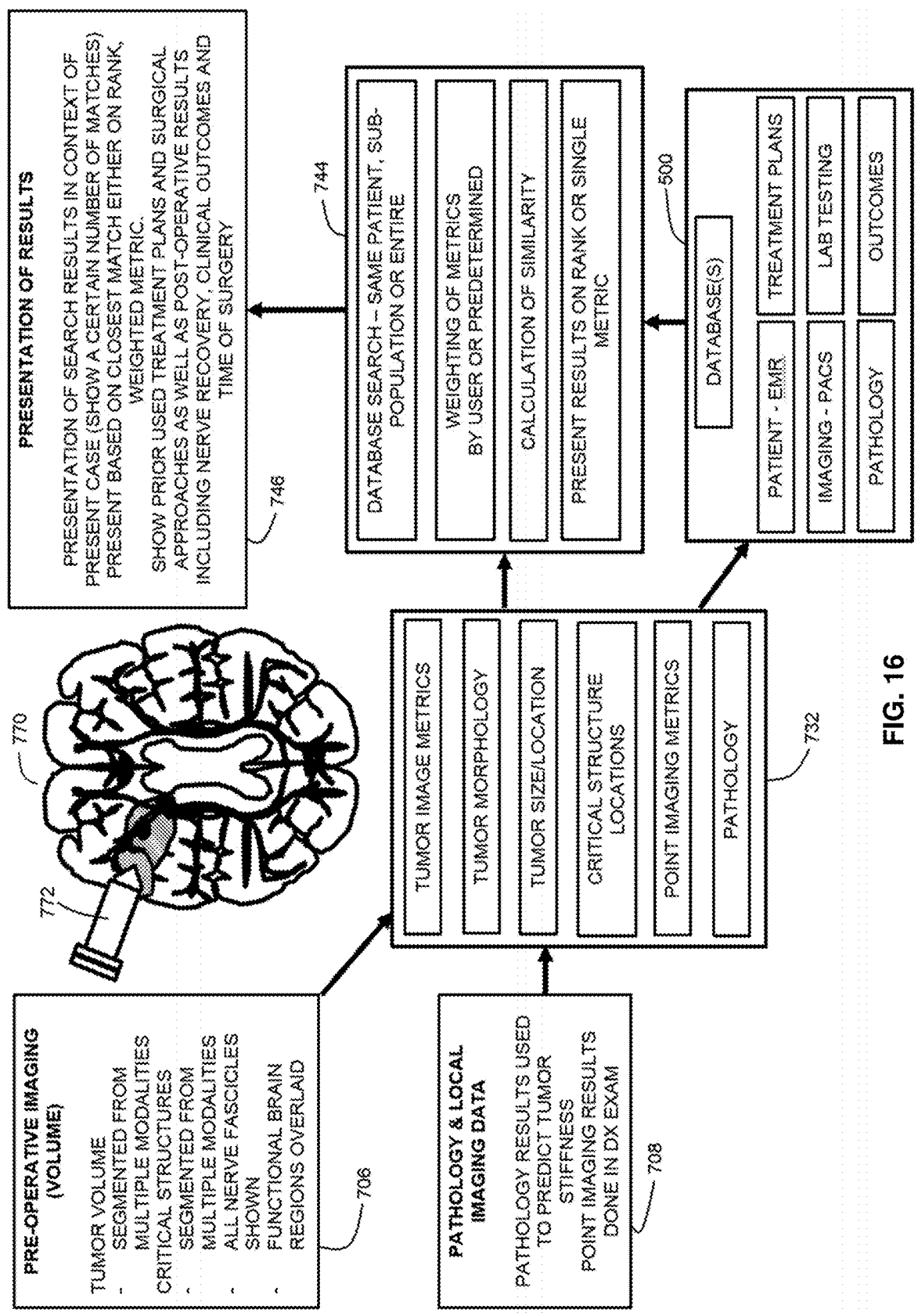
FIG. 16 is a diagram illustrating an example embodiment involving specific utilization of preoperative imaging, pathology, and point source imaging data to facilitate decision making for treatment and surgical planning

Another example implementation demonstrating of the clinical utility of the system is the use of an example embodiment of the system in context surgical and treatment planning for the subject, as illustrated in FIG. 16. FIG. 16 is a diagram showing an example embodiment involving specific utilization of preoperative imaging, pathology, and point source imaging data to facilitate decision making for treatment and surgical planning. Data from the results of previous surgical treatments performed on that subject, or subjects with similar imaging and/or pathology are presented based on an algorithmic search.

In this case, based on preoperative imaging 706, pathology results 708, and knowledge of the devices or system used in treatment (i.e. device physical properties, treatment modality properties), an expected outcome for the subject may be suggested based on subjects with similar imaging, pathology and medical condition. The optimal approach may be selected for the subject while using this information in the context of treatment or surgical planning Shown in the center of the figure, is an axial view of a same brain 530 as in FIG. 15; however, this time with a surgical implement 772 represented in the same coordinate frame. In this case, the implement is illustrated as a surgical access port, with an introducer device.

In the present example embodiment, the model of the associated device, structures and tumor from the preoperative images, can then be used, for example, to provide a computer recommended treatment plan, or an evaluation of a user selected treatment plan.

For the selection of a computer recommended treatment plan, the software system can search (as shown at 744) the database 500 for tumors that having various metrics or criteria 732, such as tumors of similar pathology, similar size, and located in a similar location in the brain, with corresponding nerve fascicle and critical structure locations undergone a similar surgical approach, i.e. with a similar device (for example access port). Corresponding nerve fascicles can be identified by associating tumor location with a brain atlas. Further, DTI atlas (such as that available at www.dtiatlas.org) may be used to identify nerve fascicles in the region.

Various properties associated with a tissue region of interest may be obtained from preoperative imaging 706. For instance, a tumor volume may be determined from the images from multiple modalities. Tumor metrics 732 such as stiffness can be determined or inferred using the external imaging (DWI, T2, MR Elastography), internal imaging if performed in conjunction with biopsy (OCT measured stiffness, tissue anisotropy, biosensors, i.e. direct pressure measurement), or pathology would contribute to the model of the tumor (vascularity, tissue fibrosis). Finally, preoperative diagnostic information may be used to rank the various search criteria. For example, if the patient has been already diagnosed with Glioblastoma, the search criteria may add higher weight to past surgical data in the archival data set or database 500 that correspond to tumors located in the frontal and temporal lobes since Glioblastoma are typically confined to these regions.

The end result 746 could be a ranked set of cases with a selected surgical approach, the associated patient outcome and postoperative imaging set. The patient outcomes could be quantified and an optimal value would be calculated based on weighted rankings In an additional example embodiment, if the positions of the tools are tracked for those procedures, the surgeon can watch the position of the devices, and the tools that were selected for that case. In this way, the surgeon can be informed of similar cases, their approaches, and their outcomes, in a way that can inform for their approach.

In a second method of using the model, the surgeon may select a surgical path for resecting the selected tumor, with or without using the model in a predictive manner that searches a database, where the model could inform upon the expected outcome.

In one non-limiting example of using surgical path as a search criteria the path of the tools and the volume of tumor predicted to be surgically resected, can be used to search a database for similar approaches that were taken for similar tumors, tissues and critical tissue structures. The search can be done in a similar manner as described as above, and the search is performed to best match the user selected approach.

For example, the search, in this case will may consist of first matching the planned surgical path to previously stored surgical paths in the archival data set. The surgical paths can be represented as a set of vectors that sequentially represent the entire path with each vector representing one segment of a piecewise surgical path. Congruence between thus described directed vector path and those previously stored in the archival data set can be estimated using such mathematical techniques as Hamming distance or Levenshtein distance (reference: "Error detecting and error correcting code," Bell System Technical Journal, 1950, 29(2):147-160). These mathematical constructs provide a measure of similarity between pairs of directed vector paths and, hence, can be used as a search criteria. The search can be further constrained to those cases where estimated volume of the planned surgical procedure matches those in the archival data set. Hence, previous surgical procedures that closely match surgical path and tumor size can be presented to the surgeon to review prior to embarking on the actual surgical procedure.

The system may present a set of procedures 746 that had a particular surgical approach in that region, that the user may be informed by viewing the imaging, and actual case (a recorded movement of the surgical tools and imaging used in that region). In a similar manner, where surgical outcomes have been searched to mean patient outcomes, the economic impact of surgical approaches many be considered.

In one non-limiting example, the exact surgical tools used during various stages of a surgical procedure may be recorded since each surgical tool may be uniquely identified and tracked by a navigation system. Each surgical tool, in addition, may have additional parameters such as capital cost of the tool, cost associated with each use (e.g. cost of disposable or consumable components associated with the tool) and cost associated with technical staff using the tool. In this manner, the total cost of using all the tools or specific tools in a surgical procedure may be computed and stored along with position and time information of all the tools. This information may aid the surgical team and hospital administration to accurately track the cost of various surgical procedures.

Example 3

Intraoperative Analysis and Search of Tissue Analysis Database

Figure 17:
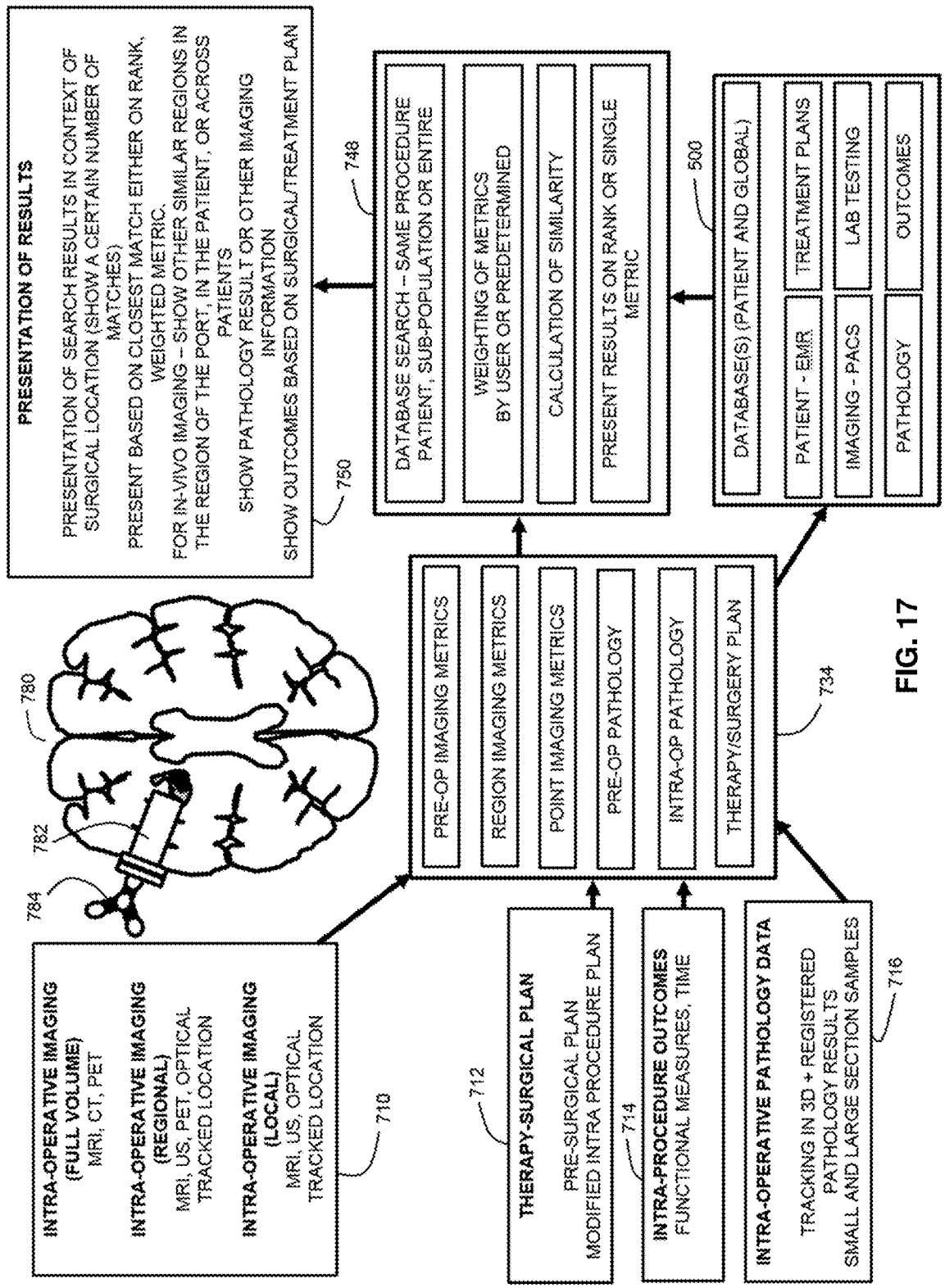
FIG. 17 is a diagram illustrating an example embodiment involving specific utilization of preoperative imaging to facilitate decision making for tissue differentiation and treatment.

FIG. 17 illustrates an example embodiment involving specific utilization of preoperative imaging (in the context of the surgical plan 712), intraoperative imaging 710 (full volume, regional, and point based), intraoperative pathology 716, and intraoperative procedure testing 714 (electrophysiology for example), to facilitate decision making for tissue differentiation and treatment. Database 500 is searched based on metrics 734, such that the results of previous surgeries performed on the subject, or subjects with similar imaging and/or pathology are presented 750 based on an algorithmic search 748. FIG. 17 illustrates an example implementation, in which an embodiment of the system is considered in the context of surgical or treatment guidance. Shown in the middle of the figure, in the center of the image, is an axial view of a brain 530, with the overlay of an access port 782, and a tracked surgical tool 784 (biopsy device, surgical resection device or point imaging probe).

In FIG. 17, much of the tumor that was originally shown in FIG. 15 is removed, and a small margin of tumor remains. It is in this context that the described system is most impactful. One of the biggest challenges in surgery is careful resection of the tumor at the boundaries of the tumor. By tracking the surgical tools, and registering imaging and pathology in the manner presented, the full informative and predictive power of all associated imaging and pathology results can be used to better differentiate between tumor locations within various regions of a subjects tumor and brain.

In FIG. 17, much of the tumor that was originally shown in FIG. 15 is removed, and a small margin of tumor remains. This is always a challenge in tumor resection, balancing the goals of complete resection and minimizing damage to healthy tissue. By tracking the surgical approach, tools used, pathology, and any other relevant criteria, the system can offer correlated retrospective information on resection performance (e.g. as narrowly as for a particular surgical team or procedure, or broadly through all available records) to aid in informing surgical decisions. For instance, for a particular tumor size, tumor location, nerve fiber locations, pathology, patient specific information (age, virus status, genetic background), there would be an associated set of prior cases with similar metrics. From these cases there would be instances where margin of tumor was left behind from taking too conservative of a tumor margin resulting in tumor being left behind, and visible (for instance under MRI). Whereas other case where there was too aggressive of a margin causing cognitive loss. In each case pre-operative imaging, such as MRI tumor volume as related to surgical resection margin by way of overlapping volumetric measurement, or intraoperative imaging results such as Raman Spectroscopic signature of the tissue status at the margin, could be related to the boundary. Additional information such as the proximity of the margin to major fiber tracts could also be measured relative to the margin to determine what proximity may lead to being too close causing nerve damage. This information would be presented to show the surgeon so they can use this data to guide the margin to fall between too aggressive, and insufficient surgical margin resection, as guided by prior case similarity search in the manner presented. In a similar manner, the use of pressure sensors along surgical instrumentation, such as the edge of the port, or the edge of surgical retractors, could provide an average, or peak measurement of pressure on the surrounding tissue. A search of clinical outcomes associated with similar instances of port positioning, or tissue retraction extent and location, would guide thresholds for acceptable peak pressure for that specific surgical procedure.

Figure 18A:
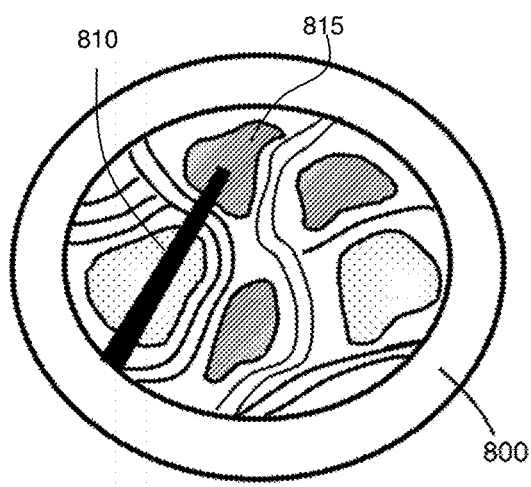
FIGS. 18A and 18B are diagrams, together, illustrating views of tissue, from the perspective of looking through an access port.
Figure 18B:
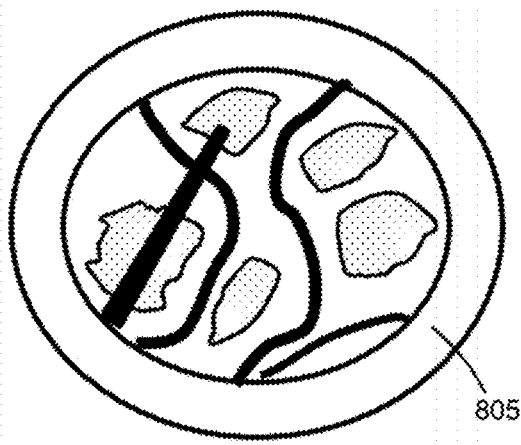

FIGS. 18A and 18B illustrate an example implementation in the context of a view looking down the access port. Shown in this figure on the top left is a view 800 of multiple types of tissues as seen by a video scan from a device such as an exo-scope. Here various colors, and textures create the appearance of multiple tissue types. Shown are five separate islands of tissue, with differing appearance, and lines that may represent planes between tissues, vessels or nerve fibers. With only the optical view of the tissue, it is not possible to differentiate between the tissue types with certainty.

Figure 18C:
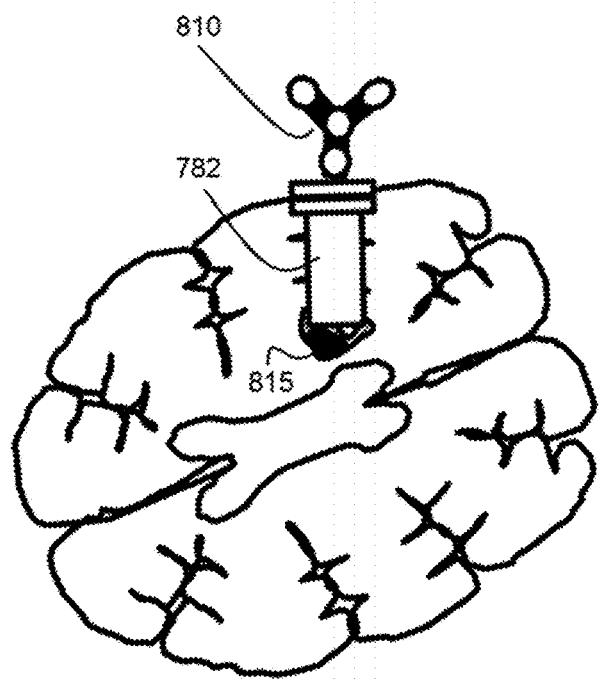
FIG. 18C is a diagram illustrating a probe interrogating an island of tissue through an access port.

In FIG. 18C, a probe 810 is shown interrogating an island of tissue 815 through access port 782. In one example implementation, this probe may be a Raman probe. The associated tissue spectra obtained from the Raman probe is represented in the frequency spectra shown at 850 in FIG. 19, under the title "In-vivo Imaging Data." This specific location in the port, and on the video image, can be located by tracking the position of the tip of the Raman imaging probe 810. This specific location may have, associated with it, additional local imaging data, either collected in that surgical procedure, or from prior diagnostic imaging exams (this information would be could registered through various registration methods). This specific location may also have associated regional, or volumetric imaging data, for example, which may have been obtained in this surgical procedure, or in prior pre-surgical scans.

If spatial registration can be adequately performed, then additional metrics associated with the other imaging data, such as contrast uptake, DWI ADC values, or other metrics useful in helping to differentiate or characterize the tissue, can be associated with this particular sampled point (or region outlined by a probe). In one non-limiting example, a reformatted image, such as FIG. 18B, may be created by specifically highlighting all regions of the DWI ADC image that correspond to the particular ADC value measured at the same location where the Raman data was acquired. Image highlighting described here may be realized through selective coloring of DWI ADC image pixels with specific values described above.

Referring now to FIG. 18B, a view 805 is shown down access port 782 from the video scan, providing the above described reformatted and registered view of an image down the same port trajectory. Registration will be required because the DWI ADC image needs to be transformed to match the view down the port. In this representation of the tissues of interest, it can be seen that the islands of tissue have a similar appearance and classification.

Figure 19:
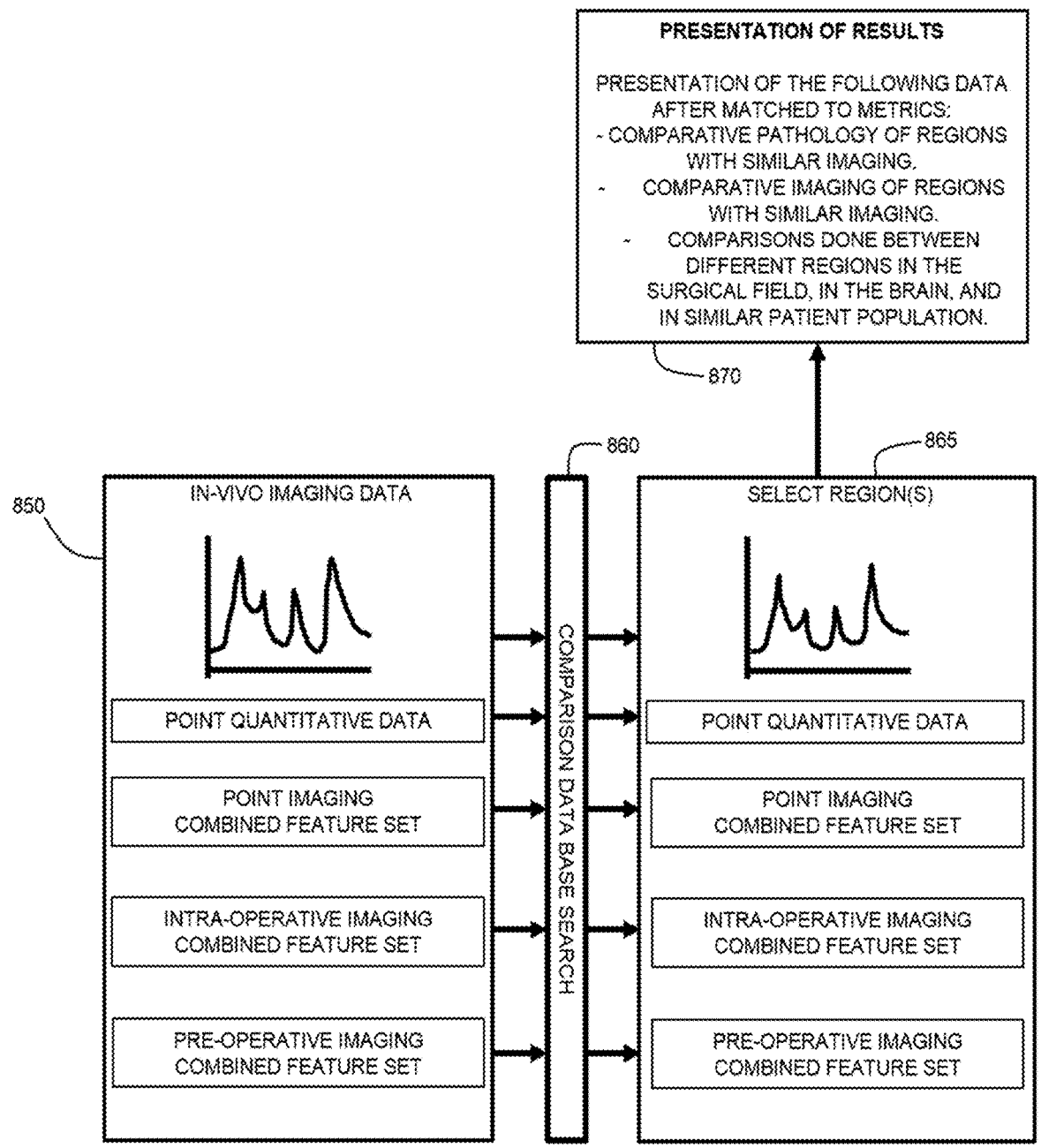
FIG. 19 is a diagram illustrating a manner in which multiple tissue metrics are utilized to characterize tissue of interest.

FIG. 19 is a diagram demonstrating how multiple tissue metrics are utilized to characterize tissue of interest, and how that information is used to search a database for similar tissue types characterized on a similar metrics. The ranked similar tissue types are then associated with their respective full-imaging set, pathology, and subject information, which are presented to the physician. As shown in FIG. 19, these features can be used to help differentiate the tissue of interest that is being interrogated. This is represented at 850 by the box with the label "In-vivo Imaging Data." The point of interest can be associated with different metrics or criteria, such as i) local quantitative data (such as ratios between peaks on the Raman spectra, or absolute point quantities such as tissue anisotropy, or tissue density can be determined based on ADC measurements, as described before), ii) local imaging combined feature set, (such as tissue morphology on a local scale), iii) intraoperative combined feature set (such as DWI, contrast flow, etc.), iv) preoperative imaging combined feature set (registered data including DWI, contrast flow, etc.). These metrics can then be used to search a database for similar tissue, based on a similarity analysis or algorithm, shown as "comparison" 860 in the figure. The actual mechanism for comparison may be as described in FIG. 14A and 14B.

The database search could be performed in a similar manner of weighting, and ranking described previously. In some embodiments, the search may be performed based on diagnostic data obtained through measurements of other regions that were done within the same subject. In the context of imaging through a small surgical window to address a larger area of interest surgically, the ability to piece together a full view of the regions of interest can be lost as the surgeon traverses through areas of tissue.

As specific regions are interrogated in above described manner against previously stored data in archival data set, some of the interrogated regions may be stored for easy recall during the same procedure. In other words, the database or archival data set that is searched is now composed of the original archival data set and any new tissues regions that were interrogated recently. The same search algorithm may be employed to search any new data against this expanded data set. Hence, the surgeon may explore the possibility of comparing a new tissue regions against previously analyzed tissue region. For example, the Raman spectroscopy data from a new tissue region may be compared with Raman spectroscopy data from a previously analyzed tissue region in the same patient.

The surgeon may use this information simply to inquire whether the tissue under local interrogation is simply similar to tissue adjacent or more similar to tissue that was seen previously, and clearly differentiable based on other imaging metrics. Accordingly, the surgeon is provided with the ability to reference information that was previously available, and interrogate tissue using various tissue metrics.

In a further example of what has been described, intraoperative imaging and preoperative imaging can be combined to better define set of pathology types based on similarity metrics.

Example 4

Intraoperative Analysis and Search of Tissue Analysis Database

Figure 20:
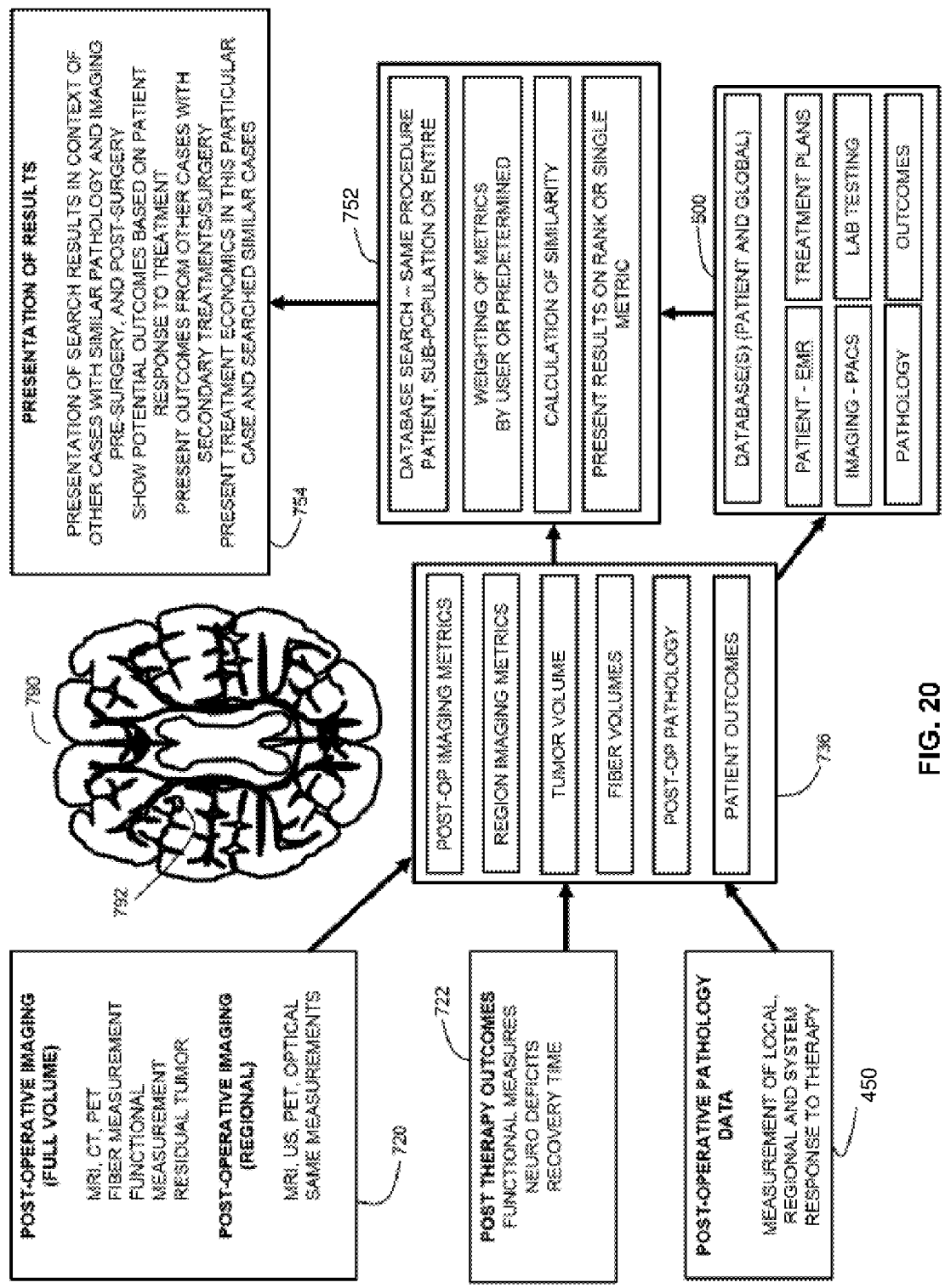
FIG. 20 is a diagram illustrating an example embodiment involving specific utilization of postoperative imaging in the context of expected outcomes.

FIG. 20 illustrates another example embodiment involving specific utilization of postoperative imaging 720, postoperative pathology data 724, and postoperative therapy outcomes 722, to facilitate decision making for next stage care, in the context of expected outcomes. As shown in FIG. 20, multiple tissue metrics may be utilized to characterize tissue of interest, and how that information is used to search a database for similar tissue types characterized on a similar metrics database 500 is searched 752 using one or more metrics 736, such that the results of previous surgeries performed on the subject, or subjects with similar imaging and/or pathology and or treatment response 754 are presented based on an algorithmic search 752.

Shown centrally in the figure, is an axial view of a brain 530, with the overlay of the residual tumor 792, and the nerve fascicles. In this example context, the tumor, and brain tissue is evaluated after the surgical procedure either using a full-volume scan, or a regional scan. The evaluation may be done immediately after the surgery, or done at various intervals at any times after the surgery is done, and may be informed based on patient response, or metrics from the database discussed in this disclosure (for instance a specific follow-up imaging regiment may be suggested for a certain tumor size, location and subject age). The postoperative imaging 720 is used to evaluate the tumor, and tissue metrics such as tumor volume, total fiber volume locally, regionally and throughout the brain. In addition postoperative pathology data 724 may be obtained, and registered to the imaging set.

Further still, post-surgery outcomes 722 may be used to define quantifiable metrics such as neurological deficits (motor response, visual field coverage, cognitive testing results, etc.). Each of these metrics can be calculated in part, or whole by the software system, and can be compared to a database in manners previously discussed. For instance, a specific residual tumor volume, with specific imaging metrics (DWI ADC, Contrast uptake), located in a specific region of the brain, and subject age, may be searched against similar metrics in the data base, or find the best long-term outcomes. The search, and presentation of the data would be done in a manner similar to that presented in the second context of use—surgical planning It is essentially the same process, as the next clinical decision for the treatment of the subject is based on a similar process of searching for similar conditions, and considering those outcomes in comparison to the current subject, and specific context of their disease and subject history thus far.

Another unique feature of the present disclosure may involve the knowledge that tumors are inherently heterogeneous, and that tumor biology has a fundamental impact on treatment—therefore point-wise pathological analysis should be linked to regional treatment selections. The pathology linked to a specific region of interest can instruct secondary local imaging (in same procedure), treatments (in same procedure) or secondary imaging (secondary procedure), or treatments (secondary procedure). Specific biomarkers can be selected for, for which specific imaging targets may be selected, or specific therapies. These biomarkers may instruct selection from a set of "off-the-shelf" therapies or contrast agents, or specific targets may be developed for that subject/tumor combination. Therefore, the response of the particular subject to the therapy (surgical, radiation, chemotherapy), can guide further therapies in the context of the imaging, pathology, and a larger subject outcome database.

In summary, according to various embodiments of the present disclosure, tracking of preoperative imaging, intraoperative imaging, and pathology results in a system that can link the information back to the original diagnosis, and allow the information to be accessible in the operating room to be integrated between pathology, surgery and radiology. In this way the actual results can be used to support better-informed diagnostic decision making in the future. There does not exist an integrated system in this manner today, as typically radiologists are separated from the actual outcomes and any intraoperative imaging that can be used to support pathology, or radiology is not integrated in any manner. Likewise, in the pathology lab, the imaging information can be provided to with respect to the location of interest from which the sample is obtained, and any imaging information associated with it. Pathology diagnosis can be made more accurate if the context in which the sample is obtained is provided, as well as protecting against any potential processing errors (for instance a completely wrong imaging to pathology correlation may indicate the wrong sample, or a sample taken from the wrong area of interest).

As described below, many of the shortcomings associated with existing solutions can be addressed through deeper integration of imaging and tissue biopsy. With this more integrated combination of regional and localized imaging, biopsy of samples, and localized, personalized treatment, the following problems with existing solutions may be addressed in the present disclosure: the inability of existing solutions to track locations of individual biopsy samples, and in-vivo imaging of the regions where those samples were selected from; the lack of an existing method to locate virtual "sticky" points or "geo locations" in the subject in-vivo that correspond to biopsy sample locations, critical structures, or tumor margin locations; the lack of an existing method to link together preoperative, intraoperative, biopsy locations that are common; the lack of an existing method to perform intraoperative imaging of tissue using the same modality that was used to diagnose the tissue (for instance an MRI DWI system that performed imaging on the excised surgical sample); the lack of an existing method to locate small regions of interest in the intraoperative system for local sampling or imaging; the lack of an existing method to search through databases of information linking common preoperative imaging, intraoperative imaging, and pathology reports to better inform decision making at all levels; the lack of an existing method to link from radiology to location specific intraoperative imaging information (in this way, common preoperative imaging information can be linked to a set of intraoperative imaging sets that are representative of that information); the inability for a radiologist to link location specific pathology information back to imaging in a way that can better inform current and future clinical diagnosis and conversely; the inability for the pathologist to access prior, or intraoperative imaging to better inform decision-making; the inability, based on existing solutions, to use common imaging taken in-vivo and ex-vivo to ensure the pathology specimen is properly tracked through the clinical chain; the inability, based on existing solutions, to use the biopsy specific information, such as antibody status, or genetic status, to link to better intraoperative imaging or therapy options either within the same procedure, or done on another occasion; and the inability, based on existing solutions, to build up such a comprehensive database of pathology, in-vivo and ex-vivo (preoperative, intraoperative and postoperative), and link it in a system that can be used for a subject at either the preoperative, the planning, surgery or treatment.

The specific embodiments described above have been shown by way of example, and understood is that these embodiments may be susceptible to various modifications and alternative forms. Further understood is that the claims are not intended to be limited to the particular forms disclosed, but rather to cover all modifications, equivalents, and alternatives falling within the spirit and scope of this disclosure.

What is claimed:

1. A method of performing intraoperative biopsy tracking during at least one medical procedure, by way of an automatic system comprising: a control and processing system comprising a processor, a tracking system, and a tracking engine interfaced with the processor and the tracking system; a storage device interfaced with the control and a processing system; and an external user input and output device interfaced with the control and a processing system comprising providing a display device, the method comprising:

comparing, according to pre-selected similarity criteria, biopsy analysis data and archival biopsy analysis data associated with at least one medical procedure by using the processor, comparing comprising:

detecting and identifying a plurality of local features in images relating to the biopsy analysis data and images relating to the archival biopsy data by using computer vision;

detecting and identifying a plurality of local features in an initial medical image by using a scale-invariant feature transform algorithm to facilitate searching biopsy analysis data and archival biopsy data, using the scale-invariant feature transform algorithm comprising: producing a difference image from the initial medical image by blurring the initial medical image, thereby producing a blurred image; subtracting the blurred image from the initial medical image, thereby producing the difference image; locating pixel amplitude extrema in the difference image; defining a corresponding pixel region about each pixel amplitude extremum of the pixel amplitude extrema; producing a plurality of component subregion descriptors for each subregion of a pixel region about the pixel amplitude extrema in the difference image; correlating the plurality of component subregion descriptors for each subregion of the pixel region about the pixel amplitude extrema in the difference image with a plurality of component subregion descriptors for each subregion of a pixel region about the pixel amplitude extrema in the initial medical image; and indicating detection of each local feature of the plurality of local features if a number of component subregion descriptors of the plurality of component subregion descriptors defines an aggregate correlation exceeding a threshold correlation;

reducing a size of the biopsy analysis data and the archival biopsy data by decomposing images relating to a clinical data set using at least one feature extraction algorithm, the clinical data set comprising data relating to at least one of: imaging contrast dynamics, diffusion information, quantitative T1 and T2, CT contrast flow, and PET tracer dynamics, whereby searching the biopsy analysis data and the archival biopsy data is performed in a dimensional space less than that corresponding to all of the biopsy analysis data and the archival biopsy data; and correlating apparent diffusion coefficient (ADC) with cellularity to build a mathematical model by using additional clinically relevant criteria comprising at least one of: a tumor size, a tumor location, a tumor histology, and a pathology result, thereby transforming measured ADC values into cellularity measures.

2. The method according to claim 1, wherein comparing further comprises:

obtaining and automatically recording the initial medical image of at least a portion of a subject by using the tracking system;

registering the initial medical image to an intraoperative reference frame associated with the subject by the processor;

intraoperatively tracking and automatically recording at least one biopsy instrument by using the tracking system;

intraoperatively detecting and automatically recording at least one location associated with at least one biopsy intraoperatively performed on the subject by using the tracking system;

displaying at least one hyperlinked reference marker associated with the at least one biopsy on the medical image by using the display device, displaying comprising displaying the at least one hyperlinked reference marker in relation to the at least one location corresponding to the at least one biopsy, and displaying comprising displaying the at least one hyperlinked reference marker as at least one of a label and text, whereby a given hyperlinked reference marker is selectable from the at least one hyperlinked reference marker, and whereby at least one of associated diagnostic data and biopsy analysis data is viewable;

obtaining and automatically recording the biopsy analysis data corresponding the at least one biopsy by using the processor;

receiving input, identifying a selected hyperlinked reference marker associated with a selected biopsy, by using the display device; and presenting at least a portion of the biopsy analysis data associated with the selected hyperlinked reference marker, by using the display device.

3. The method according to claim 2, further comprising:

intraoperatively acquiring local in-vivo diagnostic data from a local diagnostic measurement performed in a region associated with the at least one biopsy; and in the event that local in-vivo diagnostic data is available for the biopsy associated with the selected reference marker, presenting at least a portion of the local intraoperative diagnostic data associated with the selected reference marker, wherein displaying further comprises displaying the at least one hyperlinked reference marker as at least one of an icon and a tag, wherein comparing, according to the pre-selected similarity criteria, comprises evaluating at least metric associated with at least one local tissue analysis performed on the subject and at least one prior local tissue analysis, the at least one prior local tissue analysis associated with at least one of a medical history of the subject and a plurality of medical histories associated with a collection of other subjects, wherein the biopsy analysis data is obtained intraoperatively, wherein receiving the input comprises intraoperatively receiving the input, and wherein presenting the biopsy analysis data comprises intraoperatively presenting the biopsy analysis data.

4. The method according to claim 3, wherein a diagnostic modality, associated with the local diagnostic measurement, comprises an imaging modality.

5. The method according to claim 3, wherein a diagnostic modality, associated with the local diagnostic measurement, comprises an optical modality.

6. The method according to claim 5, wherein the optical modality, associated with the local diagnostic measurement, comprises an optical imaging modality.

7. The method according to claim 5, wherein the optical modality, associated with the local diagnostic measurement, comprises Raman spectroscopy.

8. The method according to claim 5, wherein the optical modality, associated with the local diagnostic measurement, comprises hyperspectral analysis.

9. The method according to claim 2, further comprising providing a visual representation of an estimated error, associated with the accuracy of the at least one location corresponding to the at least one biopsy by using the display device.

10. The method according to claim 2, wherein the biopsy analysis data is overlaid on the medical image.

11. The method according to claim 2, wherein the biopsy analysis data is displayed in a separate window of a user interface.

12. The method according to claim 2, wherein obtaining and automatically recording the medical image is preoperatively performed.

13. The method according to claim 2, wherein obtaining and automatically recording the medical image and intraoperatively performing the at least one biopsy are intraoperatively performed during the at least one medical procedure.

14. An automatic system for intraoperative biopsy tracking during a medical procedure, the automatic system comprising:
a tracking system; and
a control and processing system comprising a processor and a tracking engine interfaced with the processor and the tracking system, a storage device interfaced with the control and a processing system, the storage device comprising a memory, and an external user input and output device, the external use input and output device comprising a display device, said memory storing instructions, which, when executed by said the processor, configures the control and processing system to:
compare, according to pre-selected similarity criteria, biopsy analysis data and archival biopsy analysis data associated with the at least one medical procedure by using the processor to:
detect and identify local features in images relating to the biopsy analysis data and images relating to the archival biopsy data by using computer vision;
detect and identify local features in an initial medical image by using a scale-invariant feature transform algorithm to facilitate searching the biopsy analysis data and the archival biopsy data, using the scale-invariant feature transform algorithm comprising: producing a difference image from the initial medical image by blurring the initial medical image, thereby producing a blurred image; subtracting the blurred image from the initial medical image, thereby producing the difference image; locating pixel amplitude extrema in the difference image; defining a corresponding pixel region about each pixel amplitude extremum of the pixel amplitude extrema; producing a plurality of component subregion descriptors for each subregion of a pixel region about the pixel amplitude extrema in the difference image; correlating the plurality of component subregion descriptors for each subregion of the pixel region about the pixel amplitude extrema in the difference image with a plurality of component subregion descriptors for each subregion of a pixel region about the pixel amplitude extrema in the initial medical image; and indicating detection of each local feature of the plurality of local features if a number of component subregion descriptors of the plurality of component subregion descriptors defines an aggregate correlation exceeding a threshold correlation;
reduce a size of the biopsy analysis data and the archival biopsy data by decomposing images relating to a clinical data set by using at least one feature extraction algorithm, the clinical data set comprising data relating to at least one of: imaging contrast dynamics, diffusion information, quantitative T1 and T2, CT contrast flow, and PET tracer dynamics, whereby searching the biopsy analysis data and the archival biopsy data is performed in a dimensional space less than that corresponding to all of the biopsy analysis data and the archival biopsy data; and
build a mathematical model by: using additional clinically relevant criteria, comprising at least one of: a tumor size, a tumor location, a tumor histology, and a pathology result, and correlating apparent diffusion coefficient (ADC) with cellularity, thereby transforming measured ADC values into cellularity measures.

15. The system according to claim 14, wherein the processor is further configured to:
obtain and automatically record an initial medical image of at least a portion of a subject by using the tracking system;
register the medical image to an intraoperative reference frame associated with the subject by using the processor;
intraoperatively track at least one biopsy instrument by using the tracking system;
intraoperatively track and automatically record the at least one biopsy instrument by using the tracking system;
intraoperatively detect and automatically record at least one location associated with at least one biopsy intraoperatively performed on the subject by using the tracking system;
display at least one hyperlinked reference marker associated with the at least one biopsy on the medical image by using the display device, the at least one hyperlinked reference marker displayed in relation to the at least one location corresponding to the at least one biopsy, and the at least one hyperlinked reference marker comprising at least one of a label and text, whereby a given hyperlinked reference marker is selectable from the at least one hyperlinked reference marker, and whereby at least one of associated diagnostic data and biopsy analysis data is viewable;
obtain and automatically record biopsy analysis data corresponding to the at least one biopsy by using the processor;
receive input identifying a selected hyperlinked reference marker associated with a selected biopsy by using the display device; and
present at least a portion of the biopsy analysis data associated with the selected hyperlinked reference marker by using the display device.

16. The system according to claim 15, further comprising a diagnostic measurement device operably coupled with the control and processing system, wherein said control and processing system is further configured to:
intraoperatively acquire local in-vivo diagnostic data from a local diagnostic measurement performed in a region associated with the at least one biopsy by using the diagnostic measurement device; and
in the event that local in-vivo diagnostic data is available for the biopsy associated with the selected reference marker, presenting at least a portion of the local in-vivo diagnostic data associated with the selected reference marker by using the display device,
wherein the at least one hyperlinked reference marker further comprises at least one of an icon and a tag,
wherein a comparison, according to the pre-selected similarity criteria, comprises an evaluation of at least metric associated with at least one local tissue analysis performed on the subject and at least one prior local tissue analysis, the at least one prior local tissue analysis associated with at least one of a medical history of the subject and a plurality of medical histories associated with a collection of other subjects, wherein the biopsy analysis data is intraoperatively obtained, wherein the input is intraoperatively received, and wherein the biopsy analysis data is intraoperatively presented.

17. The system according to claim 16, wherein a diagnostic modality, associated with the local diagnostic measurement, comprises an imaging modality.

18. The system according to claim 17, wherein the imaging modality, associated with the local diagnostic measurement, comprises an optical imaging modality.

19. The system according to claim 16, wherein a diagnostic modality, associated with the local diagnostic measurement, comprises Raman spectroscopy.

20. The system according to claim 15, wherein said control and processing system is further configured to provide, in the displayed medical image, a visual representation of an estimated error associated with the accuracy of the location corresponding to the at least one biopsy by using the display device.

* * * * *